(12) United States Patent
Kadow et al.

(10) Patent No.: US 6,900,206 B2
(45) Date of Patent: May 31, 2005

(54) INDOLE, AZAINDOLE AND RELATED HETEROCYCLIC SULFONYLUREIDO PIPERAZINE DERIVATIVES

(75) Inventors: John F. Kadow, Wallingford, CT (US); Alicia Regueiro-Ren, Middletown, CT (US); Qiufen May Xue, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/457,620

(22) Filed: Jun. 9, 2003

(65) Prior Publication Data

US 2004/0006090 A1 Jan. 8, 2004

Related U.S. Application Data

(60) Provisional application No. 60/390,195, filed on Jun. 20, 2002.

(51) Int. Cl.[7] .................. A61K 31/496; A61K 31/5377; C07D 403/06; C07D 471/04
(52) U.S. Cl. .............................. 514/235.2; 514/253.04; 514/253.09; 514/254.09; 544/121; 544/362; 544/364; 544/373; 544/60; 544/61; 544/179; 544/180; 544/182; 544/238; 544/295; 544/357; 544/366; 544/367; 544/368; 544/369; 544/370; 544/371
(58) Field of Search ................................ 544/121, 362, 544/364, 373; 514/235.2, 253.04, 253.09, 254.09

(56) References Cited

U.S. PATENT DOCUMENTS 5,023,265 A 6/1991 Scherlock et al.

(Continued)

FOREIGN PATENT DOCUMENTS

| EP | 0530907 A1 | 3/1993 |
|---|---|---|
| WO | WO 93/01181 | 1/1993 |
| WO | WO 95/04742 | 2/1995 |
| WO | WO 96/11929 | 4/1996 |
| WO | WO 02/62423 | 8/2002 |

OTHER PUBLICATIONS

M. Font, et al, "Indoles and Pyridazino[4,5–b]Indoles as Nonnucleoside Analog Inhibitors of HIV–1 Reverse Transcriptase," Eur. J. Med. Chem., 30, pp. 963–971, 1995.

(Continued)

*Primary Examiner*—Emily Bernhardt
(74) *Attorney, Agent, or Firm*—Samuel J. DuBoff

(57) ABSTRACT

This invention provides compounds having drug and bio-affecting properties, their pharmaceutical compositions and method of use. In particular, the invention is concerned with sulfonylureido piperazine derivatives of Formula I. These compounds possess unique antiviral activity, whether used alone or in combination with other antivirals, antiinfectives, immunomodulators or HIV entry inhibitors. More particularly, the present invention relates to the treatment of HIV and AIDS.

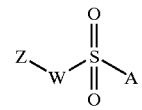

wherein:

Z is

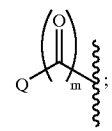

Q is selected from the group consisting of:

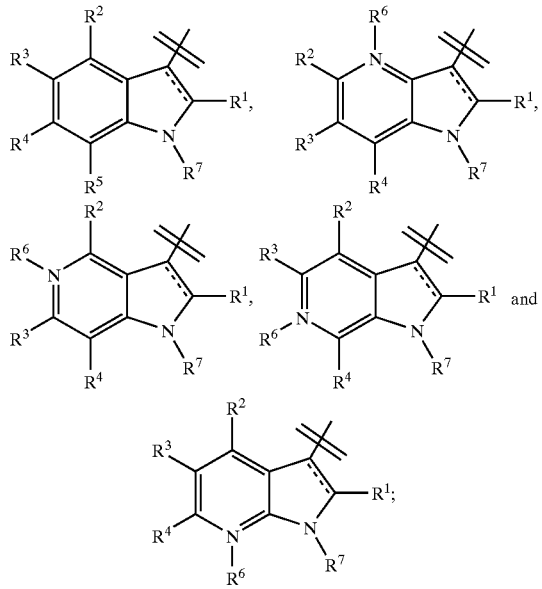

—W— is

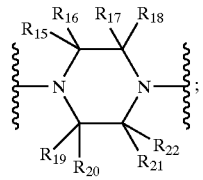

— represents a carbon-carbon bond or does not exist; and
A is $NR^{13}R^{14}$.

15 Claims, No Drawings

U.S. PATENT DOCUMENTS

| | | | |
|---|---|---|---|
| 5,124,327 | A | 6/1992 | Greenlee et al. |
| 5,424,329 | A | 6/1995 | Boschelli et al. |
| 6,469,006 | B1 | 10/2002 | Blair et al. |
| 6,476,034 | B2 | 11/2002 | Wang et al. |
| 6,573,262 | B2 | 6/2003 | Wallace et al. |
| 2003/0162970 | A1 | 8/2003 | Mavunkel et al. |

OTHER PUBLICATIONS

D. L. Romero, et al, J. Med. Chem., 36, pp. 1505–1508, 1993.

S. D. Young, et al, "2–Heterocyclic Indole–3–Sulfones as Inhibitors of HIV–1 Reverse Transcriptase," Bioorganic & Medicinal Chemistry Letters, 5(5), pp. 491–496, 1995.

M. J. Genin, et al, "Synthesis and Bioactivity of Novel Bis(Heteroaryl)Piperazine (BHAP) Reverse Transcriptase Inhibitors: Structure–Activity Relationships and Increased Metabolic Stability of Novel Substituted Pyridine Analogs," J. Med. Chem., 39, pp. 5267–5275, 1996.

R. Silvestri, et al, Antiviral Chemistry & Chemotherapy, 9, pp. 139–148, 1998.

A. Fredenhagen, et al, "Semicochliodinol A and B: Inhibitors of HIV–1 Protease and EGF–R Protein Tyrosine Kinase Related to Asterriquinones Produced by the Fungus *Chrysosporium Merdarium*," Journal Of Antibiotics, 50(5), pp. 395–401, 1997.

M. Kato, et al, "New 5–$HT_3$ (Serotonin–3) Receptor Antagonists. IV. Synthesis and Structure–Activity Relationships of Azabicycloalkaneacetamide Derivatives," Chem. Pharm. Bull., 43(8), pp. 1351–1357, 1995.

V. Levacher, et al, "Broadening in the Scope of NADH Models by Using Chiral and Non–Chiral Pyrrolo [2,3–b] Pyridine Derivatives," Tetrahedron, 47(3), pp. 429–440, 1991.

INDOLE, AZAINDOLE AND RELATED HETEROCYCLIC SULFONYLUREIDO PIPERAZINE DERIVATIVES

REFERENCE TO RELATED APPLICATIONS

This application claims the benefit of U.S. Provisional Application Ser. No. 60/390,195 filed Jun. 20, 2002.

FIELD OF THE INVENTION

This invention provides compounds having drug and bio-affecting properties, their pharmaceutical compositions and method of use. In particular, the invention is concerned with new heterocyclic sulfonylureido piperazines derivatives that possess unique antiviral activity. More particularly, the present invention relates to compounds useful for the treatment of HIV and AIDS.

BACKGROUND ART

HIV-1 (human immunodeficiency virus-1) infection remains a major medical problem, with an estimated 42 million people infected worldwide at the end of 2002. The number of cases of HIV and AIDS (acquired immunodeficiency syndrome) has risen rapidly. In 2002, ~5.0 million new infections were reported, and 3.1 million people died from AIDS. Currently available drugs for the treatment of HIV include nine nucleoside reverse transcriptase (RT) inhibitors or approved single pill combinations(zidovudine or AZT (or Retrovir®), didanosine (or Videx®), stavudine (or Zerit®), lamivudine (or 3TC or Epivir®), zalcitabine (or DDC or Hivid®), abacavir succinate (or Ziagen®), Tenofovir disoproxil fumarate salt (or Viread®), Combivir® (contains –3TC plus AZT), Trizivir® (contains abacavir, lamivudine, and zidovudine); three non-nucleoside reverse transcriptase inhibitors: nevirapine (or Viramune®), delavirdine (or Rescriptor®) and efavirenz (or Sustiva®), and seven peptidomimetic protease inhibitors or approved formulations: saquinavir, indinavir, ritonavir, nelfinavir, amprenavir, lopinavir, and Kaletra® (lopinavir and Ritonavir). Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present (Larder and Kemp; Gulick; Kuritzkes; Morris-Jones et al; Schinazi et al; Vacca and Condra; Flexner; Berkhout and Ren et al; (Ref. 6–14)). Therefore, novel anti-HIV agents exhibiting distinct resistance patterns, and favorable pharmacokinetic as well as safety profiles are needed to provide more treatment options.

Currently marketed HIV-1 drugs are dominated by either nucleoside reverse transcriptase inhibitors or peptidomimetic protease inhibitors. Non-nucleoside reverse transcriptase inhibitors (NNRTIs) have recently gained an increasingly important role in the therapy of HIV infections (Pedersen & Pedersen, Ref 15). At least 30 different classes of NNRTI have been described in the literature (De Clercq, Ref. 16) and several NNRTIs have been evaluated in clinical trials. Dipyridodiazepinone (nevirapine), benzoxazinone (efavirenz) and bis(heteroaryl) piperazine derivatives (delavirdine) have been approved for clinical use. However, the major drawback to the development and application of NNRTIs is the propensity for rapid emergence of drug resistant strains, both in tissue cell culture and in treated individuals, particularly those subject to monotherapy. As a consequence, there is considerable interest in the identification of NNRTIs less prone to the development of resistance (Pedersen & Pedersen, Ref 15). A recent overview of non-nucleoside reverse transcriptase inhibitors: perspectives on novel therapeutic compounds and strategies for the treatment of HIV infection has appeared (Buckheit, reference 99). A review covering both NRTI and NNRTIs has appeared (De clercq, reference 100). An overview of the current state of the HIV drugs has been published (De clercq, reference 101).

Several indole derivatives including indole-3-sulfones, piperazino indoles, pyrazino indoles, and 5H-indolo[3,2-b][1,5]benzothiazepine derivatives have been reported as HIV-1 reverse transcriptase inhibitors (Greenlee et al, Ref. 1; Williams et al, Ref. 2; Romero et al, Ref. 3; Font et al, Ref. 17; Romero et al, Ref. 18; Young et al, Ref. 19; Genin et al, Ref. 20; Silvestri et al, Ref. 21). Indole 2-carboxamides have also been described as inhibitors of cell adhesion and HIV infection (Boschelli et al, U.S. Pat. No. 5,424,329, Ref. 4). 3-substituted indole natural products (Semicochliodinol A and B, didemethylasterriquinone and isocochliodinol) were disclosed as inhibitors of HIV-1 protease (Fredenhagen et al, Ref. 22).

Structurally related aza-indole amide derivatives have been disclosed previously (Kato et al, Ref. 23; Levacher et al, Ref. 24; Dompe Spa, WO-09504742, Ref. 5(a); SmithKline Beecham PLC, WO-09611929, Ref. 5(b); Schering Corp., U.S.-05023265, Ref. 5(c)). However, these structures differ from those claimed herein in that they are aza-indole mono-amide rather than unsymmetrical aza-indole piperazine sulfonylureido derivatives, and there is no mention of the use of these compounds for treating viral infections, particularly HIV. Indole and azaindole piperazine containing derivatives have been disclosed in three different PCT and issued U.S. patent applications (Reference 93–95, 106) None of these applications discloses sulfonylureido piperazines compounds such as described in this invention.

Nothing in these references can be construed to disclose or suggest the novel compounds of this invention and their use to inhibit HIV infection.

REFERENCES CITED

Patent Documents
1. Greenlee, W. J.; Srinivasan, P. C. Indole reverse transcriptase inhibitors. U.S. Pat. No. 5,124,327.
2. Williams, T. M.; Ciccarone, T. M.; Saari, W. S.; Wai, J. S.; Greenlee, W. J.; Balani, S. K.; Goldman, M. E.; Theohrides, A. D. Indoles as inhibitors of HIV reverse transcriptase. European Patent 530907.
3. Romero, D. L.; Thomas, R. C.; Preparation of substituted indoles as anti-AIDS pharmaceuticals. PCT WO 93/01181.
4. Boschelli, D. H.; Connor, D. T.; Unangst, P. C. Indole-2-carboxamides as inhibitors of cell adhesion. U.S. Pat. No. 5,424,329.
5. (a) Mantovanini, M.; Melillo, G.; Daffonchio, L. Tropyl 7-azaindol-3-ylcarboxyamides as antitussive agents. PCT WO 95/04742 (Dompe Spa). (b) Cassidy, F.; Hughes, I.; Rahman, S.; Hunter, D. J. Bisheteroaryl-carbonyl and carboxamide derivatives with 5HT 2C/2B antagonists activity. PCT WO 96/11929. (c) Scherlock, M. H.; Tom, W. C. Substituted 1H-pyrrolopyridine-3-carboxamides. U.S. Pat. No. 5,023,265.

Other Publications

6. Larder, B. A.; Kemp, S. D. Multiple mutations in the HIV-1 reverse transcriptase confer high-level resistance to zidovudine (AZT). *Science*, 1989, 246, 1155–1158.
7. Gulick, R. M. Current antiretroviral therapy: An overview. *Quality of Life Research*, 1997, 6, 471–474.
8. Kuritzkes, D. R. HIV resistance to current therapies. *Antiviral Therapy*, 1997, 2 (Supplement 3), 61–67.
9. Morris-Jones, S.; Moyle, G.; Easterbrook, P. J. Antiretroviral therapies in HIV-1 infection. *Expert Opinion on Investigational Drugs*, 1997, 6(8),1049–1061.
10. Schinazi, R. F.; Larder, B. A.; Mellors, J. W. Mutations in retroviral genes associated with drug resistance. *International Antiviral News*, 1997, 5,129–142.
11. Vacca, J. P.; Condra, J. H. Clinically effective HIV-1 protease inhibitors. *Drug Discovery Today*, 1997, 2, 261–272.
12. Flexner, D. HIV-protease inhibitors. *Drug Therapy*, 1998, 338, 1281–1292.
13. Berkhout, B. HIV-1 evolution under pressure of protease inhibitors: Climbing the stairs of viral fitness. *J. Biomed. Sci.*, 1999, 6, 298–305.
14. Ren, S.; Lien, E. J. Development of HIV protease inhibitors: A survey. *Prog. Drug Res.*, 1998, 51, 1–31.
15. Pedersen, O. S.; Pedersen, E. B. Non-nucleoside reverse transcriptase inhibitors: the NNRTI boom. *Antiviral Chem. Chemother*. 1999, 10, 285–314.
16. (a) De Clercq, E. The role of non-nucleoside reverse transcriptase inhibitors (NNRTIs) in the therapy of HIV-1 infection. *Antiviral Research*, 1998, 38, 153–179. (b) De Clercq, E. Perspectives of non-nucleoside reverse transcriptase inhibitors (NNRTIs) in the therapy of HIV infection. IL. *Farmaco*, 1999, 54, 26–45.
17. Font, M.; Monge, A.; Cuartero, A.; Elorriaga, A.; Martinez-Irujo, J. J.; Alberdi, E.; Santiago, E.; Prieto, I.; Lasarte, J. J.; Sarobe, P. and Borras, F. Indoles and pyrazino[4,5-b]indoles as nonnucleoside analog inhibitors of HIV-1 reverse transcriptase. *Eur. J. Med. Chem.*, 1995, 30, 963–971.
18. Romero, D. L.; Morge, R. A.; Genin, M. J.; Biles, C.; Busso, M,; Resnick, L.; Althaus, I. W.; Reusser, F.; Thomas, R. C and Tarpley, W. G. Bis(heteroaryl) piperazine (BHAP) reverse transcriptase inhibitors: structure-activity relationships of novel substituted indole analogues and the identification of 1-[(5-methanesulfonamido-1H-indol-2-yl)-carbonyl]-4-[3-[1-methylethyl)amino]-pyridinyl]piperazine momomethansulfonate (U-90152S), a second generation clinical candidate. *J. Med. Chem.*, 1993, 36, 1505–1508.
19. Young, S. D.; Amblard, M. C.; Britcher, S. F.; Grey, V. E.; Tran, L. O.; Lumma, W. C.; Huff, J. R.; Schleif, W. A.; Emini, E. E.; O'Brien, J. A.; Pettibone, D. J. 2-Heterocyclic indole-3-sulfones as inhibitors of HIV-reverse transcriptase. *Bioorg. Med. Chem. Lett.*, 1995, 5, 491–496.
20. Genin, M. J.; Poel, T. J.; Yagi, Y.; Biles, C.; Althaus, I.; Keiser, B. J.; Kopta, L. A.; Friis, J. M.; Reusser, F.; Adams, W. J.; Olmsted, R. A.; Voorman, R. L.; Thomas, R. C. and Romero, D. L. Synthesis and bioactivity of novel bis(heteroaryl)piperazine (BHAP) reverse transcriptase inhibitors: structure-activity relationships and increased metabolic stability of novel substituted pyridine analogs. *J. Med. Chem.*, 1996, 39, 5267–5275.
21. Silvestri, R.; Artico, M.; Bruno, B.; Massa, S.; Novellino, E.; Greco, G.; Marongiu, M. E.; Pani, A.; De Montis, A and La Colla, P. Synthesis and biological evaluation of 5H-indolo[3,2-b][1,5]benzothiazepine derivatives, designed as conformationally constrained analogues of the human immunodeficiency virus type 1 reverse transcriptase inhibitor L-737,126. *Antiviral Chem. Chemother*. 1998, 9, 139–148.
22. Fredenhagen, A.; Petersen, F.; Tintelnot-Blomley, M.; Rosel, J.; Mett, H and Hug, P. J. Semicochliodinol A and B: Inhibitors of HIV-1 protease and EGF-R protein Tyrosine Kinase related to Asterriquinones produced by the fungus *Chrysosporium nerdarium*. *Antibiotics*, 1997, 50, 395–401.
23. Kato, M.; Ito, K.; Nishino, S.; Yamakuni, H.; Takasugi, H. New 5-HT$_3$ (Serotonin-3) receptor antagonists. IV. Synthesis and structure-activity relationships of azabicycloalkaneacetamide derivatives. *Chem. Pharm. Bull.*, 1995, 43, 1351–1357.
24. Levacher, V.; Benoit, R.; Duflos, J; Dupas, G.; Bourguignon, J.; Queguiner, G. Broadening the scope of NADH models by using chiral and non chiral pyrrolo [2,3-b] pyridine derivatives. *Tetrahedron*, 1991, 47, 429–440.
25. Shadrina, L. P.; Dormidontov, Yu. P.; Ponomarev, V, G.; Lapkin, I. I. Reactions of organomagnesium derivatives of 7-aza- and benzoindoles with diethyl oxalate and the reactivity of ethoxalylindoles. *Khim. Geterotsikl. Soedin.*, 1987, 1206–1209.
26. Sycheva, T. V.; Rubtsov, N. M.; Sheinker, Yu. N.; Yakhontov, L. N. Some reactions of 5-cyano-6-chloro-7-azaindoles and lactam-lactim tautomerism in 5-cyano-6-hydroxy-7-azaindolines. *Khim. Geterotsikl. Soedin.*, 1987, 100–106.
27. (a) Desai, M.; Watthey, J. W. H.; Zuckerman, M. A convenient preparation of 1-aroylpiperazines. *Org. Prep. Proced. Int.*, 1976, 8, 85–86. (b) Adamczyk, M.; Fino, J. R. Synthesis of procainamide metabolites. N-acetyl desethylprocainamide and desethylprocainamide. *Org. Prep. Proced. Int.* 1996, 28, 470–474. (c) Rossen, K.; Weissman, S. A.; Sager, J.; Reamer, R. A.; Askin, D.; Volante, R. P.; Reider, P. J. Asymmetric Hydrogenation of tetrahydropyrazines: Synthesis of (S)-piperazine 2-tert-butylcarboxamide, an intermediate in the preparation of the HIV protease inhibitor Indinavir. *Tetrahedron Lett.*, 1995, 36, 6419–6422. (d) Wang, T.; Zhang, Z.; Meanwell, N. A. Benzoylation of Dianions: Preparation of mono-Benzoylated Symmetric Secondary Diamines. *J. Org. Chem.*, 1999, 64, 7661–7662.
28. Li, H.; Jiang, X.; Ye, Y.-H.; Fan, C.; Romoff, T.; Goodman, M. 3-(Diethoxyphosphoryloxy)-1,2,3-benzotriazin-4(3H)-one (DEPBT): A new coupling reagent with remarkable resistance to racemization. *Organic Lett.*, 1999, 1, 91–93.
29. Harada, N.; Kawaguchi, T.; Inoue, I.; Ohashi, M.; Oda, K.; Hashiyama, T.; Tsujihara, K. Synthesis and antitumor activity of quaternary salts of 2-(2'-oxoalkoxy)-9-hydroxyellipticines. *Chem. Pharm. Bull.*, 1997, 45, 134–137.
30. Schneller, S. W.; Luo, J.-K. Synthesis of 4-amino-1H-pyrrolo[2,3-b]pyridine (1,7-Dideazaadenine) and 1H-pyrrolo[2,3-b]pyridin-4-ol (1,7-Dideazahypoxanthine). *J. Org. Chem.*, 1980, 45, 4045–4048.
31. Shiotani, S.; Tanigochi, K. Furopyridines. XXII [1]. Elaboration of the C-substitutents alpha to the heteronitrogen atom of furo[2,3-b]-, -[3.2-b]-, -[2.3-c]- and-[3,2-c]pyridine. *J. Het. Chem.*, 1997, 34, 901–907.
32. Minakata, S.; Komatsu, M.; Ohshiro, Y. Regioselective functionalization of 1H-pyrrolo[2,3-b]pyridine via its N-oxide. *Synthesis*, 1992, 661–663.
33. Klemm, L. H.; Hartling, R. Chemistry of thienopyridines. XXIV. Two transformations of thieno[2,3-b] pyridine 7-oxide (1). *J. Het. Chem.*, 1976, 13, 1197–1200.
34. Antonini, I.; Claudi, F.; Cristalli, G.; Franchetti, P.; Crifantini, M.; Martelli, S. Synthesis of 4-amino-1-β-D-ribofuranosyl-1H-pyrrolo[2,3-b]pyridine (1-Deazatubercidin) as a potential antitumor agent. *J. Med. Chem.*, 1982, 25, 1258–1261.
35. (a) Regnouf De Vains, J. B.; Papet, A. L.; Marsura, A. New symmetric and unsymmetric polyfunctionalized 2,2'-bipyridines. *J. Het. Chem.*, 1994, 31, 1069–1077. (b) Miura, Y.; Yoshida, M.; Hamana, M. Synthesis of 2,3-fused quinolines from 3-substituted quinoline 1-oxides. Part II, *Heterocycles*, 1993, 36, 1005–1016. (c) Profft, V. E.; Rolle, W. Uber 4-merkaptoverbindungendes 2-methylpyridins. *J. Prakt. Chem.*, 1960, 283 (11), 22–34.
36. Nesi, R.; Giomi, D.; Turchi, S.; Tedeschi, P., Ponticelli, F. A new one step synthetic approach to the isoxazolo[4,5-b]pyridine system. *Synth. Comm.*, 1992, 22, 2349–2355.
37. (a) Walser, A.; Zenchoff, G.; Fryer, R. I. Quinazolines and 1,4-benzodiazepines. 75. 7-Hydroxyaminobenzodiazepines and derivatives. *J. Med. Chem.*, 1976, 19, 1378–1381. (b) Barker, G.; Ellis, G. P. Benzopyrone. Part I. 6-Amino- and 6-hydroxy-2-substituted chromones. *J. Chem. Soc.*, 1970, 2230–2233.
38. Ayyangar, N. R.; Lahoti, R J.; Daniel, T. An alternate synthesis of 3,4-diaminobenzophenone and mebendazole. *Org. Prep. Proced. Int.*, 1991, 23, 627–631.
39. Mahadevan, I.; Rasmussen, M. Ambident heterocyclic reactivity: The alkylation of pyrrolopyridines (azaindoles, diazaindenes). *Tetrahedron*, 1993, 49, 7337–7352.
40. Chen, B. K.; Saksela, K.; Andino, R.; Baltimore, D. Distinct modes of human immunodeficiency type 1 proviral latency revealed by superinfection of nonproductively infected cell lines with recombinant luciferase-encoding viruses. *J. Virol.*, 1994, 68, 654–660.
41. Bodanszky, M.; Bodanszky, A. "*The Practice of Peptide Synthesis*" 2$^{nd}$ Ed., Springer-Verlag: Berlin Heidelberg, Germany, 1994.
42. Albericio, F. et al. *J. Org. Chem.* 1998, 63, 9678.
43. Knorr, R. et al. *Tetrahedron Lett.* 1989, 30, 1927.
44. (a) Jaszay Z. M. et al. *Synth. Commun.*, 1998 28, 2761 and references cited therein; (b) Bernasconi, S. et al. *Synthesis*, 1980, 385.
45. (a) Jaszay Z. M. et al. *Synthesis*, 1989, 745 and references cited therein; (b) Nicolaou, K. C. et al. *Angew. Chem. Int. Ed.* 1999, 38, 1669.
46. Ooi, T. et al. *Synlett*. 1999, 729.
47. Ford, R. E. et al. *J. Med. Chem.* 1986, 29, 538.
48. (a) Yeung, K.-S. et al. Bristol-Myers Squibb Unpublished Results. (b) Wang, W. et al. *Tetrahedron Lett.* 1999, 40, 2501.
49. Brook, M. A. et al. *Synthesis*, 1983, 201.
50. Yamazaki, N. et al. *Tetrahedron Lett.* 1972, 5047.
51. Barry A. Bunin "The Combinatorial Index" 1998 Academic Press, San Diego/London pages 78–82.
52. Richard C. Larock Comprehensive Organic Transormations 2nd Ed. 1999, John Wiley and Sons New York.
53. M. D. Mullican et. al. *J. Med. Chem.* 1991, 34, 2186–2194.
54. Protective groups in organic synthesis 3rd ed./Theodora W. Greene and Peter G. M. Wuts. New York: Wiley, 1999.
55. Katritzky, Alan R. Lagowski, Jeanne M. The principles of heterocyclic Chemistry New York: Academic Press, 1968.
56. Paquette, Leo A. Principles of modern heterocyclic chemistry New York: Benjamin.
57. Katritzky, Alan R.; Rees, Charles W.; Comprehensive heterocyclic chemistry: the structure, reactions, synthesis, and uses of heterocyclic compounds 1st ed.Oxford (Oxfordshire); New York: Pergamon Press, 1984. 8 v.
58. Katritzky, Alan RHandbook of heterocyclic 1st edOxford (Oxfordshire); New York: Pergamon Press, 1985.
59. Davies, David I Aromatic Heterocyclic Oxford; New York: Oxford University Press, 1991.
60. Ellis, G. P. Synthesis of fused Chichester [Sussex]; New York: Wiley, c1987-c1992. Chemistry of heterocyclic compounds; v. 47.
61. Joule, J. A Mills, K., Smith, G. F. Heterocyclic Chemistry, 3rd ed London; New York Chapman & Hall, 1995.
62. Katritzky, Alan R., Rees, Charles W., Scriven, Eric F. V. Comprehensive heterocyclic chemistry II: a review of the literature 1982–1995.
63. The structure, reactions, synthesis, and uses of heterocyclic compounds 1st ed. Oxford; New York: Pergamon, 1996. 11 v. in 12: ill.; 28 cm.
64. Eicher, Theophil, Hauptmann, Siegfried. The chemistry of heterocycles: structure, reactions, syntheses, and applications Stuttgart; New York: G. Thieme, 1995.
65. Grimmett, M. R. Imidazole and benzimidazole Synthesis London; San Diego: Academic Press, 1997.
66. Advances in heterocyclic chemistry. Published in New York by Academic Press, starting in 1963-present.
67. Gilchrist, T. L. (Thomas Lonsdale) Heterocyclic chemistry 3rd ed. Harlow, Essex: Longman, 1997. 414 p.: ill.; 24 cm.
68. Farina, Vittorio; Roth, Gregory P. Recent advances in the Stille reaction; *Adv. Met. -Org. Chem.* 1996, 5, 1–53.
69. Farina, Vittorio; Krishnamurthy, Venkat; Scott, William J. The Stille reaction; Org. React. (N.Y.) (1997), 50, 1–652.
70. Stille, J. K. *Angew. Chem. Int. Ed. Engl.* 1986, 25, 508–524.
71. Norio Miyaura and Akiro Suzuki *Chem Rev*. 1995, 95, 2457.
72. Home, D. A. *Heterocycles* 1994, 39, 139.
73. Kamitori, Y. et. al. *Heterocycles*, 1994, 37(1), 153.
74. Shawali, J. *Heterocyclic Chem.* 1976, 13, 989.
75. a) Kende, A. S. et al. *Org. Photochem. Synth.* 1972, 1, 92. b) Hankes, L. V.; *Biochem. Prep.* 1966, 11, 63. c) *Synth. Meth.* 22, 837.
76. Hulton et. al. *Synth. Comm.* 1979, 9, 789.
77. Pattanayak, B. K. et. al. *Indian J. Chem.* 1978, 16, 1030.
78. *Chemische Berichte* 1902, 35, 1545.
79. *Chemische Berichte* Ibid 1911, 44, 493.
80. Moubarak, I., Vessiere, R. *Synthesis* 1980, Vol. 1, 52–53.
81. *Ind J. Chem.* 1973, 11, 1260.
82. Roomi et. al. *Can J. Chem.* 1970, 48, 1689.
83. Sorrel, T. N. *J. Org. Chem.* 1994, 59, 1589.
84. Nitz, T. J. et. al. *J. Org. Chem.* 1994, 59, 5828–5832.
85. Bowden, K. et. al. *J. Chem. Soc.* 1946, 953.
86. Nitz, T. J. et. al. *J. Org. Chem.* 1994, 59, 5828–5832.
87. Scholkopf et. al. *Angew. Int. Ed. Engl.* 1971, 10(5), 333.
88. (a) Behun, J. D.; Levine, R. *J. Org. Chem.* 1961, 26, 3379. (b) Rossen, K.; Weissman, S. A.; Sager, J.; Reamer, R. A.; Askin, D.; Volante, R. P.; Reider, P. J. Asymmetric Hydrogenation of tetrahydropyrazines: Synthesis of (S)-piperazine 2-tert-butylcarboxamide, an intermediate in the preparation of the HIV protease inhibitor Indinavir. *Tetrahedron Lett.*, 1995, 36, 6419–6422. (c) Jenneskens, L. W.; Mahy, J.; den Berg, E. M. M. de B.-v.; Van der Hoef, I.; Lugtenburg, *J. Recl. Trav. Chim. Pays-Bas* 1995, 114, 97.
89. Wang, T.; Zhang, Z.; Meanwell, N. A. Benzoylation of Dianions: Preparation of mono-Benzoylated Symmetric Secondary Diamines. *J. Org. Chem.*, 1999, 64, 7661–7662.
90. (a) Adamczyk, M.; Fino, J. R. Synthesis of procainamide metabolites. N-acetyl desethylprocainamide and desethylprocainamide. *Org. Prep. Proced. Int.* 1996, 28, 470–474. (b) Wang, T.; Zhang, Z.; Meanwell, N. A. Regioselective mono-Benzoylation of Unsymmetrical Piperazines. *J. Org. Chem.*, in press.
91. Masuzawa, K.; Kitagawa, M.; Uchida, H. *Bull Chem. Soc. Jpn.* 1967, 40, 244–245.
92. Furber, M.; Cooper, M. E.; Donald, D. K. *Tetrahedron Lett.* 1993, 34, 1351–1354.
93. Blair, Wade S.; Deshpande, Milind; Fang, Haiquan; Lin, Pin-fang; Spicer, Timothy P.; Wallace, Owen B.; Wang, Hui; Wang, Tao; Zhang, Zhongxing; Yeung, Kap-sun. Preparation of antiviral indoleoxoacetyl piperazine derivatives U.S. Pat. No. 6,469,006. Preparation of antiviral indoleoxoacetyl piperazine derivatives. PCT Int. Appl. (PCT/US00/14359), WO 0076521 A1, filed May 24, 2000, published Dec. 21, 2000.
94. Wang, Tao; Wallace, Owen B.; Zhang, Zhongxing; Meanwell, Nicholas A.; Bender, John A. Antiviral azaindole derivatives. U.S. Pat. No. 6,476,034 and Wang, Tao; Wallace, Owen B.; Zhang, Zhongxing; Meanwell, Nicholas A.; Bender, John A. Preparation of antiviral azaindole derivatives. PCT Int. Appl. (PCT/US01/02009), WO 0162255 A1, filed Jan. 19, 2001, published Aug. 30, 2001.
95. Wallace, Owen B.; Wang, Tao; Yeung, Kap-Sun; Pearce, Bradley C.; Meanwell, Nicholas A.; Qiu, Zhilei; Fang, Haiquan; Xue, Qiufen May; Yin, Zhiwei. Composition and antiviral activity of substituted indoleoxoacetic piperazine derivatives. U.S. Pat. No. 6,573,262 granted Jun. 3, 2003 corresponding to PCT Int. Appl. (PCT/US01/20300), WO 0204440 A1, filed Jun. 26, 2001, published Jan. 17, 2002.
96. J. L. Marco, S. T. Ingate, and P. M. Chinchon *Tetrahedron* 1999, 55, 7625–7644.
97. C. Thomas, F. Orecher, and P. Gmeiner *Synthesis* 1998, 1491.
98. M. P. Pavia, S. J. Lobbestael, C. P. Taylor, F. M. Hershenson, and D. W. Miskell.
99. Buckheit, Robert W., Jr. *Expert Opinion on Investigational Drugs* 2001, 10(8), 1423–1442.
100. Balzarini, J.; De Clercq, E. *Antiretroviral Therapy* 2001, 31–62.
101. E. De clercq *Journal of Clinical Virology*, 2001, 22, 73–89.
102. Merour, Jean-Yves; Joseph, Benoit. *Curr. Org. Chem.* (2001), 5(5), 471–506.
103. T. W. von Geldern et al. *J. Med. Chem* 1996, 39, 968.
104. M. Abdaoui et al. *Tetrahedron* 2000, 56, 2427.
105. W. J. Spillane et al. *J. Chem. Soc., Perkin Trans. 1*, 1982, 3, 677.
106. Wang, Tao; Wallace, Owen B.; Zhang, Zhongxing; Meanwell, Nicholas A.; Kadow, John F. Yin, Zhiwei. Composition and Antiviral Activity of Substituted Azaindoleoxoacetic Piperazine Derivatives. U.S. patent application Ser. No. 10/214,982 filed Aug. 7, 2002, which is a continuation-in-part application of U.S. Ser. No. 10/038, 306 filed Jan. 2, 2002 (corresponding to PCT Int. Appl. (PCT/US02/00455), WO 02/062423 A1, filed Jan. 2, 2002, published Aug. 15, 2002.

SUMMARY OF THE INVENTION

The present invention comprises compounds of Formula I, or pharmaceutically acceptable salts thereof, which are effective antiviral agents, particularly as inhibitors of HIV.

An embodiment of the invention are compounds of Formula I, including pharmaceutically acceptable salts thereof,

wherein:
Z is

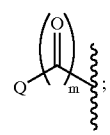

Q is selected from the group consisting of:

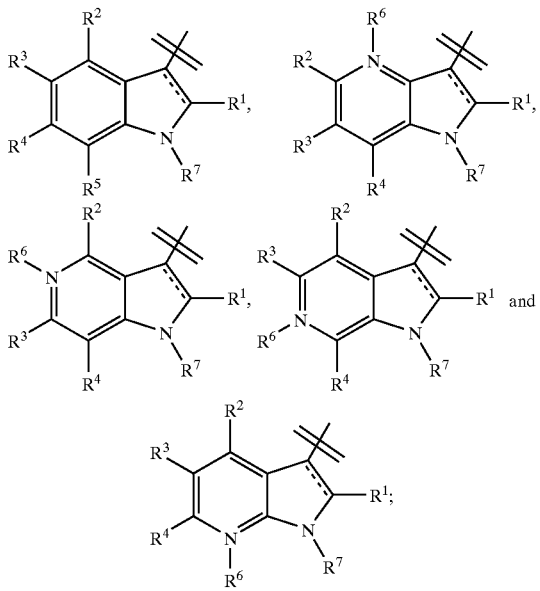

—W— is

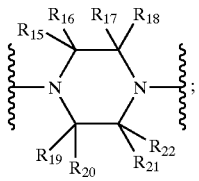

$R^1$, $R^2$, $R^3$, $R^4$, and $R^5$, are independently selected from the group consisting of hydrogen, halogen, cyano, nitro, $COOR^8$, $XR^9$ and B;
$R^{15}$, $R^{16}$, $R^{17}$, $R^{18}$, $R^{19}$, $R^{20}$, $R^{21}$ and $R^{22}$ are each independently H or $(C_{1-6})$alkyl; wherein $(C_{1-6})$alkyl is optionally substituted with one to three same or different members selected from the group consisting of halogen, amino, OH, CN and $NO_2$;

m is 1 or 2;

$R^6$ is O or does not exist;

$R^7$ is $(CH_2)_n R^{10}$, $SO_2NH_2$, $SO_2NHMe$ or $SO_2NMe_2$;

n is 0–6;

$R^{10}$ is selected from the group consisting of H, $(C_{1-6})$alkyl, —C(O)—$(C_{1-6})$alkyl, C(O)-phenyl and $CONR^{11}R^{12}$;

$R^{11}$ and $R^{12}$ are each independently H, $(C_{1-6})$alkyl or phenyl;

—represents a carbon-carbon bond or does not exist;

A is $NR^{13}R^{14}$;

$R^{13}$ and $R^{14}$ are independently selected from the group consisting of hydrogen, $(C_{1-6})$alkyl, $(C_{1-6})$alkenyl, $(C_{1-6})$alkynyl, $(C_{1-6})$alkoxy, $(C_{1-6})$cycloalkyl, phenyl, and heteroaryl; wherein said $(C_{1-6})$alkyl, phenyl and heteroaryl are independently optionally substituted with one to three same or different halogens or from one to three same or different substituents selected from F; or $R^{13}$ and $R^{14}$ taken together with the nitrogen atom to which they are attached forms a heteroalicyclic ring containing 3 to 6 atoms;

heteroalicyclic is selected from the group consisting of azetidinyl, piperidinyl, piperazinyl, pyrrolidinyl, morpholinyl, thiomorpholinyl, tetrahydrofuranyl and tetrahydropyranyl;

heteroaryl is selected from the group consisting of pyridinyl, pyrazinyl, pyridazinyl, pyrimidinyl, furanyl, thienyl, benzothienyl, thiazolyl, isothiazolyl, oxazolyl, benzooxazolyl, isoxazolyl, imidazolyl, benzoimidazolyl, 1H-imidazo[4,5-b]pyridin-2-yl, 1H-imidazo[4,5-c]pyridin-2-yl, oxadiazolyl, thiadiazolyl, pyrazolyl, tetrazolyl, tetrazinyl, triazinyl and triazolyl;

B is selected from the group consisting of $(C_{1-6})$alkyl, $(C_{3-6})$cycloalkyl, $C(O)NR^{23}R^{24}$, phenyl and heteroaryl; wherein said $(C_{1-6})$alkyl, phenyl and heteroaryl are independently optionally substituted with one to three same or different halogens or from one to three same or different substituents selected from F;

F is selected from the group consisting of $(C_{1-6})$alkyl, $(C_{3-6})$cycloalkyl cyano, phenyl, heteroaryl, heteroalicyclic, hydroxy, $(C_{1-6})$alkoxy, halogen, benzyl, —$NR^{25}C(O)$—$(C_{1-6})$alkyl, —$NR^{26}R^{27}$, morpholino, nitro, —$S(C_{1-6})$alkyl, —SPh, $NR^{25}S(O)_2$— $R^{26}$, piperazinyl, N-Me piperazinyl, C(O)H, $(CH2)_n COOR^{28}$ and —$CONR^{29}R^{30}$; wherein said $(C_{1-6})$alkyl, heteroaryl, or phenyl is optionally substituted with one to three same or different halogens or one to three methyl groups; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl; heteroalicyclic is selected from the group consisting of aziridinyl, azetidinyl, pyrrolidinyl, piperazinyl, N-methyl piperazinyl, piperidinyl, tetrahydrofuranyl, tetrahydropyranyl, azepinyl and morpholinyl;

$R^8$, $R^9$ and $R^{28}$ are independently selected from the group consisting of hydrogen and $(C_{1-6})$alkyl;

X is selected from the group consisting of $NR^{31}$, O and S;

$R^{23}$, $R^{24}$, $R^{25}$, $R^{26}$, $R^{27}$, $R^{29}$, $R^{30}$, $R^{31}$ are independently selected from the group consisting of hydrogen, $(C_{1-6})$alkyl, $(C_{1-6})$alkoxy, phenyl and heteroaryl; wherein said $(C_{1-6})$alkyl, phenyl, and heteroaryl are independently optionally substituted with one to three same or different group J; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl;

J is selected from the group consisting of $(C_{1-6})$alkyl, hydroxy, $(C_{1-6})$alkoxy, halogen, benzyl, —$NR^{32}C(O)$—$(C_{1-6})$alkyl, —$NR^{32}R^{33}$, —$S(C_{1-6})$alkyl, —SPh, $(CH2)_n COOR^{28}$ and —$CONR^{32}R^{33}$; wherein said $(C_{1-6})$alkyl is optionally substituted with one to three same or different halogens; and $R^{32}$ and $R^{33}$ are independently selected from the group consisting of hydrogen and $(C_{1-6})$alkyl; wherein said $(C_{1-6})$alkyl is optionally substituted with one to three same or different halogen, methyl, or $CF_3$ groups.

A preferred embodiment of the invention are compounds of Formula I, as above including pharmaceutically acceptable salts thereof, Z is

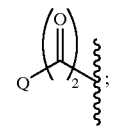

$R^1$ is hydrogen;

—represents a carbon-carbon bond; and $R^6$ does not exist.

Another preferred embodiment of the invention are compounds of Formula I, as above including pharmaceutically acceptable salts thereof, $R^7$ is hydrogen; and $R^{15}$, $R^{16}$, $R^{17}$, $R^{18}$, $R^{19}$, $R^{20}$, $R^{21}$, $R^{22}$ are each independently H or methyl with the proviso that a maximum of one of $R^{15}$–$R^{22}$ is methyl.

Another preferred embodiment of the invention are compounds of Formula I, as above including pharmaceutically acceptable salts thereof, Q is a member selected from groups (A) and (B) consisting of:

(A)

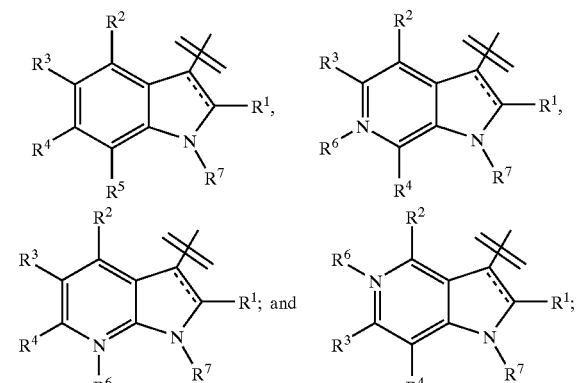

provided $R^2$ and $R^3$ are each independently hydrogen, methoxy or halogen; and

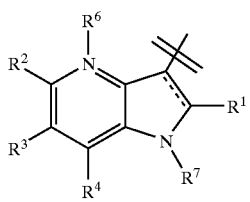

(B)

provided R² is hydrogen, methoxy or halogen.

Another preferred embodiment of the invention are compounds of Formula I, as above including pharmaceutically acceptable salts thereof, wherein B is selected from the group consisting of —C(O)NR²³R²⁴, phenyl and heteroaryl; wherein said phenyl or heteroaryl is optionally substituted with one to three same or different halogens or from one to two same or different substituents selected from the group F.

Another preferred embodiment of the invention are compounds of Formula I, as above including pharmaceutically acceptable salts thereof, wherein A is selected from the group consisting of —NH(C₁–C₆alkyl), —N(C₁–C₆alkyl)₂, -NHfuryl, -NHPh, morpholinyl, N-Me piperazinyl, —N(—CH₂—)₃, —N(—CH₂—)₄, —N(—CH₂—)₅, and pyrazolyl.

Another preferred embodiment of the invention are compounds of Formula I, as above including pharmaceutically acceptable salts thereof, wherein B is —C(O)NHMe or —C(O)NH-heteroaryl; wherein said heteroaryl is optionally substituted with one to two substituents selected from the group consisting of halogen, (C₁–C₆ alkyl), amino, —NHC(O)—(C₁–C₆ alkyl), -methoxy, —COOH, —CH₂COOH, —CH₂CH₂COOH, —NH(C₁–C₆ alkyl) and —N(C₁–C₆ alkyl)₂.

Another preferred embodiment of the invention are compounds of Formula I, as above including pharmaceutically acceptable salts thereof, wherein A is selected from the group consisting of —NH(C₁–C₆alkyl), —N(C₁–C₆alkyl)₂, -NHfuryl, -NHPh, morpholinyl, N-Me piperazinyl, —N(—CH₂—)₃, —N(—CH₂—)₄, —N(—CH₂—)₅, and pyrazolyl; and B is -triazolyl or pyrazolyl which is optionally substituted with one to two substituents selected from the group consisting of halogen, (C₁–C₆ alkyl), amino, —NHC(O)—(C₁–C₆ alkyl), -methoxy, —COOH, —CH₂COOH, —CH₂CH₂COOH, —NH(C₁–C₆ alkyl) and —N(C₁–C₆ alkyl)₂.

Another preferred embodiment of the invention are compounds of Formula I, including pharmaceutically acceptable salts thereof, wherein the compound is selected from Examples 1–14.

Another embodiment of the present invention is a method for treating mammals infected with a virus, wherein said virus is optionally HIV, comprising administering to said mammal an antiviral effective amount of a compound of Formula I, including pharmaceutically acceptable salts thereof, and one or more pharmaceutically acceptable carriers, excipients or diluents; optionally the compound of Formula I can be administered in combination with an antiviral effective amount of an AIDS treatment agent selected from the group consisting of: (a) an AIDS antiviral agent; (b) an anti-infective agent; (c) an immunomodulator; and (d) HIV entry inhibitors.

Another embodiment of the present invention is a pharmaceutical composition comprising an antiviral effective amount of a compound of Formula I, including pharmaceutically acceptable salts thereof, and one or more pharmaceutically acceptable carriers, excipients, diluents and optionally in combination with an antiviral effective amount of an AIDS treatment agent selected from the group consisting of: (a) an AIDS antiviral agent; (b) an anti-infective agent; (c) an immunomodulator; and (d) HIV entry inhibitors.

DETAILED DESCRIPTION OF THE INVENTION

Since the compounds of the present invention, may possess asymmetric centers and therefore occur as mixtures of diastereomers and enantiomers, the present invention includes the individual diastereoisomeric and enantiomeric forms of the compounds of Formula I in addition to the mixtures thereof.

Definitions

Unless otherwise indicated, the following definitions apply.

The term "$C_{1-6}$ alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"Ph" means phenyl.

"Halogen" refers to chlorine, bromine, iodine or fluorine.

An "aryl" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl. The aryl group may be substituted or unsubstituted. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —NR$^x$R$^y$, wherein R$^x$ and R$^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl, diazinyl, pyrazine, triazinyltriazine, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —NR$^x$R$^y$, wherein R$^x$ and R$^y$ are as defined above.

As used herein, a "heteroalicyclic" group refers to a monocyclic or fused 3–8 membered-ring group, preferably 3–6 membered-ring group, having in the ring(s) one or more atoms selected from the group consisting of nitrogen, oxygen and sulfur. Rings are selected from those which provide stable arrangements of bonds and are not intended to encomplish systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —NR$^x$R$^y$, wherein R$^x$ and R$^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1–20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalo-methanesulfonamido, trihalomethanesulfonyl, silyl, guanyl, guanidino, ureido, phosphonyl, amino and —NR$^x$R$^y$ with R$^x$ and R$^y$ as defined above.

An "alkenyl" group refers to an alkyl group, as defined herein, consisting of at least two carbon atoms and at least one carbon-carbon double bond.

An "alkynyl" group refers to an alkyl group, as defined herein, consisting of at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "Keto" group refers to a —CC(=O)C— group wherein the carbon on either or both sides of the C=O may be alkyl, cycloalkyl, aryl or a carbon of a heteroaryl or heteroaliacyclic group.

A "trihalomethanecarbonyl" group refers to a Z$_3$CC(=O)— group with said Z being a halogen.

A "C-carboxy" group refers to a —C(=O)O—R" groups, with R" as defined herein.

An "O-carboxy" group refers to a R"C(=O)O-group, with R" as defined herein.

A "carboxylic acid" group refers to a C-carboxy group in which R" is hydrogen.

A "trihalomethyl" group refers to a —CZ$_3$, group wherein Z is a halogen group as defined herein.

A "trihalomethanesulfonyl" group refers to an Z$_3$CS(=O)$_2$— groups with Z as defined above.

A "trihalomethanesulfonamido" group refers to a Z$_3$CS(=O)$_2$NR$^x$— group with Z and R$^x$ as defined herein.

A "sulfinyl" group refers to a —S(=O)—R" group, with R" as defined herein and, in addition, as a bond only; i.e., —S(O)—.

A "sulfonyl" group refers to a —S(=O)$_2$R" group with R" as defined herein and, in addition as a bond only; i.e., —S(O)$_2$—.

A "S-sulfonamido" group refers to a —S(=O)$_2$NR$^X$R$^Y$, with R$^x$ and R$^Y$ as defined herein.

A "N-Sulfonamido" group refers to a R"S(=O)$_2$NR$_x$— group with R$_x$ as defined herein.

A "O-carbamyl" group refers to a —OC(=O)NR$^x$R$^y$ as defined herein.

A "N-carbamyl" group refers to a R$^x$OC(=O)NR$^y$ group, with R$^x$ and R$^y$ as defined herein.

A "O-thiocarbamyl" group refers to a —OC(=S)NR$^x$R$^y$ group with R$^x$ and R$^y$ as defined herein.

A "N-thiocarbamyl" group refers to a R$^x$OC(=S)NR$^y$— group with R$^x$ and R$^y$ as defined herein.

An "amino" group refers to an —NH$_2$ group.

A "C-amido" group refers to a —C(=O)NR$^x$R$^y$ group with R$^x$ and R$^y$ as defined herein.

A "C-thioamido" group refers to a —C(=S)NR$^x$R$^y$ group, with R$^x$ and R$^y$ as defined herein.

A "N-amido" group refers to a R$^x$C(=O)NR$^y$— group, with R$^x$ and R$^y$ as defined herein.

An "ureido" group refers to a —NR$^x$C(=O)NR$^y$R$^{y2}$ group with R$^x$ and R$^y$ as defined herein and R$^{y2}$ defined the same as R$^x$ and R$^y$.

A "guanidino" group refers to a —R$^x$NC(=N)NR$^y$R$^{y2}$ group, with R$^x$, R$^y$ and R$^{y2}$ as defined herein.

A "guanyl" group refers to a R$^x$R$^y$NC(=N)— group, with R$^x$ and R$^Y$ as defined herein.

A "cyano" group refers to a —CN group.

A "silyl" group refers to a —Si(R")$_3$, with R" as defined herein.

A "phosphonyl" group refers to a P(=O)(OR$^x$)$_2$ with R$^x$ as defined herein.

A "hydrazino" group refers to a —NR$^x$NR$^y$R$^{y2}$ group with R$^x$, R$^y$ and R$^{y2}$ as defined herein.

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present invention are based on the known general principles of chemical bonding. It is understood that the claims do not encompass structures known to be unstable or not able to exist based on the literature.

Physiologically acceptable salts and prodrugs of compounds disclosed herein are within the scope of this invention. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

In the method of the present invention, the term "antiviral effective amount" means the total amount of each active component of the method that is sufficient to show a meaningful patient benefit, i.e., healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with HIV infection.

The present invention is also directed to combinations of the compounds with one or more agents useful in the treatment of AIDS. For example, the compounds of this invention may be effectively administered, whether at periods of pre-exposure and/or post-exposure, in combination with effective amounts of the AIDS antivirals, immunomodulators, antiinfectives, or vaccines, such as those in the following table.

| Drug Name | Manufacturer | Indication |
|---|---|---|
| ANTIVIRALS | | |
| 097 | Hoechst/Bayer | HIV infection, AIDS, ARC (non-nucleoside reverse transcriptase (RT) inhibitor) |
| Amprenivir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated Diseases |
| BMS-232623 (CGP-73547) | Bristol-Myers Squibb/ Novartis | HIV infection, AIDS, ARC (protease inhibitor) |
| BMS-234475 | Bristol-Myers Squibb/ | HIV infection, |

-continued

| Drug Name | Manufacturer | Indication |
|---|---|---|
| (CGP-61755) | Novartis | AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266) (−)6-Chloro-4-(S)-cyclopropylethynyl-4(S)-trifluoro-methyl-1,4-dihydro-2H-3,1-benzoxazin-2-one, STOCRINE | DuPont Merck | HIV infection, AIDS, ARC (non-nucleoside RT inhibitor) |
| EL10 | Elan Corp, PLC (Gainesville, GA) | HIV infection |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |

-continued

| Drug Name | Manufacturer | Indication |
|---|---|---|
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) | Gilead | HIV infection, AIDS, (reverse transcriptase inhibitor) |
| Combivir ® | GSK | HIV infection, AIDS, (reverse transcriptase inhibitor) |
| abacavir succinate (or Ziagen ®) | GSK | HIV infection, AIDS, (reverse transcriptase inhibitor) |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 | Hoffman-LaRoche | AIDS, ARC, HIV, in |

-continued

| Drug Name | Manufacturer | Indication |
|---|---|---|
| Interleukin-2 | Immunex | combination w/AZT |
| IL-2 | Chiron | AIDS, increase in |
| Interleukin-2 | | CD4 cell counts |
| (aldeslukin) | | |
| Immune Globulin | Cutter Biological | Pediatric AIDS, in |
| Intravenous | (Berkeley, CA) | combination w/AZT |
| (human) | | |
| IMREG-1 | Imreg | AIDS, Kaposi's |
| | (New Orleans, LA) | sarcoma, ARC, PGL |
| IMREG-2 | Imreg | AIDS, Kaposi's |
| | (New Orleans, LA) | sarcoma, ARC, PGL |
| Imuthiol Diethyl | Merieux Institute | AIDS, ARC |
| Dithio Carbamate | | |
| Alpha-2 | Schering Plough | Kaposi's sarcoma |
| Interferon | | w/AZT, AIDS |
| Methionine- | TNI Pharmaceutical | AIDS, ARC |
| Enkephalin | (Chicago, IL) | |
| MTP-PE | Ciba-Geigy Corp. | Kaposi's sarcoma |
| Muramyl-Tripeptide | | |
| Granulocyte | Amgen | AIDS, in combination |
| Colony Stimulating | | w/AZT |
| Factor | | |
| Remune | Immune Response | Immunotherapeutic |
| | Corp. | |
| rCD4 | Genentech | AIDS, ARC |
| Recombinant | | |
| Soluble Human CD4 | | |
| rCD4-IgG | | AIDS, ARC |
| hybrids | | |
| Recombinant | Biogen | AIDS, ARC |
| Soluble Human CD4 | | |
| Interferon | Hoffman-La Roche | Kaposi's sarcoma |
| Alfa 2a | | AIDS, ARC, |
| | | in combination w/AZT |
| SK&F106528 | Smith Kline | HIV infection |
| Soluble T4 | | |
| Thymopentin | Immunobiology | HIV infection |
| | Research Institute | |
| | (Annandale, NJ) | |
| Tumor Necrosis | Genentech | ARC, in combination |
| Factor; TNF | | w/gamma Interferon |
| ANTI-INFECTIVES | | |
| Clindamycin with | Pharmacia Upjohn | PCP |
| Primaquine | | |
| Fluconazole | Pfizer | Cryptococcal |
| | | meningitis, |
| | | candidiasis |
| Pastille | Squibb Corp. | Prevention of |
| Nystatin Pastille | | oral candidiasis |
| Ornidyl | Merrell Dow | PCP |
| Eflornithine | | |
| Pentamidine | LyphoMed | PCP treatment |
| Isethionate (IM & IV) | (Rosemont, IL) | |
| Trimethoprim | | Antibacterial |
| Trimethoprim/sulfa | | Antibacterial |
| Piritrexim | Burroughs Wellcome | PCP treatment |
| Pentamidine | Fisons Corporation | PCP prophylaxis |
| Isethionate for | | |
| Inhalation | | |
| Spiramycin | Rhone-Poulenc | Cryptosporidial |
| | | diarrhea |
| Intraconazole- | Janssen-Pharm. | Histoplasmosis; |
| R51211 | | cryptococcal |
| | | meningitis |
| Trimetrexate | Warner-Lambert | PCP |
| Daunorubicin | NeXstar, Sequus | Kaposi's sarcoma |
| Recombinant Human | Ortho Pharm. Corp. | Severe anemia |
| Erythropoietin | | assoc. with AZT |
| | | therapy |
| Recombinant Human | Serono | AIDS-related |
| Growth Hormone | | wasting, cachexia |
| Megestrol Acetate | Bristol-Myers Squibb | Treatment of |
| | | anorexia assoc. |
| | | W/AIDS |
| Testosterone | Alza, Smith Kline | AIDS-related wasting |
| Total Enteral | Norwich Eaton | Diarrhea and |

-continued

| Drug Name | Manufacturer | Indication |
|---|---|---|
| Nutrition | Pharmaceuticals | malabsorption related to AIDS |

Additionally, the compounds of the invention herein may be used in combination with another class of agents for treating AIDS which are called HIV entry inhibitors. Examples of such HIV entry inhibitors are discussed in DRUGS OF THE FUTURE 1999, 24(12), pp. 1355–1362; CELL, Vol. 9, pp. 243–246, Oct. 29, 1999; and DRUG DISCOVERY TODAY, Vol. 5, No. 5, May 2000, pp. 183–194.

It will be understood that the scope of combinations of the compounds of this invention with AIDS antivirals, immunomodulators, anti-infectives, HIV entry inhibitors or vaccines is not limited to the list in the above Table, but includes in principle any combination with any pharmaceutical composition useful for the treatment of AIDS.

Preferred combinations are simultaneous or alternating treatments of with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2(S)-N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

In such combinations the compound of the present invention and other active agents may be administered separately or in conjunction. In addition, the administration of one element may be prior to, concurrent to, or subsequent to the administration of other agent(s).

Abbreviations

The following abbreviations, most of which are conventional abbreviations well known to those skilled in the art, are used throughout the description of the invention and the examples. Some of the abbreviations used are as follows:

| | |
|---|---|
| h = | hour(s) |
| rt = | room temperature |
| mol = | mole(s) |

-continued

| | |
|---|---|
| mmol = | millimole(s) |
| g = | gram(s) |
| mg = | milligram(s) |
| mL = | milliliter(s) |
| TFA = | Trifluoroacetic Acid |
| DCE = | 1,2-Dichloroethane |
| $CH_2Cl_2$ = | Dichloromethane |
| TPAP = | tetrapropylammonium perruthenate |
| THF = | Tetrahydofuran |
| DEPBT = | 3-(Diethoxyphosphoryloxy)-1,2,3-benzotriazin-4(3H)-one |
| DMAP = | 4-dimethylaminopyridine |
| P-EDC = | Polymer supported 1-(3-dimethylaminopropyl)-3-ethylcarbodiimide |
| EDC = | 1-(3-dimethylaminopropyl)-3-ethylcarbodiimide |
| DMF = | N,N-dimethylformamide |
| Hunig's Base = | N,N-Diisopropylethylamine |
| mCPBA = | meta-Chloroperbenzoic Acid |
| azaindole = | 1H-Pyrrolo-pyridine |
| 4-azaindole = | 1H-pyrrolo[3,2-b]pyridine |
| 5-azaindole = | 1H-Pyrrolo[3,2-c]pyridine |
| 6-azaindole = | 1H-pyrrolo[2,3-c]pyridine |
| 7-azaindole = | 1H-Pyrrolo[2,3-b]pyridine |
| PMB = | 4-Methoxybenzyl |
| DDQ = | 2,3-Dichloro-5,6-dicyano-1,4-benzoquinone |
| OTf = | Trifluoromethanesulfonoxy |
| NMM = | 4-Methylmorpholine |
| PIP-COPh = | 1-Benzoylpiperazine |
| NaHMDS = | Sodium hexamethyldisilazide |
| EDAC = | 1-(3-Dimethylaminopropyl)-3-ethylcarbodiimide |
| TMS = | Trimethylsilyl |
| DCM = | Dichloromethane |
| DCE = | Dichloroethane |
| MeOH = | Methanol |
| THF = | Tetrahydrofuran |
| EtOAc = | Ethyl Acetate |
| LDA = | Lithium diisopropylamide |
| TMP-Li = | 2,2,6,6-tetramethylpiperidinyl lithium |
| DME = | Dimethoxyethane |
| DIBALH = | Diisobutylaluminum hydride |
| HOBT = | 1-hydroxybenzotriazole |
| CBZ = | Benzyloxycarbonyl |
| PCC = | Pyridinium chlorochromate |

The general synthesis procedures for making the novel indoleoxoacetic sulfonylureido piperazine containing analogs of Formula I of the invention herein are described below.

Scheme A

Sulfamoylation of compounds of formula Z-W—H can be achieved using a sulfamoyl chloride (2–3 eq.) in the presence of a tertiary amine (3–10 eq.) such as triethylamine or diisopropylethylamine in an anhydrous aprotic solvent such as THF, acetonitrile or DMF at temperatures ranging from 0° C. to 25° C. to give compounds of formula I. The reaction can be monitored by LC/MS. The sulfamoyl chlorides can be purchased or easily prepared from sulfamic acids or amines following literature procedures. (See for example: T. W. von Geldern et al. J. Med. Chem 1996, 39, 968; M. Abdaoui et al. Tetrahedron 2000, 56, 2427; W. J. Spillane et al. J. Chem. Soc., Perkin Trans. 1, 1982, 3, 677).

Scheme AA

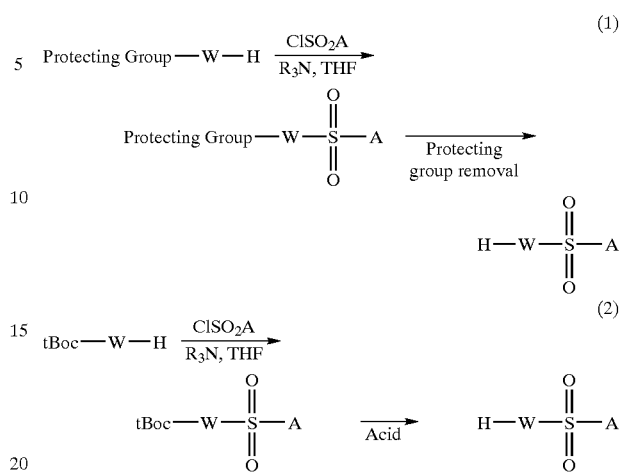

As shown in Scheme AA, H—W—$SO_2$-A can be prepared using similar methodology except that Z is replaced by a protecting group such as Boc. Removal of the protecting group under standard conditions for protecting group material such as aq HCL or TFA as in the case of Boc generates H—W—$SO_2$-A which are ready for coupling as described in Step D below.

Procedures for making Z (as defined in formula I of the description of the invention) are described in the Blair, Wang, Wallace, or Wang references 93–95 and 106 respectively. The entire disclosures in U.S. Pat. No. 6,469,006 granted Oct. 22, 2002; U.S. Pat. No. 6,476,034 granted Nov. 5, 2002; U.S. Pat. No. 6,573,262 granted Jun. 3, 2003 (corresponding to PCT WO 02/04440, published Jan. 17, 2002); and U.S. patent application Ser. No. 10/214,982 filed Aug. 7, 2002, which is a continuation-in-part of U.S. Ser. No. 10/038,306 filed Jan. 2, 2002 (corresponding to PCT WO 02/62423 published Aug. 15, 2002) are incorporated by reference herein. Additional general procedures to construct substituted azaindole Q and Z of Formula I and intermediates useful for their synthesis are described in the following Schemes.

Scheme 1

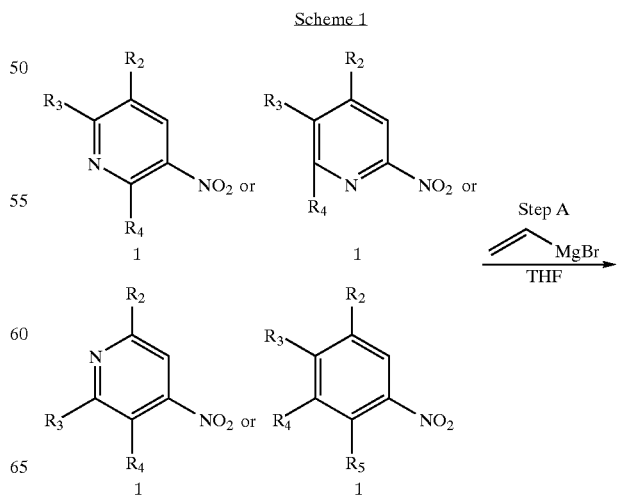

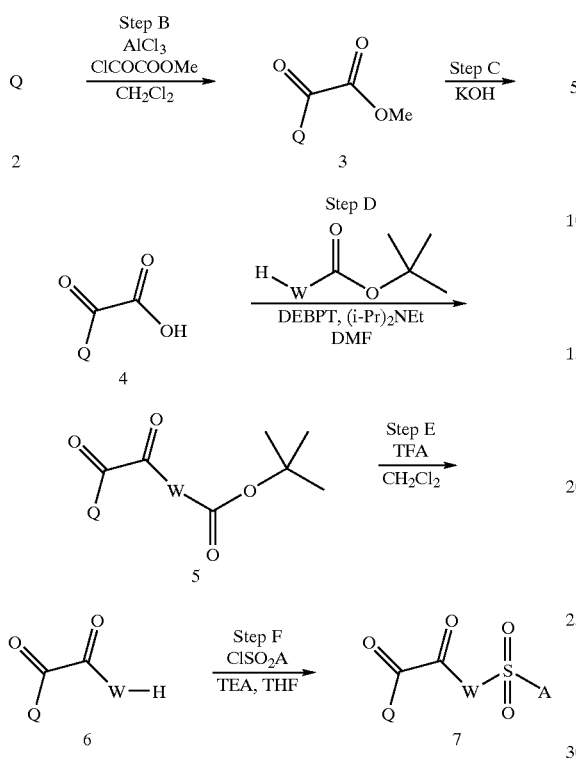
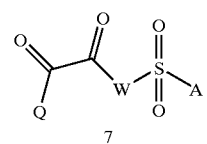
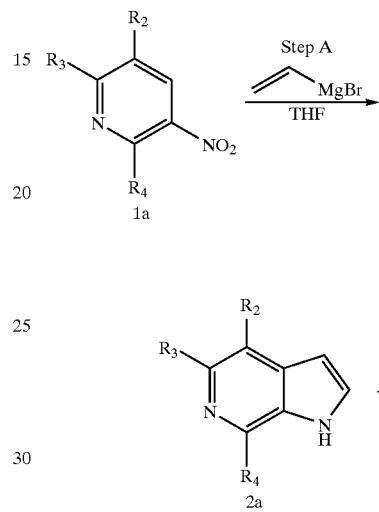
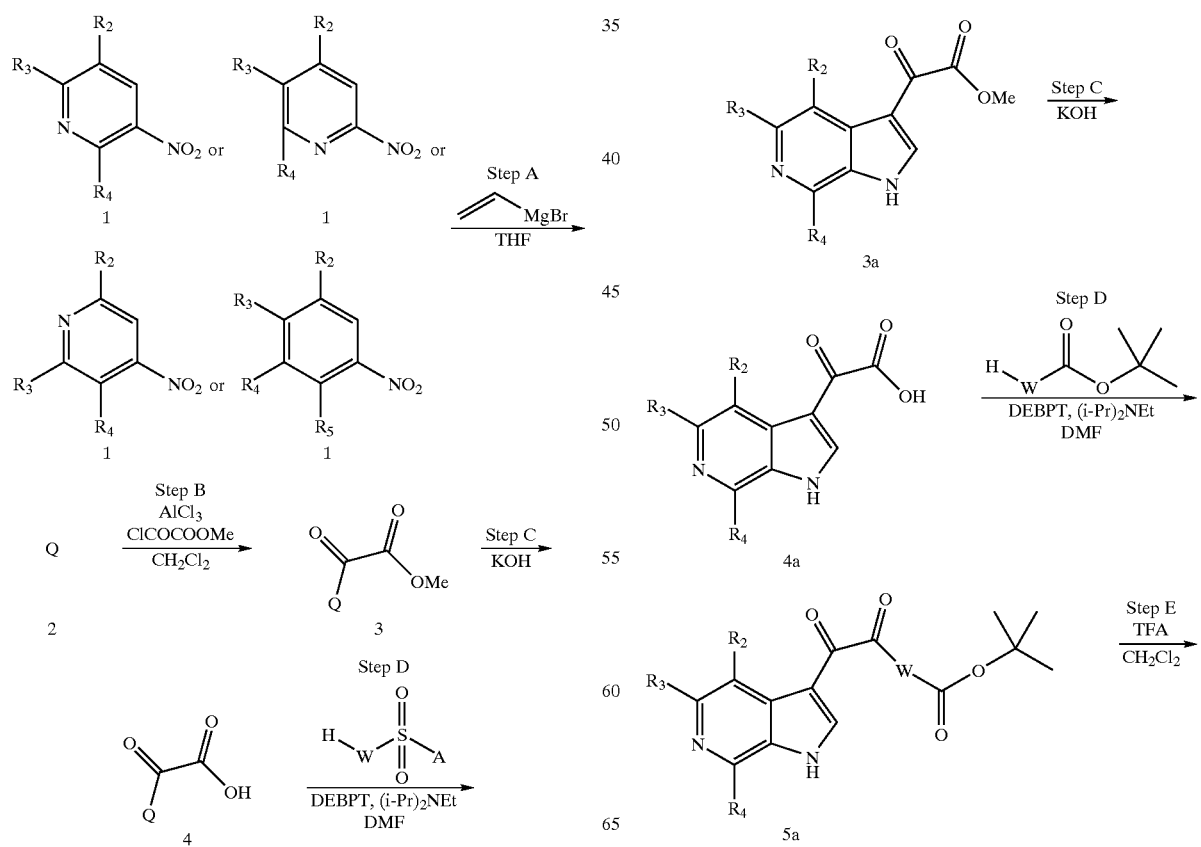

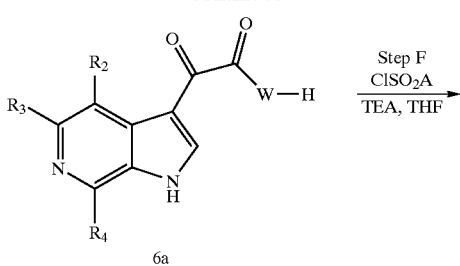
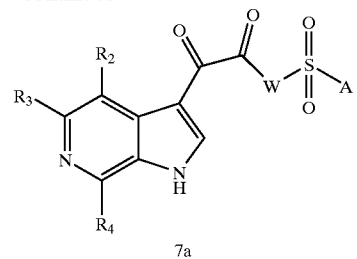
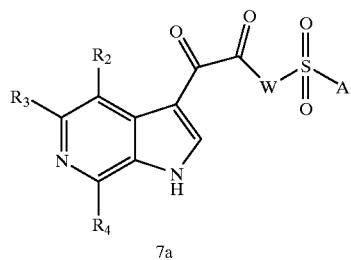
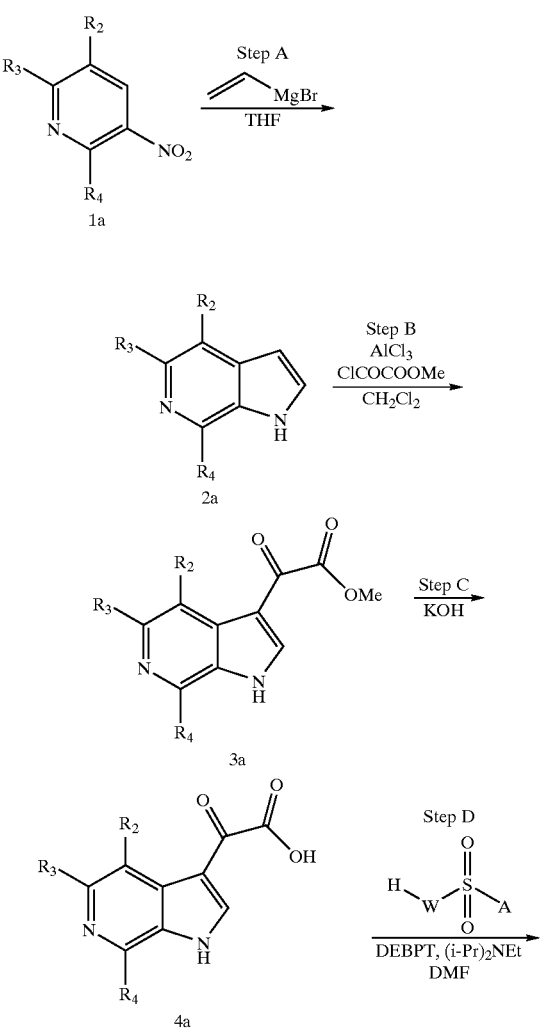

Step A in Schemes 1,1a,1b,1c, or 1f depicts the synthesis of either an aza indole or indole intermediate, 2 or 2a–2e via the well known Bartoli reaction in which vinyl magnesium bromide reacts with an aryl or heteroaryl nitro group, such as in 1, to form a five-membered nitrogen containing ring as shown. Some references for the above transformation include: Bartoli et al. a) *Tetrahedron Lett.* 1989, 30, 2129. b) *J. Chem. Soc. Perkin Trans. I* 1991, 2757. c) *J. Chem. Soc. Perkin Trans. II* 1991, 657. d) Synthesis (1999), 1594. In the preferred procedure, a solution of vinyl Magnesium bromide in THF (typically 1.0M but from 0.25 to 3.0M) is added dropwise to a solution of the nitro pyridine in THF at −78° under an inert atmosphere of either nitrogen or Argon. After addition is completed, the reaction temperature is allowed to warm to −20° and then is stirred for approximately 12 h before quenching with 20% aq ammonium chloride solution. The reaction is extracted with ethyl acetate and then worked up in a typical manner using a drying agent such as anhydrous magnesium sulfate or sodium sulfate. Products are generally purified using chromatography over Silica gel. Best results are generally achieved using freshly prepared vinyl Magnesium bromide. In some cases, vinyl Magnesium chloride may be substituted for vinyl Magnesium bromide.

Substituted azaindoles may be prepared by methods described in the literature or may be available from commercial sources. Thus there are many methods for carrying out step A in the literature and the specific examples are too numerous to even list. A review on the synthesis of 7-azaindoles has been published (Merour et. al. reference 102). Alternative syntheses of aza indoles and general methods for carrying out step A include, but are not limited to, those described in the following references (a–k below): a) Prokopov, A. A.; Yakhontov, L. N. *Khim.-Farm. Zh.* 1994, 28(7), 30–51; b) Lablache-Combier, A. Heteroaromatics. Photoinduced Electron Transfer 1988, Pt. C, 134–312; c) Saify, Zafar Said. *Pak. J. Pharmacol.* 1986, 2(2), 43–6; d) Bisagni, E. *Jerusalem Symp. Quantum Chem. Biochem.* 1972, 4, 439–45; e) Yakhontov, L. N. *Usp. Khim.* 1968, 37(7), 1258–87; f) Willette, R. E. *Advan. Heterocycl. Chem.* 1968, 9, 27–105; g) Mahadevan, I.; Rasmussen, M. *Tetrahedron* 1993, 49(33), 7337–52; h) Mahadevan, I.; Rasmussen, M. *J. Heterocycl. Chem.* 1992, 29(2), 359–67; i) Spivey, A. C.; Fekner, T.; Spey, S. E.; Adams, H. *J. Org. Chem.* 1999, 64(26), 9430–9443; j) Spivey, A. C.; Fekner, T.; Adams, H. *Tetrahedron Lett.* 1998, 39(48), 8919–8922; k) Advances in Heterocyclic Chemistry (Academic press) 1991, Vol. 52, pg 235–236 and references therein.

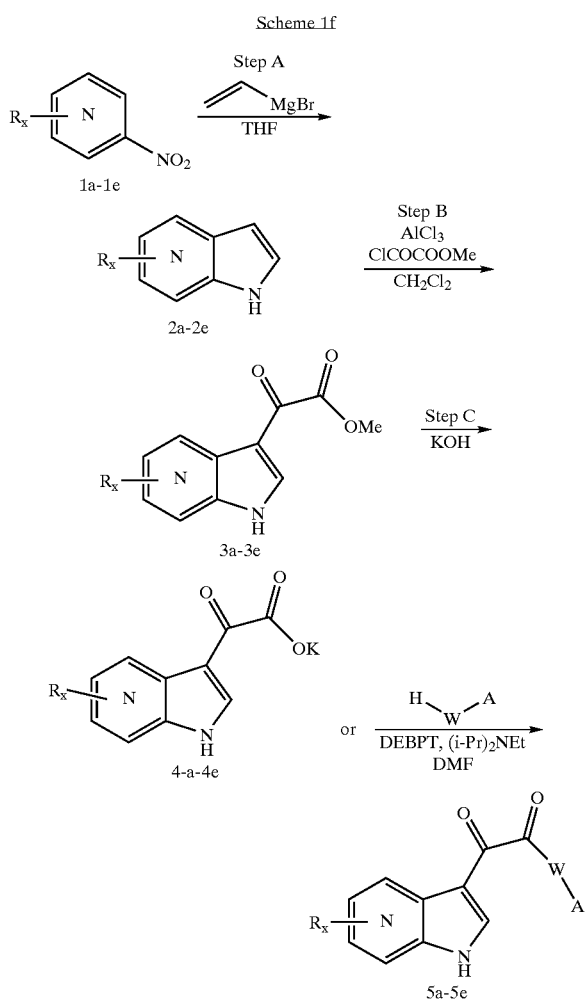

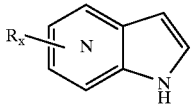

$R_x$=$R_2$–$R_4$ for azaindoles or $R_2$–$R_5$ for indoles

=Q (most generic definition unless specified except for caveats $R_6$ is nothing R2 is not depicted (in the interest of convenience) but is considered hydrogen. Other $R_2$ groups would work similarly in these tranformations within reactivity limits of a chemist skilled in the art.

$R_7$ is Hydrogen

Scheme 1f depicts a shorthand method for representing the intermediates used for reactions in Schemes 1a–1c, and Schemes 2–7 and generic Q. It is understood, for the purposes of Scheme 1f and further Schemes, that 1b is used to synthesize 2b–5b, 1c provides 2c–5c and 1d provides 2d–5d etc. The substituents $R_x$ represent for azaindoles $R_2$–$R_4$ and for indoles $R_2$–$R_5$. In formulas in following schemes, one of the substituents may be depicted but it is understood that each formual can represent the appropriate generic azaindoles or indole in order to keep the application succinct.

Step B. Intermediates 3 can be prepared by reaction of indole or aza-indole, intermediate 2, with an excess of ClCOCOOMe in the presence of $AlCl_3$ (aluminum chloride) (Sycheva et al, Ref. 26, Sycheva, T. V.; Rubtsov, N. M.; Sheinker, Yu. N.; Yakhontov, L. N. Some reactions of 5-cyano-6-chloro-7-azaindoles and lactam-lactim tautomerism in 5-cyano-6-hydroxy-7-azaindolines. *Khim. Geterotsikl. Soedin.*, 1987, 100–106). Typically an inert solvent such as $CH_2Cl_2$ is used but others such as THF, $Et_2O$, DCE, dioxane, benzene, or toluene may find applicability either alone or in mixtures. Other oxalate esters such as ethyl or benzyl mono esters of oxalic acid could also suffice for either method shown above. More lipophilic esters ease isolation during aqueous extractions. Phenolic or substituted phenolic (such as pentafluorophenol) esters enable direct coupling of the HW-protecting group, such as a Boc-piperazine, in Step D without activation. Lewis acid catalysts, such as tin tetrachloride, titanium IV chloride, and aluminum chloride are employed in Step B with aluminum chloride being most preferred. Alternatively, the azaindole is treated with a Grignard reagent such as MeMgI (methyl magnesium iodide), methyl magnesium bromide or ethyl magnesium bromide and a zinc halide, such as $ZnCl_2$ (zinc chloride) or zinc bromide, followed by the addition of an oxalyl chloride mono ester, such as ClCOCOOMe (methyl chlorooxoacetate) or another ester as above, to afford the aza-indole glyoxyl ester (Shadrina et al, Ref. 25). Oxalic acid esters such as methyl oxalate, ethyl oxalate or as above are used. Aprotic solvents such as $CH_2Cl_2$, $Et_2O$, benzene, toluene, DCE, or the like may be used alone or in combination for this sequence. In addition to the oxalyl chloride mono esters, oxalyl chloride itself may be reacted with the azaindole and then further reacted with an appropriate amine, such as a piperazine derivative.

Step C. Hydrolysis of the methyl ester, (intermediate 3a, Scheme 1) affords a potassium salt of intermediate 4a, which is coupled with protected piperazine derivatives, such as BOC-piperazine, as shown in Step D of Scheme 1. Some typical conditions employ methanolic or ethanolic sodium hydroxide followed by careful acidification with aqueous hydrochloric acid of varying molarity but 1M HCl is preferred. The acidification is not utilized in many cases as described above for the preferred conditions. Lithium hydroxide or potassium hydroxide could also be employed and varying amounts of water could be added to the alcohols. Propanols or butanols could also be used as solvents. Elevated temperatures up to the boiling points of the solvents may be utilized if ambient temperatures do not suffice. Alternatively, the hydrolysis may be carried out in a non polar solvent such as $CH_2Cl_2$ or THF in the presence of Triton B. Temperatures of –78° C. to the boiling point of the solvent may be employed but –10° C. is preferred. Other conditions for ester hydrolysis are listed in reference 41 and both this reference and many of the conditions for ester hydrolysis are well known to chemists of average skill in the art.

Alternative Procedures for Step B and C:

Imidazolium Chloroaluminate:

We found that ionic liquid 1-alkyl-3-alkylimidazolium chloroaluminate is generally useful in promoting the Friedel-Crafts type acylation of indoles and azaindoles. The ionic liquid is generated by mixing 1-alkyl-3-alkylimidazolium chloride with aluminium chloride at room temperature with vigorous stirring. 1:2 or 1:3 molar ratio of 1-alkyl-3-alkylimidazolium chloride to aluminium chloride is preferred. One particular useful imidazolium chloroaluminate for the acylation of azaindole with methyl or ethyl chlorooxoacetate is the 1-ethyl-3-methylimidazolium chloroaluminate. The reaction is typically performed at ambient temperature and the azaindoleglyoxyl ester can be isolated. More conveniently, we found that the glyoxyl ester can be hydrolyzed in situ at ambient temperature on prolonged reaction time (typically overnight) to give the corresponding glyoxyl acid (intermediate 4a) for amide formation (Scheme 2).

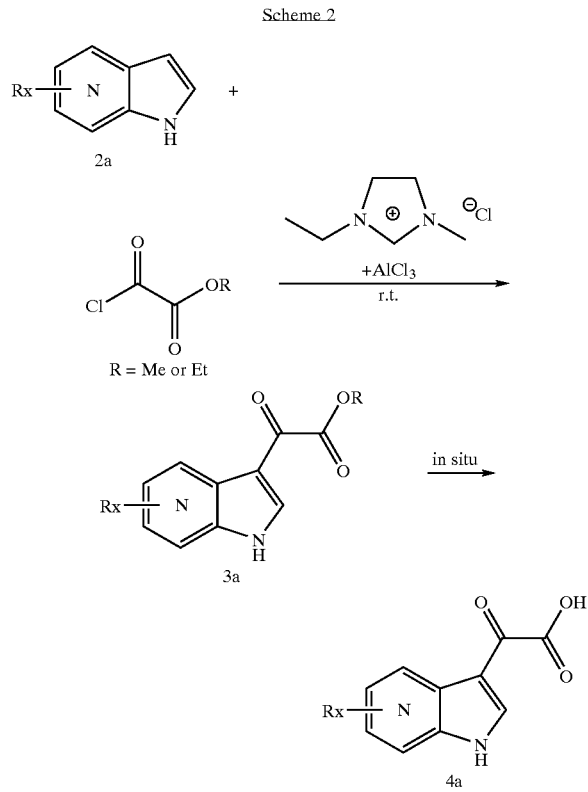

Scheme 2

A representative experimental procedure is as follows: 1-ethyl-3-methylimidazolium chloride (2 equiv.; purchased from TCI; weighted under a stream of nitrogen) was stirred in an oven-dried round bottom flask at r.t. under a nitrogen atmosphere, and added aluminium chloride (6 equiv.; anhydrous powder packaged under argon in ampules purchased from Aldrich preferred; weighted under a stream of nitrogen). The mixture was vigorously stirred to form a liquid, which was then added azaindole (1 equiv.) and stirred until a homogenous mixture resulted. The reaction mixture was added dropwise ethyl or methyl chlorooxoacetate (2 equiv.) and then stirred at r.t. for 16 h. After which time, the mixture was cooled in an ice-water bath and the reaction quenched by carefully adding excess water. The precipitates were filtered, washed with water and dried under high vacuum to give the azaindoleglyoxylic acid. For some examples, 3 equivalents of 1-ethyl-3-methylimidazolium chloride and chlorooxoacetate may be required.

Related references: (1) Welton, T. *Chem Rev.* 1999, 99, 2071; (2) Surette, J. K. D.; Green, L.; Singer, R. D. *Chem. Commun.* 1996, 2753; (3) Saleh, R. Y. WO 0015594.

Step D. The acid intermediates QC(O)C(O)OH (which can also be depicted as Z-OH) or 4a, from step C of Scheme 1, 1a, 1b, or 1c respectively is coupled with either as shown in Scheme 1 and 1b, a protected piperazine, for example t-butyl 1-piperazinecarboxylate (Boc-piperazine), or as shown in Scheme 1a and 1c, intermediate H—W—SO$_2$-A (where W corresponds to claim 1 and H is hydrogen) can be coupled with the acid using standard amide bond or peptide bond forming coupling reagents. The combination of EDAC and triethylamine in tetrahydrofuran or BOPCl and diisopropyl ethyl amine in chloroform have been utilized most frequently but DEPBT, or other coupling reagents such as PyBop could be utilized. Another useful coupling condition employs HATU (L. A. Carpino et. al. J. Chem. Soc. Chem Comm. 1994, 201–203; A. Virgilio et. al. J. Am. Chem. Soc. 1994, 116, 11580–11581). A general procedure for using this reagent is Acid (1 eq) and H—W-Boc or H—W—SO$_2$-A or HCl salt (2 eq) in DMF are stirred at rt for between 1 h and 2 days. HATU (2 eq) was added in one portion and then DMAP (3 eq). The reaction was stirred at rt for 2 to 15 h (reaction progress monitored by standard methods ie TLC, LC/MS). The mixture is filtered through filter paper to collect the solid. The filtrate is concentrated and water is added. The mixture is filtered again and the solid is washed with water. The solid is conbined and washed with water. Many reagents for amide bond couplings are known by an organic chemist skilled in the art and nearly all of these are applicable for realizing coupled amide products. As mentioned above, DEPBT (3-(diethoxyphosphoryloxy)-1,2,3-benzotriazin-4(3H)-one) and N,N-diisopropylethylamine, commonly known as Hunig's base, represents another efficient method to form the amide bond (step D) and provide compounds of claim 1. DEPBT is either purchased from Adrich or prepared according to the procedure of Ref. 28, Li, H.; Jiang, X.; Ye, Y.-H.; Fan, C.; Romoff, T.; Goodman, M. *Organic Lett.*, 1999, 1, 91–93. Typically an inert solvent such as DMF or THF is used but other aprotic solvents could be used.

The amide bond construction reaction could be carried out using the preferred conditions described above, the EDC conditions described below, other coupling conditions described in this application, or alternatively by applying the conditions or coupling reagents for amide bond construction described later in this application for construction of substituents R$_2$-R$_5$. Some specific nonlimiting examples are given in this application.

Alternatively, the acid could be converted to a methyl ester using excess diazomethane in THF/ether. The methyl ester in dry THF could be reacted with the lithium amide of intermediate H—W. The lithium amide of H—W, Li—W is formed by reacting intermediate 1 with lithium bistrimethylsilylamide in THF for 30 minutes in an ice water cooling bath. Sodium or potassium amides could be formed similarly and utilized if additional reactivity is desired. Other esters such as ethyl, phenyl, or pentafluorophenyl could be utilized and would be formed using standard methodology.

It should be noted that in many cases reactions are depicted for only one position of an intermediate, such as the R$^5$ position, for example. It is to be understood that such reactions could be used at other positions, such as R$^2$-R$^4$, of the various intermediates. Reaction conditions and methods given in the specific examples are broadly applicable to compounds with other substitution and other tranformations in this application. Schemes 1 and 2 describe general reaction schemes for taking appropriately substituted Q (indoles and azaindoles) and converting them to compounds of Formula I. While these schemes are very general, other permutations such as carrying a precursor or precursors to substituents R$^2$ through R$^5$ through the reaction scheme and then converting it to a compound of Formula I in the last step are also contemplated methods of this invention. Nonlimiting examples of such strategies follow in subsequent schemes. Procedures for coupling piperazine amides to oxoacetyl derivatives are described in the Blair, Wang, Wallace, or Wang references 93–95 and 106 respectively. The entire disclosures in U.S. Pat. No. 6,469,006 granted Oct. 22, 2002; U.S. Pat. No. 6,476,034 granted Nov. 5, 2002; U.S. patent application Ser. No. 10/027,612 filed Dec. 19, 2001, which is a continuation-in-part of U.S. Ser. No. 09/888,686 filed Jun. 25, 2001 (corresponding to PCT WO 02/04440, published Jan. 17, 2002); and U.S. patent application Ser. No. 10/214,982 filed Aug. 7, 2002, which is a continuation-in-part of U.S. Ser. No. 10/038,306 filed Jan. 2, 2002 (corresponding to PCT WO 02/62423 published Aug. 15, 2002) are incorporated by reference herein. The procedures used to couple indole or azaindole oxoacetic acids to piperazine amides in these references can be used analogously to form the compounds of this invention except the piperazine sulfonyl ureas are used in place of the piperazine benzamides. It should be stated that the procedures incorporated from these applications encompass the preparation of strating materials and transformations which are useful for enabling the preparation of compounds of this invention.

Step E. Cleaveage of the protecting group, (intermediate 5a, scheme 1) affords piperazine 6a. Some typical conditions for the removal of BOC employ acid such as HCl or TFA in a 1:1 mixture of $H_2O$ and other solvent such as THF, MeOH or acetonitrile. Altenatively, the cleaveage can be carried out with an ahydrous solution of 20% TFA in methylene chloride.

Step F. Sulfamoylation of piperazine intermediate 6a was carried out as described in scheme A. Therefore a solution of intermediate 6a in anhydrous tetrahydrofuran was treated with a sulfamoyl chloride (2–3 eq.) in the presence of triethylamine (3–10eq) at room temperature for 18 h to afford sulfonylurea 7a.

The amide bond construction reactions depicted in step D of scheme 1 could be carried out using the specialized conditions described herein or alternatively by applying the conditions or coupling reagents for amide bond construction described in Wallace, reference 95. Some specific nonlimiting examples are given in this application.

Alternatively, compounds of formula I can be prepared from compounds of formula 6a (presented as having general formula Z-W—H) as depicted in scheme B.

Scheme B

Z—W—H $\xrightarrow[CH_2Cl_2]{\substack{Cl_2SO_2 \\ R_3N}}$ Z—W—S(=O)(=O)—Cl $\xrightarrow[CH_3CN]{\substack{AH \\ R_3N}}$

8

Z—W—S(=O)(=O)—A

I

Compounds of formula Z-W—H can be treated with tertiary amines such as Hunig's base or triethylamine (1 eq.–2 eq.) and sulfuryl chloride (0.5 eq.) in an anhydrous aprotic solvent such as methylene chloride or THF usually at temperatures between 0° C. and 25° C. Sometimes higher temperatures may be used (25° C.–75° C.) to generate sulfamoyl chloride intermediate 8. Intermediate 8 can be converted into compounds of formula I by reaction with primary or secondary amines (2 eq.–3 eq.) in the presence of a tertiary amine (3eq.–10 eq.) such as Hunig's base or triethylamine in an anhydrous aprotic solvent such as acetonitrile, methylene chloride or THF at temperatures ranging from 0° C. to 25° C., although higher reaction temperatures maybe used (25° C.–75° C.).

Additional procedures for synthesizing, modifying and attaching groups are contained in references 93–95 or 106 as incorporated earlier or described below.

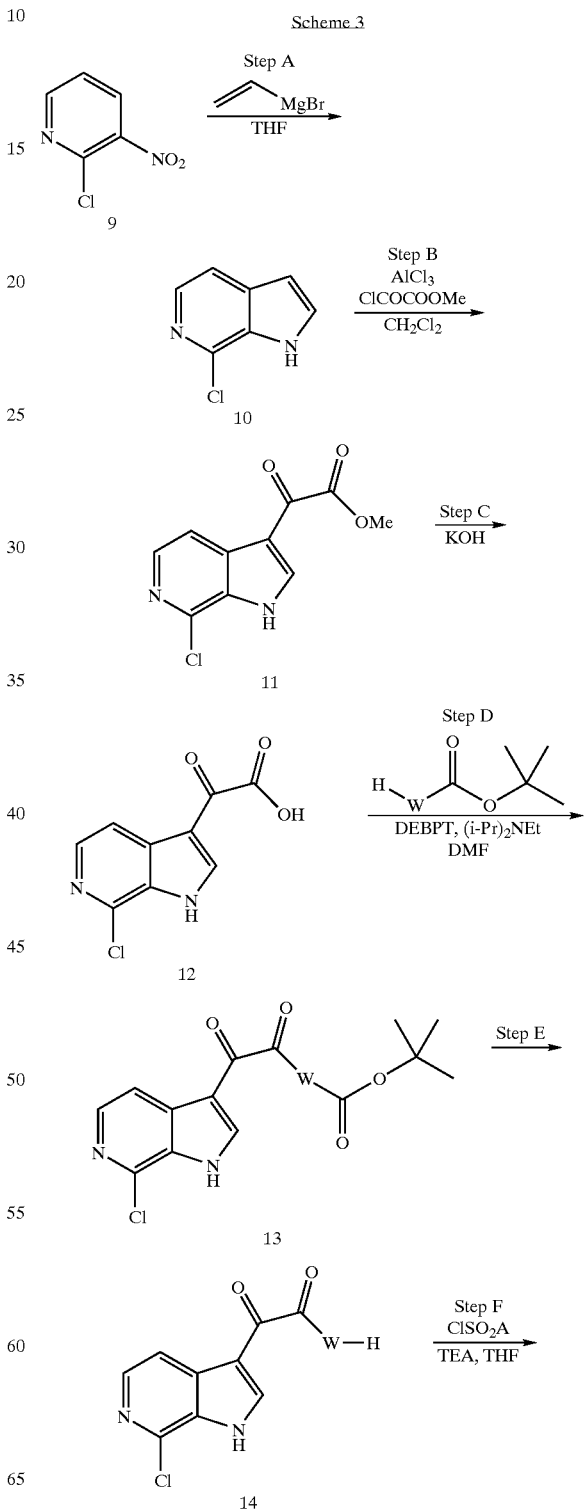

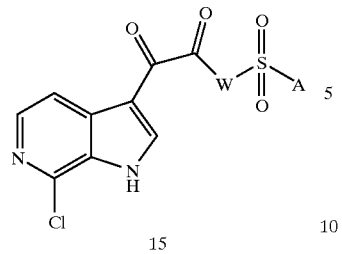

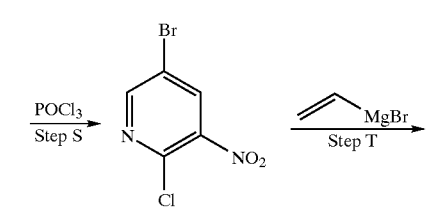

Scheme 4

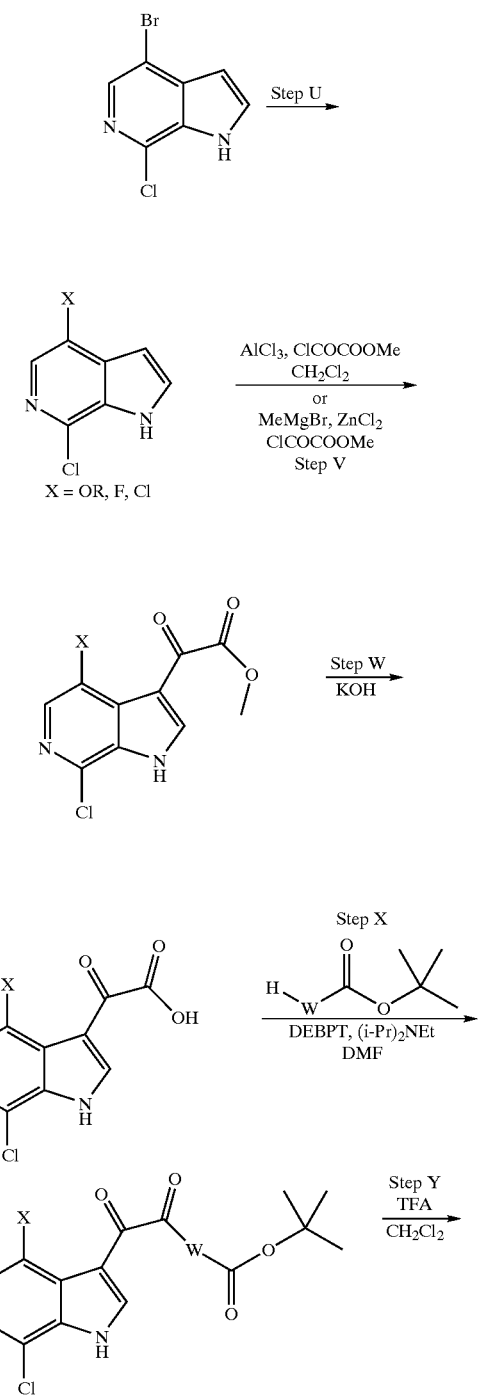

Schemes 1 and 3 provide more specific examples of the transformation previously described in Scheme A. Intermediates 9–15 are prepared by the methodologies as described for intermediates 1a–7a in Scheme 1. Scheme 4 is another embodiment of the transformations described in Schemes 1 and 3. Conversion of the phenol to the chloride (Step S, Scheme 4) may be accomplished according to the procedures described in Reimann, E.; Wichmann, P.; Hoefner, G.; Sci. Pharm. 1996, 64(3), 637–646; and Katritzky, A. R.; Rachwal, S.; Smith, T. P.; Steel, P. J.; *J. Heterocycl. Chem.* 1995, 32(3), 979–984. Step T of Scheme 4 can be carried out as described for Step A of Scheme 1. The bromo intermediate can then be converted into alkoxy, chloro, or fluoro intermediates as shown in Step U of Scheme 4. When step U is the conversion of the bromide into alkoxy derivatives, the conversion may be carried out by reacting the bromide with an excess of sodium methoxide in methanol with cuprous salts, such as copper I bromide, copper I iodide, and copper I cyanide. The reaction may be carried out at temperatures of between ambient and 175° C. but most likely will be around 115° C. or 100° C. The reaction may be run in a pressure vessel or sealed tube to prevent escape of volatiles such as methanol. The preferred conditions utilize 3 eq of sodium methoxide in methanol, CuBr as the reaction catalyst (0.2 to 3 equivalents with the preferred being 1 eq or less), and a reaction temperature of 115° C. The reaction is carried out in a sealed tube or sealed reaction vessel. The conversion of the bromide into alkoxy derivatives may also be carried out according to procedures described in Palucki, M.; Wolfe, J. P.; Buchwald, S. L.; *J. Am. Chem. Soc.* 1997, 119(14), 3395–3396; Yamato, T.; Komine, M.; Nagano, Y.; *Org. Prep. Proc. Int.* 1997, 29(3), 300–303; Rychnovsky, S. D.; Hwang, K.; *J. Org. Chem.* 1994, 59(18), 5414–5418. Conversion of the bromide to the fluoro derivative (Step U, Scheme 4) may be accomplished according to Antipin, I. S.; Vigalok, A. I.; Konovalov, A. I.; *Zh. Org. Khim.* 1991, 27(7), 1577–1577; and Uchibori, Y.; Umeno, M.; Seto, H.; Qian, Z.; Yoshioka, H.; *Synlett.* 1992, 4, 345–346. Conversion of the bromide to the chloro derivative (Step U, Scheme 5) may be accomplished according to procedures described in Gilbert, E. J.; Van Vranken, D. L.; *J. Am. Chem. Soc.* 1996, 118(23), 5500–5501; Mongin, F.; Mongin, O.; Trecourt, F.; Godard, A.; Queguiner, G.; *Tetrahedron Lett.* 1996, 37(37), 6695–6698; and O'Connor, K. J.; Burrows, C. J.; *J. Org. Chem.* 1991, 56(3), 1344–1346. Steps V, W, X, Y and Z of Scheme 4 are carried out according to the procedures previously described for Steps B, C, D, E and F of Scheme 1, respectively. The steps of Scheme 4 may be carried out in a different order as shown in Scheme 5 and Scheme 6.

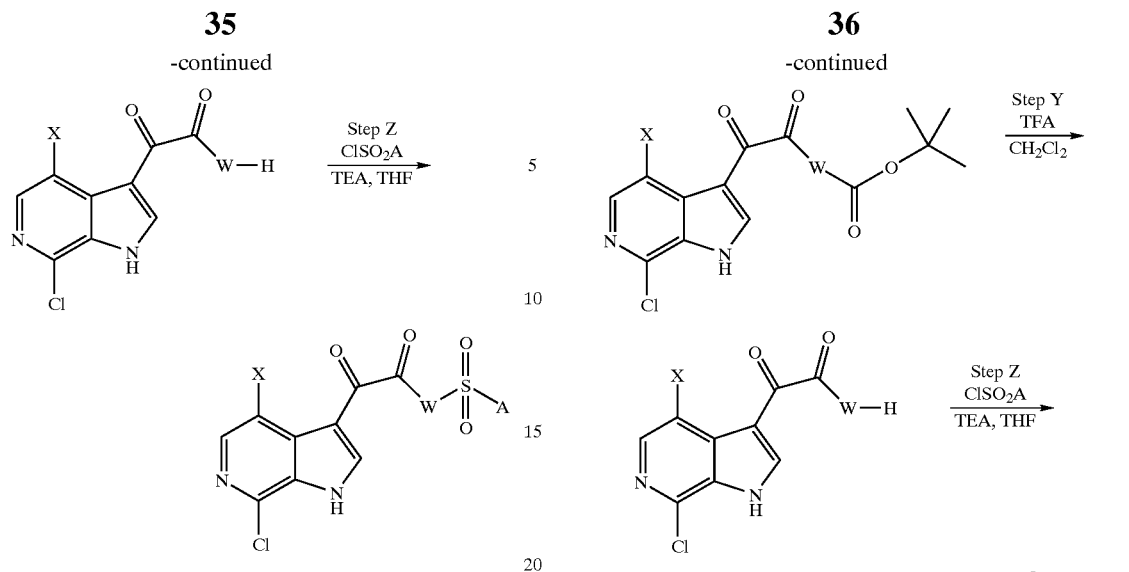
Scheme 5
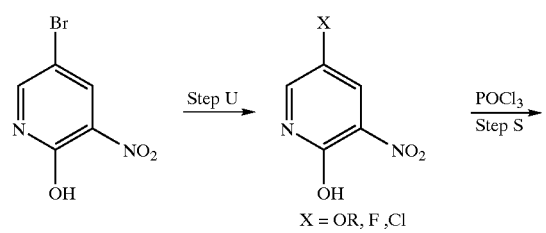
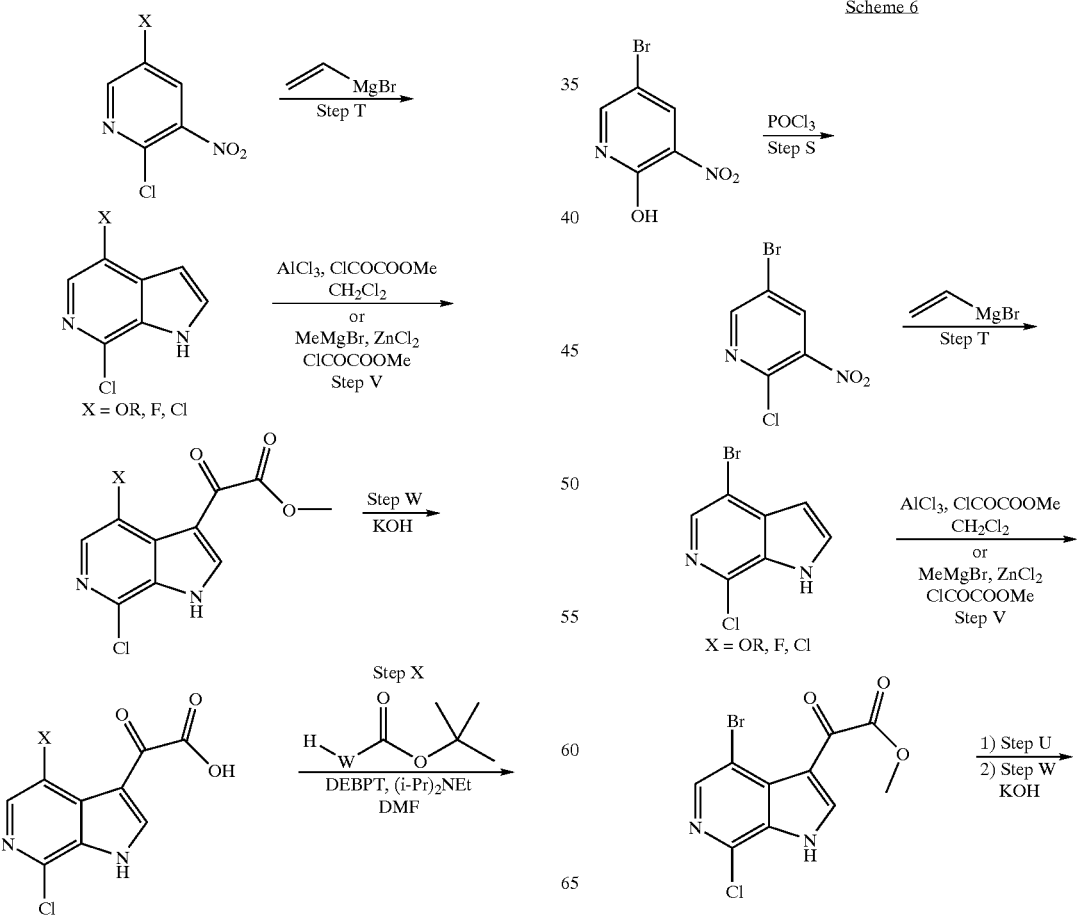
Scheme 6

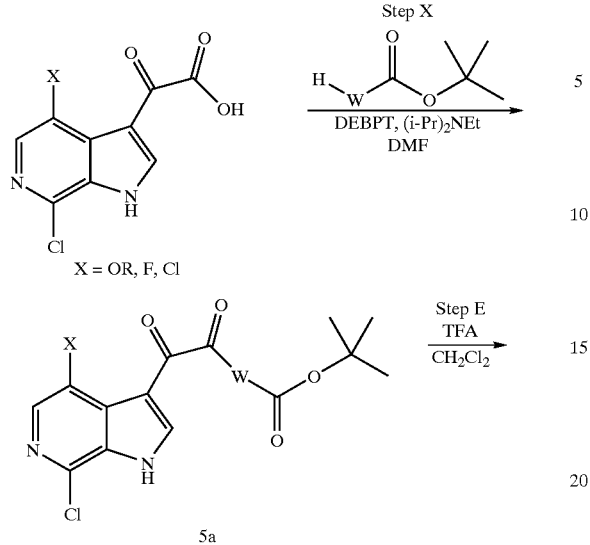
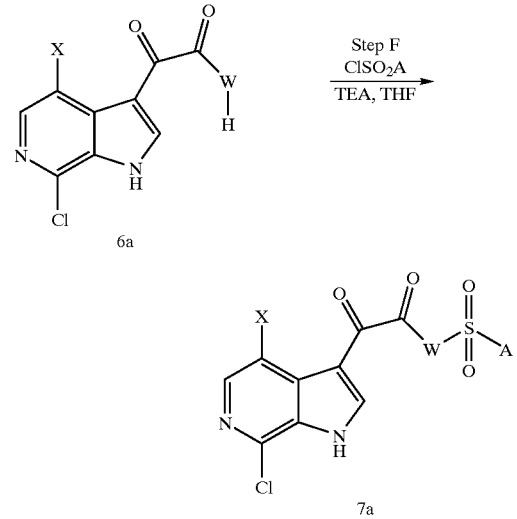

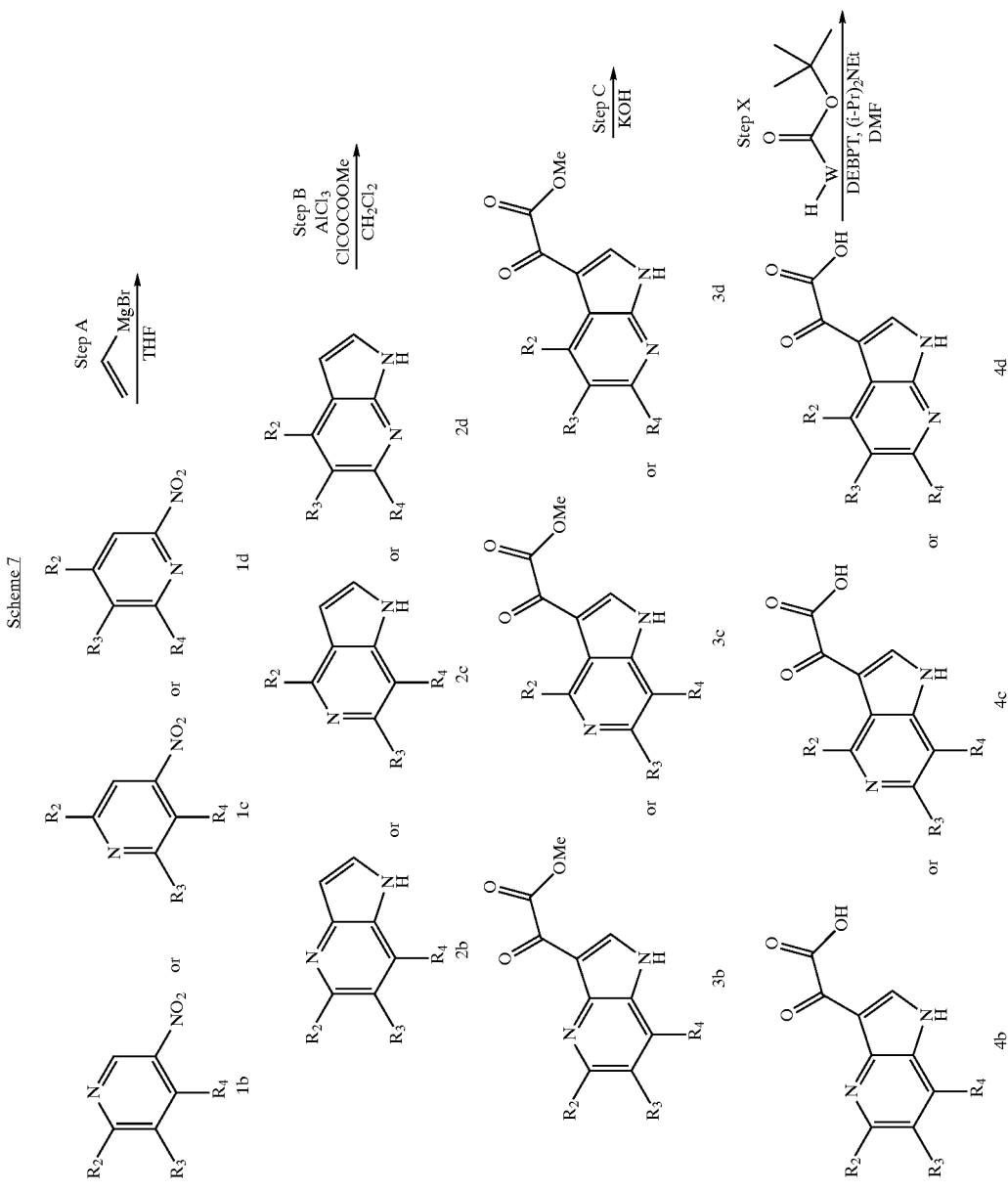

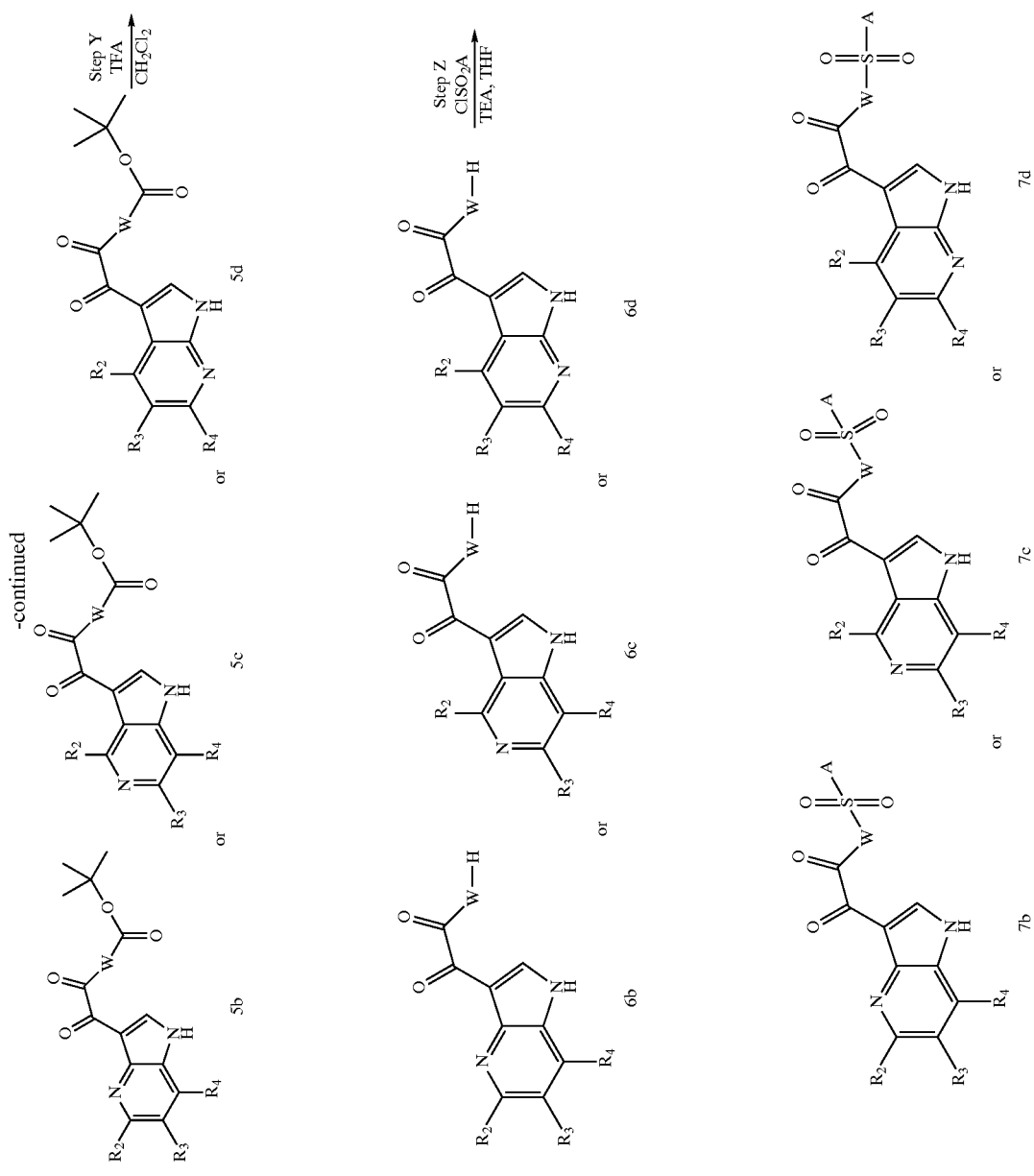

Scheme 7 shows the synthesis of 4-azaindole derivatives 2b–7b, 5-azaindole derivatives 2c–7c, and 7-azaindole derivatives 2d–7d. The methods used to synthesize 1b–5b, 1c–5c, and 1d–5d are the same methods described for the synthesis of 1a–5a as described in Scheme 1. It is understood, for the purposes of Scheme 7, that 1b is used to synthesize 2b–5b, 1c provides 2c–5c and 1d provides 2d–5d.

The compounds where there is a single carbonyl between the azaindole and group W can be prepared by the method of Kelarev, V. I.; Gasanov, S. Sh.; Karakhanov, R. A.; Polivin, Yu. N.; Kuatbekova, K. P.; Panina, M. E.; *Zh. Org. Khim* 1992, 28(12), 2561–2568. In this method azaindoles are reacted with trichloroacetyl chloride in pyridine and then subsequently with KOH in methanol to provide the 3-carbomethoxy azaindoles shown in Scheme 3 which can then be hydrolyzed to the acid and carried through sequence shown in the scheme to provide the compounds of Formula I wherein a single carbonyl links the azaindole moiety and group W.

Scheme 8

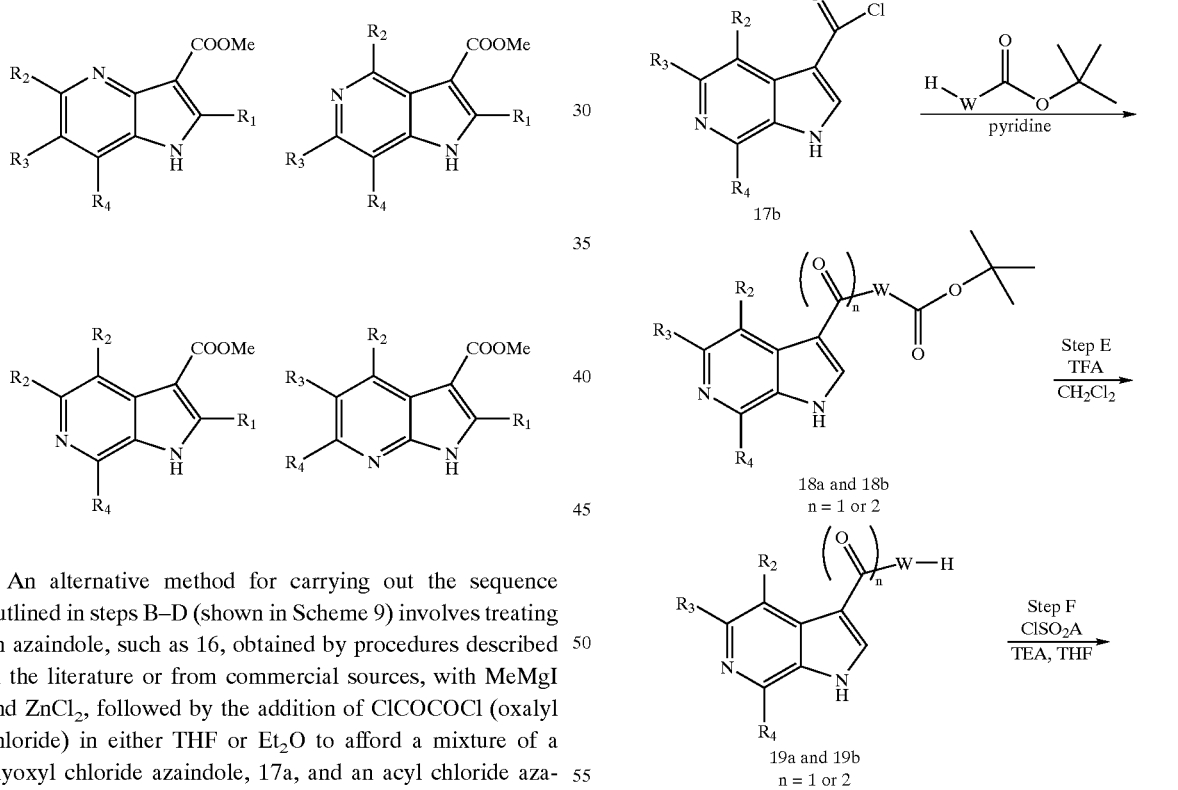

An alternative method for carrying out the sequence outlined in steps B–D (shown in Scheme 9) involves treating an azaindole, such as 16, obtained by procedures described in the literature or from commercial sources, with MeMgI and $ZnCl_2$, followed by the addition of ClCOCOCl (oxalyl chloride) in either THF or $Et_2O$ to afford a mixture of a glyoxyl chloride azaindole, 17a, and an acyl chloride azaindole, 17b. The resulting mixture of glyoxyl chloride azaindole and acyl chloride azaindole is then coupled with mono-benzoylated piperazine derivatives under basic conditions to afford the products of step D as a mixture of compounds, 18a and 18b, where either one or two carbonyl groups link the azaindole and group W. Separation via chromatographic methods which are well known in the art provides the pure 18a and 18b. Conversion of 18a and 18b to 20a and 20b can be done following steps E and F. This sequence is summarized in Scheme 9, below.

Scheme 9

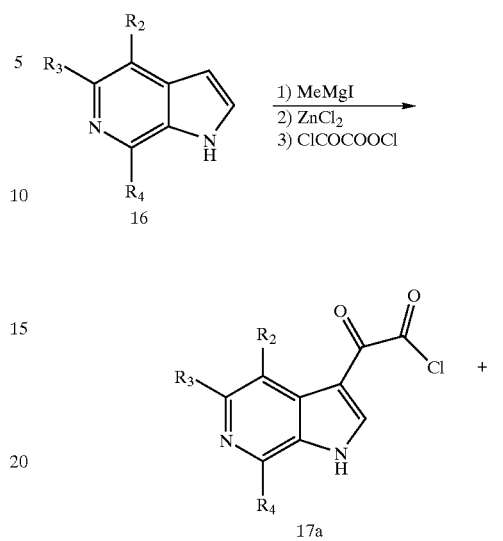

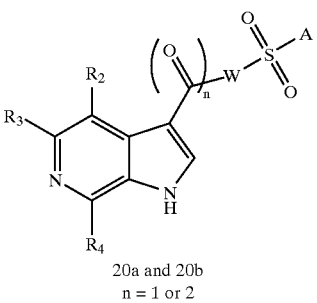

Scheme 15

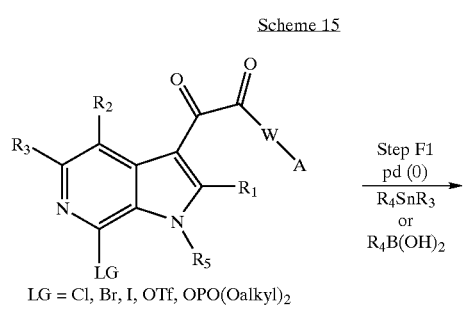

LG = Cl, Br, I, OTf, OPO(Oalkyl)₂

Step F1
pd (0)
―――――――→
R₄SnR₃
or
R₄B(OH)₂

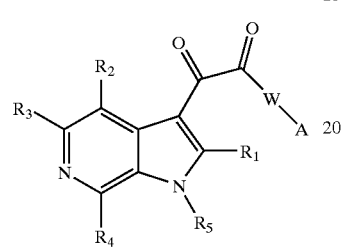

Step F

As shown above in Scheme 15, Step F1, substituted azaindoles containing a chloride, bromide, iodide, triflate, or phosphonate undergo coupling reactions with a boronate (Suzuki type reactions) or a stannane (Stille type coupling) to provide substituted indoles or azaindoles. This type of coupling as mentioned previously can also be used to functionalize vinyl halides, triflates or phosphonates to add groups D or A or precursors. Stannanes and boronates are prepared via standard literature procedures or as described in the experimental section of this application. The substituted indoles, azaindoles, or alkenes may undergo metal mediated coupling to provide compounds of Formula I wherein $R_4$ is aryl, heteroaryl, or heteroalicyclic for example. The indoles or azaindole intermediates, (halogens, triflates, phosphonates) may undergo Stille-type coupling with heteroarylstannanes as shown in Scheme 15 or with the corresponding vinyl reagents as described in earlier Schemes. Conditions for this reaction are well known in the art and the following are three example references a) Farina, V.; Roth, G. P. Recent advances in the Stille reaction; *Adv. Met. -Org. Chem.* 1996, 5, 1–53. b) Farina, V.; Krishnamurthy, V.; Scott, W. J. The Stille reaction; *Org. React.* (N. Y.) 1997, 50, 1–652. and c) Stille, J. K. *Angew. Chem. Int. Ed. Engl.* 1986, 25, 508–524. Other references for general coupling conditions are also in the reference by Richard C. Larock Comprehensive Organic Transformations 2nd Ed. 1999, John Wiley and Sons New York. All of these references provide numerous conditions at the disposal of those skilled in the art in addition to the specific examples provided in Scheme 15 and in the specific embodiments. It can be well recognized that an indole stannane could also couple to a heterocyclic or aryl halide or triflate to construct compounds of Formula I. Suzuki coupling (Norio Miyaura and Akiro Suzuki *Chem Rev.* 1995, 95, 2457. ) between a triflate, bromo, or chloro azaindole intermediate and a suitable boronate could also be employed and some specific examples are contained in this application. Palladium catalyzed couplings of stannanes and boronates between halo azaindole or indole intermediates or vinyl halides or vinyl triflates or similar vinyl substrate are also feasible and have been utilized extensively for this invention. Preferred procedures for coupling of a chloro or bromo azaindole or vinyl halide and a stannane employ dioxane, stoichiometric or an excess of the tin reagent (up to 5 equivalents), 0.1 to 1 eq of tetrakis triphenyl phosphine Palladium (0) in dioxane heated for 5 to 15 h at 110 to 120°. Other solvents such as DMF, THF, toluene, or benzene could be employed. Another useful procedure for coupling a halo indole or azaindole with a suitable tributyl heteroaryl or other stannane employs usually a slight excess (1.1 eqs) but up to several equivalents of the stannane, 0.1 eqs CuI, 0.1 equivalents of tetrakis triphenyl phosphine palladium (O) all of which is usually dissolved in dry DMF (approximately 5 mmol of halide per 25 mL of DMF but this concentration can be reduced for sluggish reactions or increased if solubility is an issue). The reaction is usually heated at an elevated temperature of about 90° C. and the reaction is usually run in a sealed reaction vessel or sealed tube. When the reaction is completed it is usually allowed to cool, filtered through methanesulfonic acid SCX cartridges with MeOH to remove triphenyl phosphine oxide, and then purified by standard crystallization or chromatographic methods. Examples of the utility of these conditions are shown in Scheme Z below.

SCHEME Z

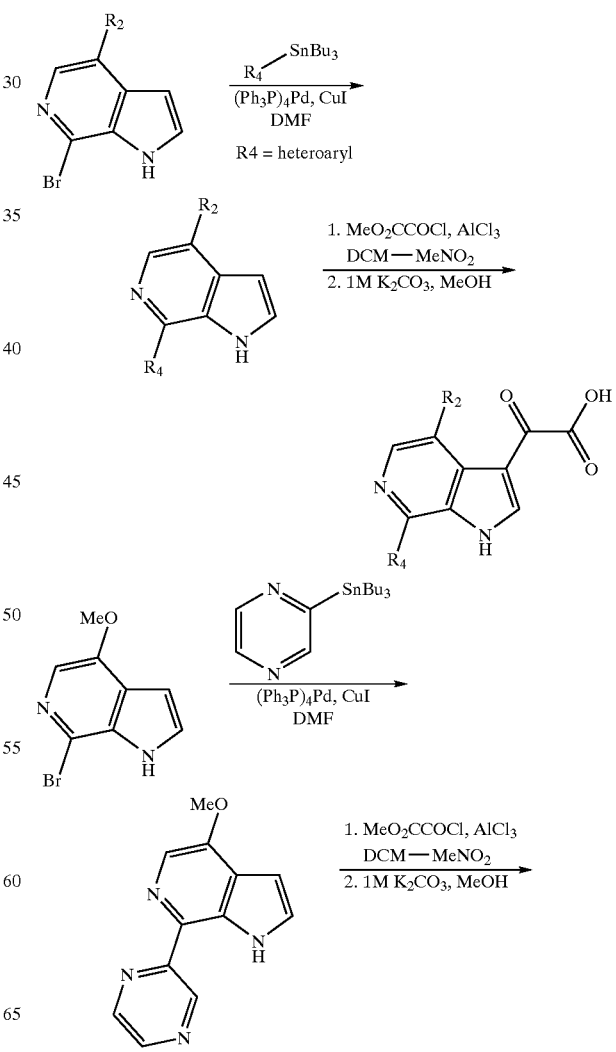

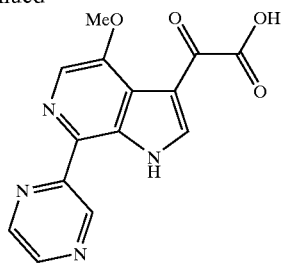

Alternatively, the Stille type coupling between a stannane (~1.1 eqs) and a vinyl, heteroaryl, or aryl halide may proceed better using (0.05 to 0.1 eq) bvPd2(dba)3 as catalyst and tri-2-furylphosphine (~0.25eq) as the added ligand. The reaction is usually heated in THF or dioxane at a temperature between 70 and 90° C. Preferred procedures for Suzuki coupling of a chloro azaindole and a boronate employ 1:1 DMF water as solvent, 2 equivalents of potassium carbonate as base stoichiometric or an excess of the boron reagent (up to 5 equivalents), 0.1 to 1 eq of Palladium (0) tetrakis triphenyl phosphine heated for 5 to 15 h at 110 to 120°. Less water is occasionally employed. Another useful condition for coupling a heteroaryl or aryl boronic acid to a stoichiometric amount of vinyl halide or triflate utilizes DME as solvent (~0.33 mmol halide per 3 mL DME), ~4 eq of 2M sodium carbonate, and 0.05 eq Pd2dba3 heated in a sealed tube or sealed vessel at 90° C. for ~16 h. Reaction times vary with substrate. Another useful method for coupling involves use of coupling an aryl, heteroaryl, or vinyl zinc bromide or chloride coupled with a vinyl, aryl, or heteroaryl halide using tetrakis triphenyl phosphine palladium (O) heated in THF. Detailed example procedures for preparing the zinc reagents from halides via lithium bromide exhange and then transmetalation and reaction conditions are contained in the experimental section. If standard conditions fail new specialized catalysts and conditions can be employed. Discussions on details, conditions, and alternatives for carrying out the metal mediated couplings described above can also be found in the book "Organometallics in Organic Synthesis; A Manual; 2002, $2^{nd}$ Ed. M. Schlosser editor, John Wiley and Sons, West Sussex, England, ISBN 0 471 98416 7.

Some references (and the references therein) describing catalysts which are useful for coupling with aryl and heteroaryl chlorides are:

Littke, A. F.; Dai, C.; Fu, G. C. J. Am. Chem. Soc. 2000, 122(17), 4020–4028;
Varma, R. S.; Naicker, K. P. Tetrahedron Lett. 1999, 40(3), 439–442; Wallow, T. I.;
Novak, B. M. J. Org. Chem. 1994, 59(17), 5034–7; Buchwald, S.; Old, D. W.;
Wolfe, J. P.; Palucki, M.; Kamikawa, K.; Chieffi, A.; Sadighi, J. P.; Singer, R. A.;
Ahman, J PCT Int. Appl. WO 0002887 2000; Wolfe, J. P.; Buchwald, S. L. Angew. Chem., Int. Ed. 1999, 38(23), 3415; Wolfe, J. P.; Singer, R. A.; Yang, B. H.;
Buchwald, S. L. J. Am. Chem. Soc. 1999, 121(41), 9550–9561; Wolfe, J. P.;
Buchwald, S. L. Angew. Chem., Int. Ed. 1999, 38(16), 2413–2416; Bracher, F.;
Hildebrand, D.; Liebigs Ann. Chem. 1992, 12, 1315–1319; and Bracher, F.;
Hildebrand, D.; Liebigs Ann. Chem. 1993, 8, 837–839.

Alternatively, the boronate or stannane may be formed on the azaindole via methods known in the art and the coupling performed in the reverse manner with aryl or heteroaryl based halogens or triflates.

Known boronate or stannane agents could be either purchased from commercial resources or prepared following disclosed documents. Additional examples for the preparation of tin reagents or boronate reagents are contained in the experimental section, and references 93–95 and 106.

Novel stannane agents could be prepared from one of the following routes which should not be viewed as limiting.

Scheme Tin-01

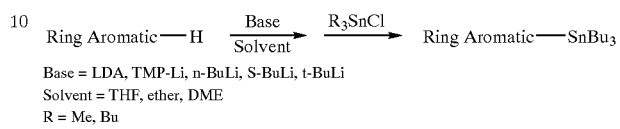

Base = LDA, TMP-Li, n-BuLi, S-BuLi, t-BuLi
Solvent = THF, ether, DME
R = Me, Bu

Scheme Tin-02

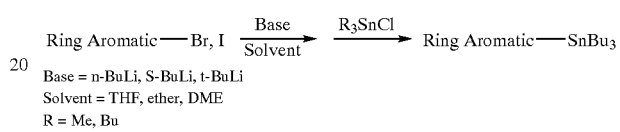

Base = n-BuLi, S-BuLi, t-BuLi
Solvent = THF, ether, DME
R = Me, Bu

Scheme Tin-03

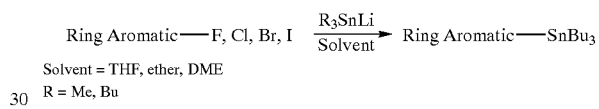

Solvent = THF, ether, DME
R = Me, Bu

Scheme Tin-04

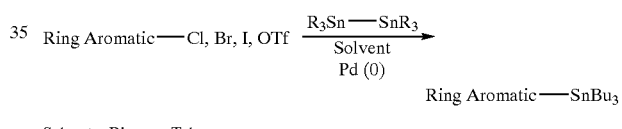

Solvent = Dioxane, Toluene
R = Me, Bu

Scheme Tin-05

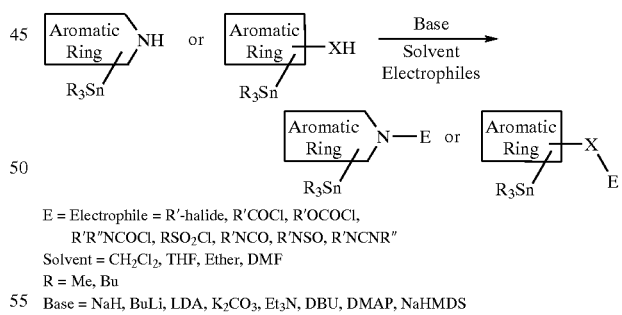

E = Electrophile = R'-halide, R'COCl, R'OCOCl,
R'R"NCOCl, RSO₂Cl, R'NCO, R'NSO, R'NCNR"
Solvent = CH₂Cl₂, THF, Ether, DMF
R = Me, Bu
Base = NaH, BuLi, LDA, K₂CO₃, Et₃N, DBU, DMAP, NaHMDS Boronate reagents are prepared as described in reference 71. Reaction of lithium or Grignard reagents with trialkyl borates generates boronates. Alternatively, Palladium catalyzed couplings of alkoxy diboron or alkyl diboron reagents with aryl or heteroaryl halides can provide boron reagents for use in Suzuki type couplings. Some example conditions for coupling a halide with (MeO)BB(OMe)2 utilize PdCl2 (dppf), KOAc, DMSO, at 80° C. until reaction is complete when followed by TLC or HPLC analysis.

Related examples are provided in the following experimental section.

Methods for direct addition of aryl or heteroaryl organometallic reagents to alpha chloro nitrogen containing heterocyles or the N-oxides of nitrogen containing heterocycles are known and applicable to the azaindoles. Some examples are Shiotani et. Al. *J. Heterocyclic Chem.* 1997, 34(3), 901–907; Fourmigue et. al. *J. Org. Chem.* 1991, 56(16), 4858–4864.

SCHEME 12

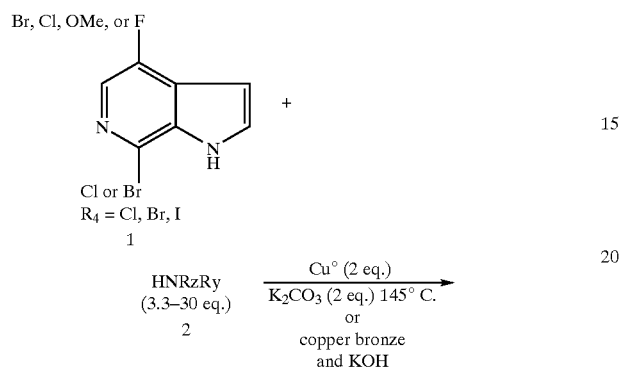

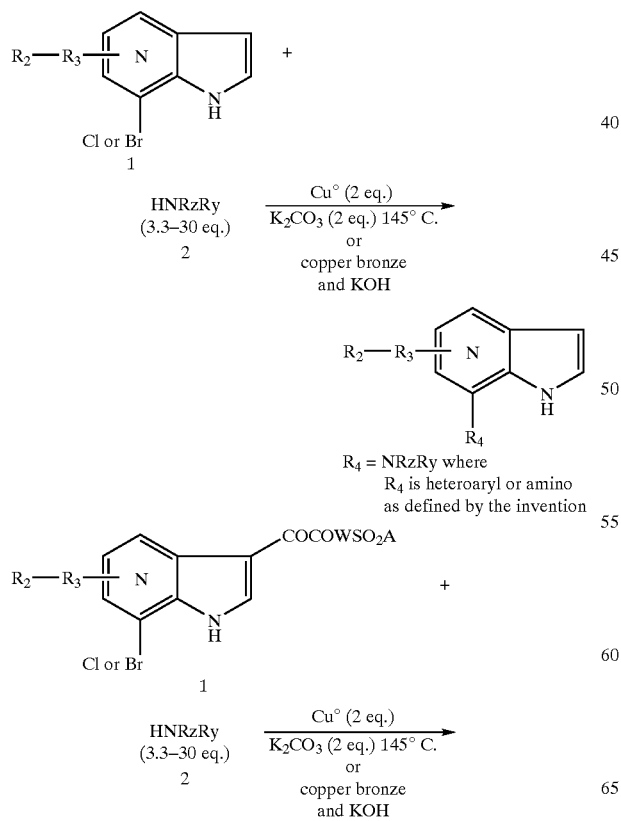

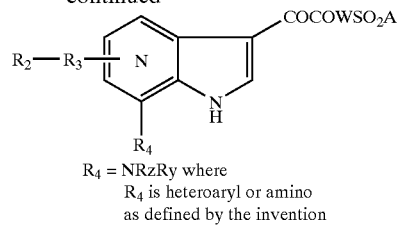

$R_4 = NR_zR_y$ where
$R_4$ is heteroaryl or amino
as defined by the invention

SCHEME 13

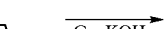

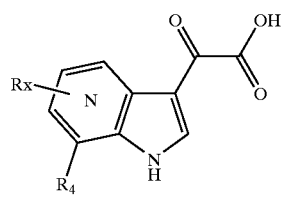

($R_4H$ is a heteroaryl or amine with free N—H)

$R_x = R_2-R_4$ for azaindoles or $R_2-R_5$ for indoles

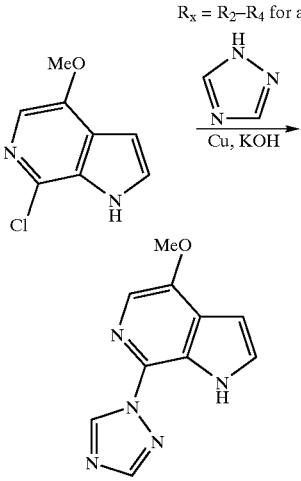

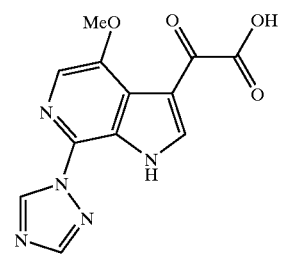

As shown in Schemes 12 and 13, a mixture of halo-indole or halo-azaindole intermediate, 1–2 equivalents of copper powder, with 1 equivalent preferred for the 4-F,6-azaindole series and 2 equivalents for the 4-methoxy,6-azaindole series; 1–2 equivalents of potassium carbonate, with 1 equivalent preferred for the 4-F,6-azaindole series and 2 equivalents for the 4-methoxy,6-azaindole series; and a 2–30 equivalents of the corresponding heterocyclic reagent, with 10 equivalents preferred; was heated at 135–160° C. for 4 to 9 hours, with 5 hours at 160° C. preferred for the 4-F,6-azaindole series and 7 hours at 135° C. preferred for the 4-methoxy,6-azaindole series. The reaction mixture was cooled to room temperature and filtered through filter paper. The filtrate was diluted with methanol and purified either by preparative HPLC or silica gel. In many cases no chromatography is necessary, the product can be obtained by crystallization with methanol.

Alternatively, the installation of amines or N linked heteroaryls may be carried out by heating 1 to 40 equivalents of the appropriate amine and an equivalent of the appropriate aza indole chloride, bromide or iodide with copper bronze (from 0.1 to 10 equivalents (preferably about 2 equivalents) and from 1 to 10 equivalents of finely pulverized potassium hydroxide (preferably about 2 equivalents).

Temperatures of 120° to 200° C. may be employed with 140–160° C. generally preferred. For volatile starting materials a sealed reactor may be employed. The reaction is most commonly used when the halogen being displaced is at the 7-position of a 6-aza or 4-azaindole but the method can work in the 5-azaseries or when the halogen is at a different position (4–7 position possible). As shown above the reaction can be employed on azaindoles unsubstituted at position 3 or intermediates which contain the dicarbonyl or the intact dicarbonyl piperazine sulfonyl urea.

Chemistry

All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

LC/MS Method (i.e., Compound Identification)

Note: column A is used unless otherwise indicated in the preparation of intermediates or examples.

| | |
|---|---|
| Column A: | YMC ODS-A S7 3.0 × 50 mm column |
| Column B: | PHX-LUNA C18 4.6 × 30 mm column |
| Column C: | XTERRA ms C18 4.6 × 30 mm column |
| Column D: | YMC ODS-A C18 4.6 × 30 mm column |
| Column E: | YMC ODS-A C18 4.6 × 33 mm column |
| Column F: | YMC C18 S5 4.6 × 50 mm column |
| Column G: | XTERRA C18 S7 3.0 × 50 mm column |
| Gradient: | 100% Solvent A/0% Solvent B to 0% Solvent A/100% Solvent $R_t$ in min. |
| Gradient time: | 2 minutes |
| Hold time | 1 minute |
| Flow rate: | 5 mL/min |
| Detector Wavelength: | 220 nm |
| Solvent A: | 10% MeOH/90% $H_2O$/0.1% Trifluoroacetic Acid |
| Solvent B: | 10% $H_2O$/90% MeOH/0.1% Trifluoroacetic Acid |

Compounds purified by preparative HPLC were diluted in MeOH (1.2 mL) and purified using the following methods on a Shimadzu LC-10A automated preparative HPLC system or on a Shimadzu LC-8A automated preparative HPLC system with detector (SPD-10AV UV-VIS) wavelength and solvent systems (A and B) the same as above.

Preparative HPLC Method (i.e., Compound Purification)

Purification Method: Initial gradient (40% B, 60% A) ramp to final gradient (100% B, 0% A) over 20 minutes, hold for 3 minutes (100% B, 0% A)

| | |
|---|---|
| Solvent A: | 10% MeOH/90% $H_2O$/0.1% Trifluoroacetic Acid |
| Solvent B: | 10% $H_2O$/90% MeOH/0.1% Trifluoroacetic Acid |
| Column: | YMC C18 S5 20 × 100 mm column |
| Detector Wavelength: | 220 nm |

General and Example Procedures Excerpted from Analogous Oxoacetyl Piperazineamide Applications The procedures described in references 93–95 and 106 are applicable example procedures for synthesizing the compounds of formula I in this application and the intermediates used for their synthesis. The following guidelines are illustrative but not limiting.

The general Bartoli (vinyl Magnesium bromide) methods for preparing functionalized indoles or azaindoles dexcribed in the applications can be utilized for preparing new indoles or azaindoles from the appropriate nitro aromatics or heteroaromatics for this application. For example, in PCT/US02/00455 (PCT WO 02/062423), the general procedure for preparing intermediate 2a (7-chloro-6-azaindole) from 2-chloro-3-nitro pyridine can be considered a general procedure illustrating conditions which can be used to prepare azaindoles for this application. This should be obvious since the same class of intermdiates are needed for both inventions. Similarly, the general procedure from the same application to prepare intermediate 3a, Methyl (7-chloro-6azaindol-3-yl) oxoacetate, provides experimental details for carrying our Step B of (Schemes 1–7 in this application) Similarly, the general procedure from the same application to prepare intermediate 4a (Potassium(7-chloro-6azaindol-3-yl) oxoacetate, provides an example of the general method for hydrolying oxoacteic esters (Step C of Schemes 1–1c, 3–7). General procedures for carrying out the same steps in the indole series are provided in references 93 and 95. An example Bartoli reaction preparation of a functionalized indole is given in the preparation of intermediate 1 of PCT/US01/20300 (U.S. Pat. No. 6,573,262) where the preparation of 4-fluoro-7-bromo-azaindole is described from 2-fluoro-5-bromonitrobenzene. Subsequent procedures for the preparation of intermediates 2 and 3 describe procedures for adding the alkyl oxoacetate and then for ester hydrolysis to provide the carboxylate salt and then the carboxylic acid after acidification. Thus the chemistry described in the incoprorated previous applications for preparing azaindole and indole intermediates is obviously applicable since the desired compounds are the same.

Procedures for carrying out the coupling of the indole or azaindole oxoacetic acids to piperazine amides are described in the references 93–95 and 106. These can also be used as procedures for preparing the piperazine sulfonyl ureas of this invention by taking the experimental procedures and substituting a piperazine sulfonyl urea or mon protected piperazine in place of the piperazine amide. This is possible because both groups have a free amine with relatively similar activity and since the other portions of both the piperazine benzamide and the piperizine sulfonyl urea are relatively unreactive to many conditions, they can be installed similarly. For example, the preparation of intermediate 4 of PCT/US01/20300 and the preparation of intermediate 5a of PCT/US02/00455 describe couplings of a piperazine benzamide or methyl piperazine benzamide to an indole or azaindole oxoacetic acid or carboxylate salt respectively. (The acid or salt can be used interchangeably).

These same procedures can be used directly for the preparation of the compounds of this invention by substituting the desired piperazine sulfonyl ureas for the piperazine amides utilized.

Preparation of Intermediate 5a from PCT/US02/00455

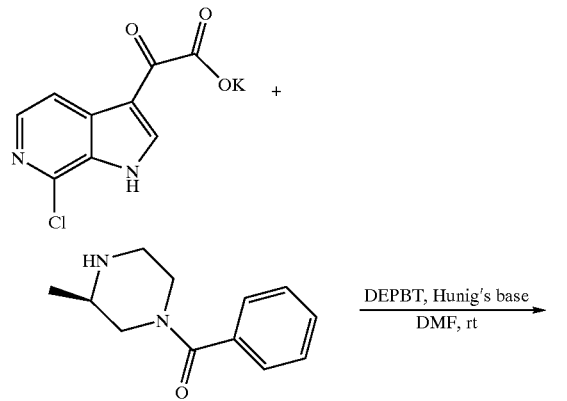

can be used as a procedure for

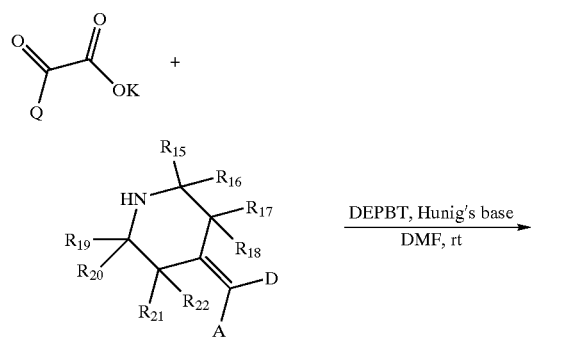

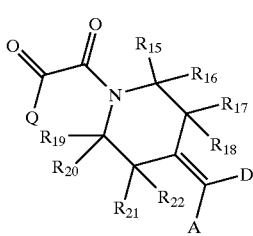

Preparation of Intermediate 4 from PCT/US01/20300

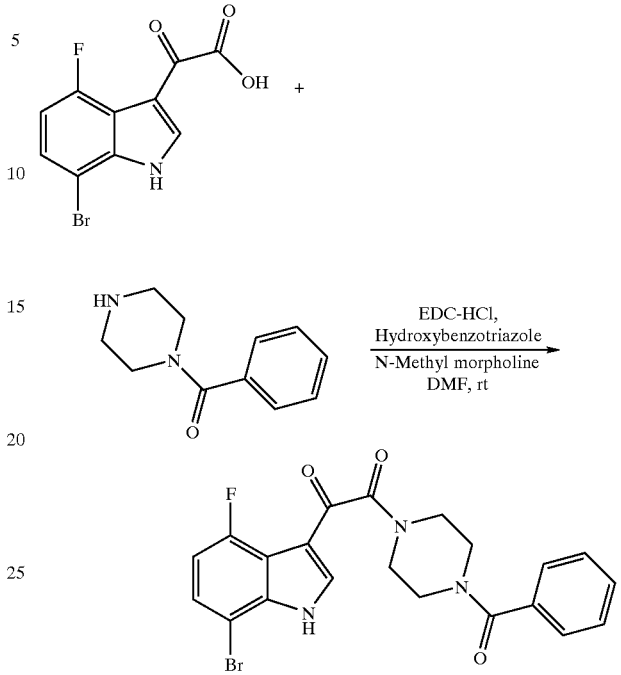

can be used as a procedure for

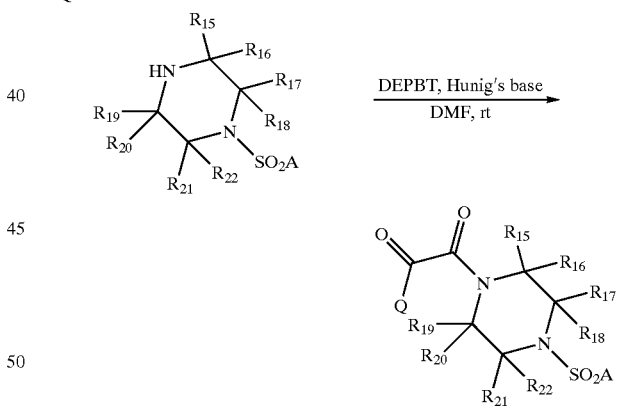

Once attached via a similar amide bond, both the piperazine benzamides and the piperazine sulfonyl urea moieties are relatively inert and thus reaction conditions used for functionalizing indoles or azaindoles in the presence of piperazine benzamides are useful for carrying out the same tranformations in the presence of the piperazine sulfonyl ureas. Thus the methods and transformations described in references 93–95 and 106 including the experimental procedures which describe methods to functionalize the indole or azaindole moiety in the piperazine amide series are generally applicable for construction and functionalization of the piperazine sulfonyl ureas of this invention. These same applications describe general methods and specific preparations for obtaining stannane and boronic acid reagents used for synthesizing the compounds of formula I.

Preparation of Example 1 from PCT/US02/00455

Typical Boron/Palladium Coupling Procedure

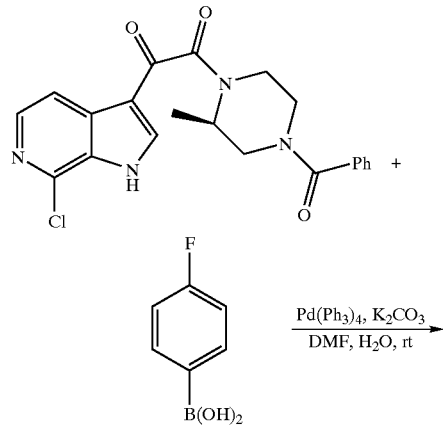

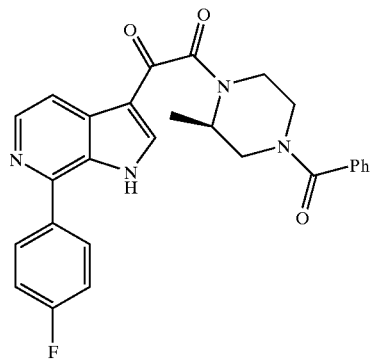

can be used as a procedure for

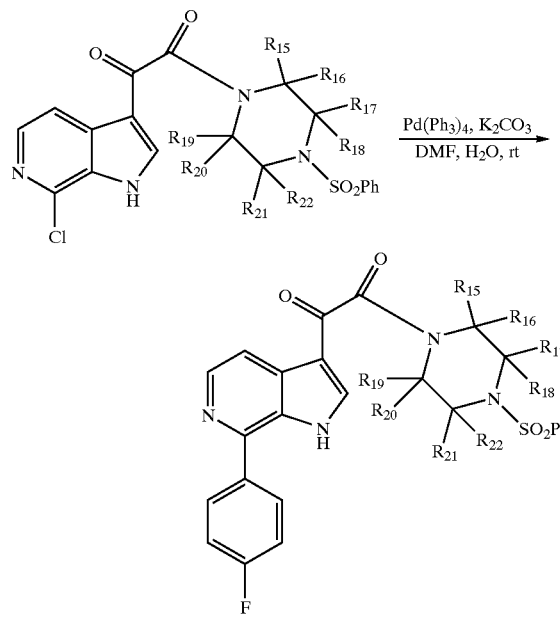

or even as a procedure for

Group—B(OH)$_2$ +

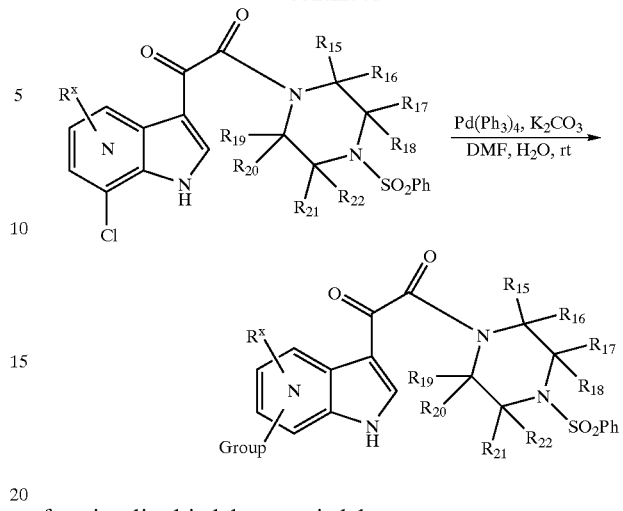

functionalized indole or azaindole
where $R^x$ is as described for Scheme 7

Preparation of Example 39 from PCT/US02/00455

An Example of the Typical Stannane/Palladium Coupling Procedure

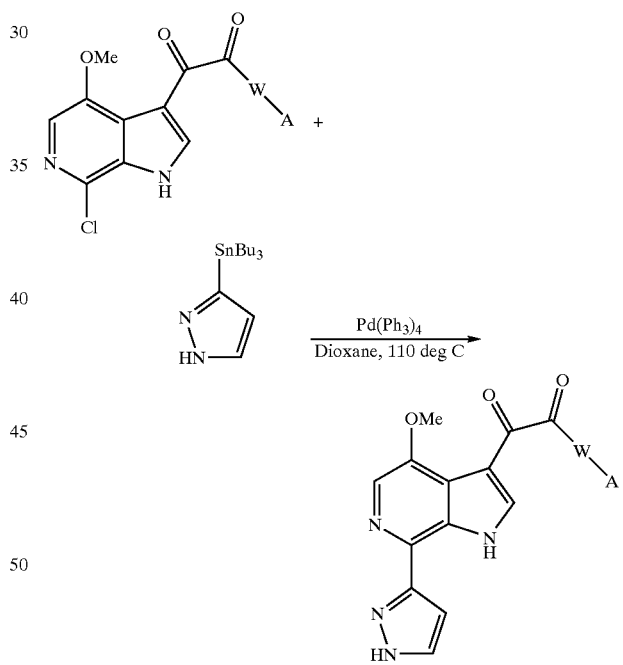

can be used as a procedure for

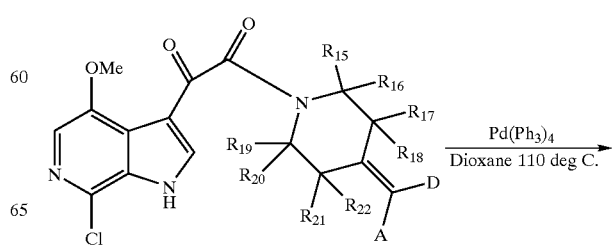

-continued

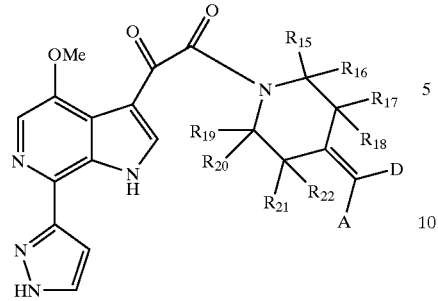

or even as a procedure for

Group—SnBu₃ +

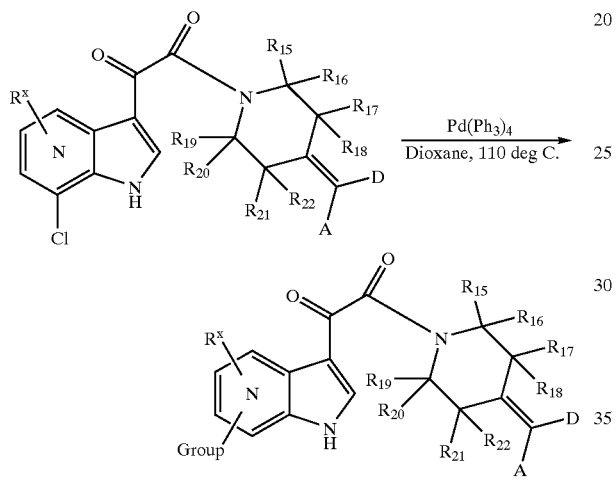

functionalized indole or azaindole where R$^x$ is as described for Scheme 7

Preparation of Example 20 from PCT/US01/20300

An Example to Show how Functionalization Procedures of Oxoacetyl Piperazine Benzamides can be Used to Carry out Similar Tranformations in the Corresponding Piperidine Alkenes

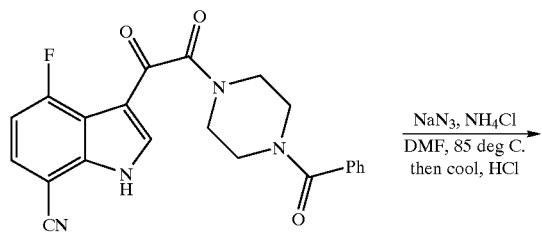

-continued

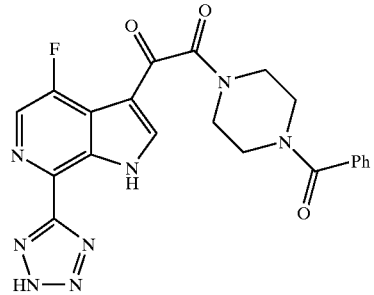

can be used as a procedure for

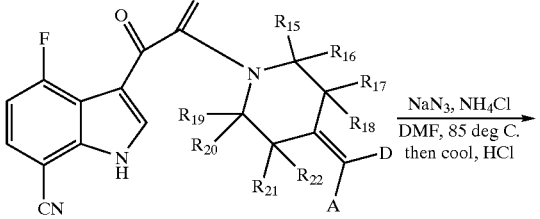

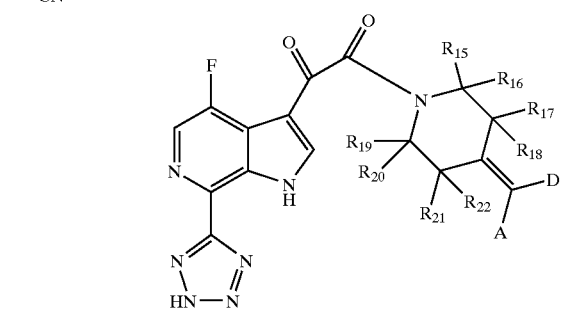

or even as a procedure for

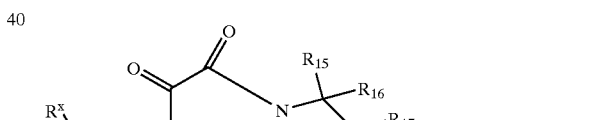

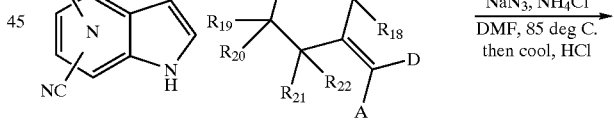

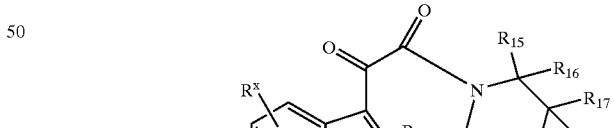

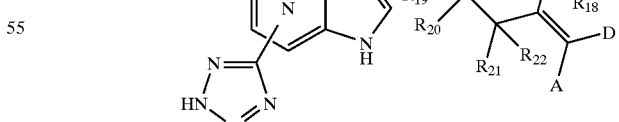

functionalized indole or azaindole
where R$^x$ is as described for Scheme 7

Preparation of Intermediates and Examples:

All starting materials, unless otherwise indicated can be purchased from commercial sources. Methods are given for the preparation intermediates.

EXAMPLE 1

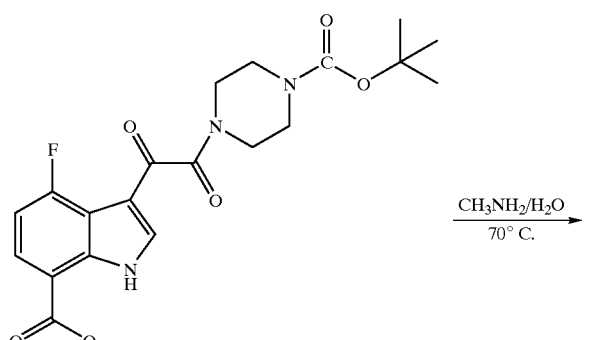

intermediate 1

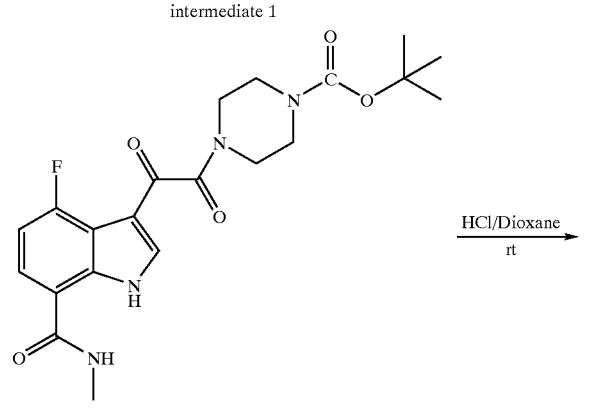

intermediate 2

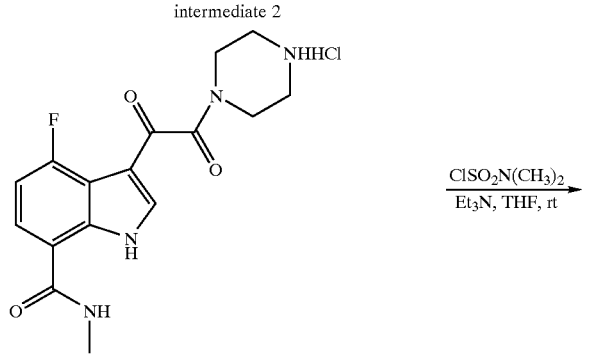

intermediate 3

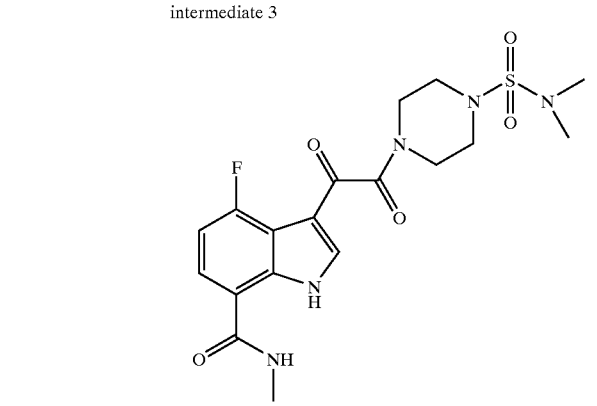

Example 1

Preparation of intermediate 1.

Intermediate 1 was prepared according to procedures described in Wallace, O. B. et al. PCT int. appl. WO0204440, and as described in Steps A–D below.

Step A

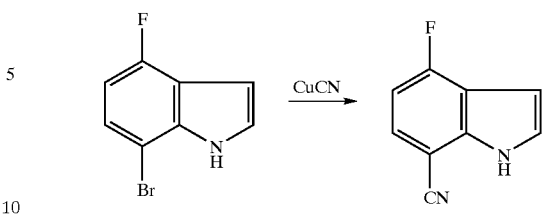

A mixture of 4-fluoro-7-bromoindole (600 mg, 2.8 mmol) and CuCN (1.004 g, 11.2 mmol) in DMF (4 ml) was refluxed for 16 hours. After cooling to room temperature, the reaction mixture was poured into a solution of ammonia in MeOH (30 ml, sat.) and the residue removed by filtration. The filtrate was added to a mixture of water (20 ml)/ammonia (20 ml, sat. aq.) and extracted with EtOAc/Ether (1/1) until TLC analysis showed no product in the aqueous phase. The combined organic extracts were washed with brine (2×200 ml) and water (200 ml), dried (MgSO$_4$); evaporation in vacuo gave 4-fluoro-7-cyanoindole as a tan yellow solid (310 mg, 69%).

Step B

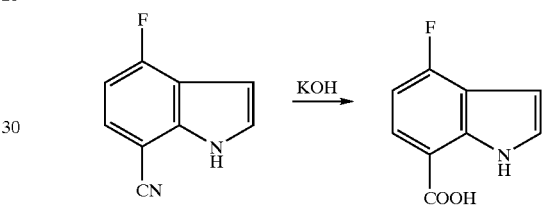

To a solution of KOH (13.04 g, 0.232 mol) in 14% H$_2$O/EtOH (50 ml) was added 4-fluoro-7-cyanoindole (900 mg, 5.60 mmol). The resulting mixture was refluxed for 12 hours, slowly cooled to room temperature, and concentrated in vacuo to about 30 ml. The residue was acidified to pH 2 with HCl (~5.5 N aq.). The precipitate was filtered, washed with excess of water, and dried under high vacuum to afford 4-fluoro-7-carboxyindole as a white solid (100% conversion). The material was used without further purification.

Step C

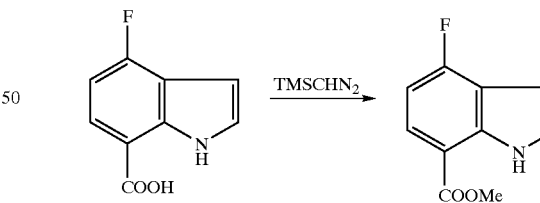

To a suspension of 4-fluoro-7-carboxyindole in a mixture of MeOH (18 ml)/PhH (62 ml) was added (trimethylsilyl) diazomethane (8.8 ml, 17.6 mmol, 2 M in hexane). The resulting mixture was stirred at room temperature for 30 min., quenched with excess acetic acid and evaporated in vacuo. The crude oily material was purified by flash chromatography using a gradient elution (Hexane to 10% EtOAc/Hexane) to afford 4-fluoro-7-carbomethoxy indole as a white solid (1.04 g, 83% two steps).

Step D

Oxalyl chloride (1.2 eq.) was added dropwise to a solution of 4-fluoro-7-carbomethoxy indole (1 eq.) prepared as described above, in dry THF at 0° C. After 5 min., the cool bath was removed and the reaction was allowed to warm to rt and stirred until completion determined by LCMS. The mixture was then concentrated under reduced pressure to provide the crude oxo acetyl chloride. Triethylamine (8.88 mmol, 1.23 mL) and 1-Boc piperazine (7.4 mmol, 1.38 g) was added to a solution of the crude 3-oxoacetyl chloride of 4-fluoro-7-carbomethoxy indole (7.4 mmol) in THF (70 mL) and the mixture was stirred at room temperature overnight. A saturated aqueous solution of NaHCO$_3$ (100 mL) was added and then the mixture was extracted with methylene chloride (3×100 mL). The combined organic extracts were dried over sodium sulfate to afford a crude containing intermediate 1. This crude intermediate 1 was used without further purification in the next step. MS (ESI$^+$): 333(M+H)$^+$.

Preparation of Intermediate 2

A mixture of intermediate 1 (1.0 g, 2.3 mmol) and 40% methylamine in water (40 mL) was heated to 70° C. in a sealed flask for 5 hr. The resulting solution was then concentrated in rotoevaporator and dried in vacuo to afford intermediate 2 (1.0 g, 99%) which was used in next step without further purification. $^1$H NMR (500 MHz, CDCl$_3$): 8.12–8.11 (m, 1H); 7.44–7.39 (m, 1H); 7.00–6.94 (m, 1H); 6.38–6.29 (m, 1H); 3.72–3.47 (m, 8H); 3.07–3.05 (d, 3H); 1.55 (s, 9H). MS (ESI$^+$): 334 (M+H-Boc)$^+$.

Preparation of Intermediate 3

Intermediate 2 (1.0 g, 2.3 mmol) was treated with hydrogen chloride (7 mL, 28 mmol, 4N in dioxane) at room temperature. After stirring for 16 hr, the resulting mixture was concentrated and dried in vacuo to afford intermediate 3 (1.0 g, 99%) which was used in next step without further purification. MS (ESI$^+$): 333 (M+H)$^+$.

EXAMPLE 1

A THF (1 ml) solution of intermediate 3 (50 mg, 0.14 mmol) was treated with triethylamine (39 µl, 0.28 mmol) followed by dimethylsulfamoyl chloride (30 µl, 0.28 mmol) at room temperature. The reaction was stirred for 16 h, then concentrated in rotoevaporator. The residue was dissolved in methanol and purified on preparative HPLC to afford the title compound (16 mg, 27%). $^1$H NMR (500 MHz, CDCl$_3$): 8.09 (s, 1H); 7.45–7.39 (m, 1H); 6.99–6.94 (m, 1H); 6.43–6.38 (bs, 1H); 3.83 (m, 2H); 3.59 (m, 2H); 3.38 (m, 2H); 3.31–3.30 (m, 2H); 3.07–3.05 (m, 3H); 2.83 (s, 6H). MS (ESI$^+$): 440 (M+H)$^+$.

General Procedure for Preparation of Non-Commercially Available Sulfamoyl Chlorides Sulfamoyl chlorides were prepared in two steps from commercially available amines following Method A or B:

Method A

Step 1

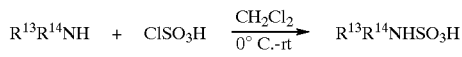

The corresponding amine (3 mmol) was dissolved in anhydrous methylene chloride (3 mL) and placed in an ice bath. Chlorosulfonic acid (1 mmol) was added and the mixture was stirred at this temperature for 15 min. The ice bath was removed and the stirring was continued for 1 h at rt. The sulfamic acid precipitated as white solids which were collected by filtration, dried under vacuum and used in the next step without further purification.

Step 2

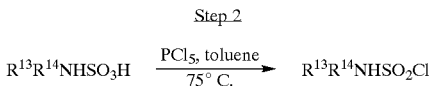

The corresponding sulfamic acid from step 1 (1 mmol) was suspended in anhydrous toluene (1 mL) and the mixture was heated at 75° C. for 2 h. The homogeneous mixture was cooled to rt. Volatiles were removed in vacuum and the sulfamoyl chloride was used in the next step without further purification.

The following sulfamoyl chlorides were prepared following method A: Phenylsulfamoyl choride, methylsulfamoyl chloride.

Method B

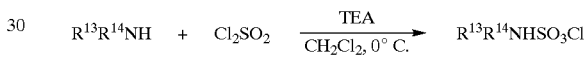

The corresponding amine (10 mmol) was dissolved in anhydrous methylene chloride (20 mL) and treated with triethylamine (10 mmol). The mixture was placed in an ice bath and sulfonyl chloride (20 mmol) was added dropwise. The reaction mixture was stirred at 0° C. for 15 min., then at rt for 1 h. A saturated aqueous solution of sodium carbonate (50 mL) was used to quench the reaction, and the organics were extracted with methylene chloride (2×50 mL), dried over sodium sulfate and concentrated in vacuum. The sulfamoyl chloride was used without further purification.

The following sulfamoyl chlorides were prepared following method B: Morpholinosulfamoyl choride.

EXAMPLE 2

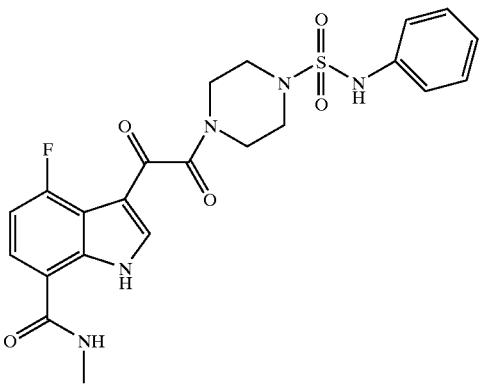

Example 2 was prepared from intermediate 3 following the same procedure described in example 1 using phenylsulfamoyl choride. ¹H NMR (300 MHz, CD₃OD): 8.11 (s, 1H); 7.73–7.69 (m, 1H); 7.30–7.21 (m, 3H); 7.10–7.09 (m, 1H); 7.03–6.97 (m, 1H); 3.0 (m, 2H); 3.42 (m, 2H); 3.34 (m, 2H); 3.29 (m, 2H); 2.96 (s,3H). MS (ESI⁺): 488 (M+H)⁺.

EXAMPLE 3

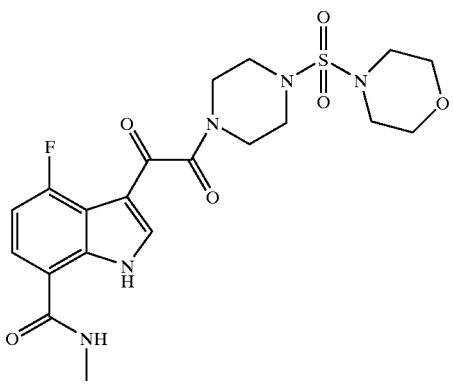

Example 3 was prepared from intermediate 3 following the same procedure described in example 1 using morpholinosulfamoyl choride. ¹H NMR (300 MHz, CDCl₃): 8.12 (d, 1H, J=3.0 Hz); 7.44–7.40 (m, 1H); 7.01–6.95 (m, 1H); 6.34 (bs, 1H); 3.84–3.81 (m, 2H); 3.74–3.71 (m, 4H); 3.61–3.58 (m, 2H); 3.40–3.33 (m, 4H); 3.25–3.22 (m, 4H); 3.06 (d, 3H, J=3 Hz). MS (ESI⁺): 482 (M+H)⁺.

EXAMPLE 4

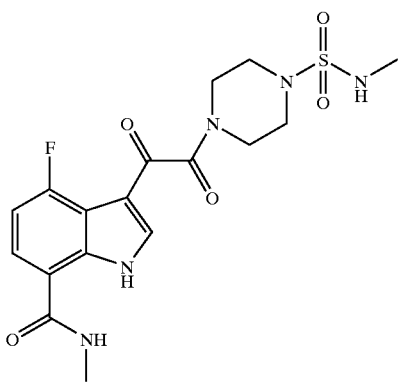

Example 4 was prepared from intermediate 3 following the same procedure described in example 1 using methylsulfamoyl choride and acetonitrile as a solvent instead of methylene chloride. ¹H NMR (500 MHz, CD₃OD): 8.20 (s, 1H); 7.77–7.74 (m, 1H); 7.08–7.05 (m, 1H); 3.86–3.84 (m, 2H); 3.61–3.59 (m, 2H); 3.36–3.32 (m, 2H); 3.24–3.22 (m, 4H); 2.99 (s, 3H); 2.68 (s, 3H). MS (ESI⁺): 426 (M+H)⁺.

EXAMPLE 5

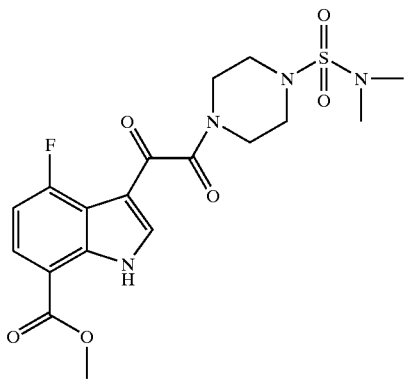

Intermediate 1 (80 mg, 0.18 mmol) was treated with a 20% TFA in CH₂Cl₂ solution (2 mL) at room temperature for 3 h. The reaction mixture was rotavaped down, redissolved in acetonitrile (2 mL) and treated with triethylamine (41 uL, 0.54 mmol) and dimethylsulfamoyl chloride (39 uL, 0.36 mmol). The reaction mixture was stirred at rt for 18 h, then the volatiles were removed in vacuo and the crude was chromatographed on silica gel using a 5%MeOH/CH₂Cl₂ solution as eluent. The fractions containing the title compound were combined, concentrated and purified using the preparative reverse phase HPLC to afford the title compound as a white solid (37 mg, 47%). ¹HNMR (300 MHz, CDCl₃): 1.71 (bs, 1H), 8.13 (s, 1H), 7.95 (m, 1H), 7.01 (m, 1H), 3.98 (s, 3H), 3.82 (m, 2H), 3.59 (m, 2H), 3.33 (m, 4H), 2.84 (s, 6H). MS (ESI⁺): 441 (M+H)⁺.

EXAMPLE 6

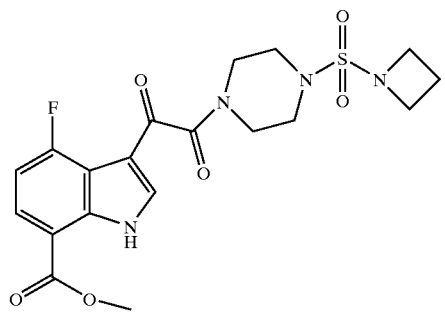

Example 6 was prepared from intermediate 1 following the procedure described in example 5 using cyclobutylsufamoyl chloride. ¹H-NMR (300 MHz, CDCl₃): 10.68 (bs, 1H); 8.15–8.11 (m, 1H); 7.98–7.95 (m, 1H); 7.05–6.98 (m, 1H); 4.04 (s, 3H); 4.01–3.28 (m, 12H), 2.27–2.24 (m, 2H). LC/MS: (ES⁺) m/z (m+H)⁺=453. Rt=1.24 min.

EXAMPLE 7

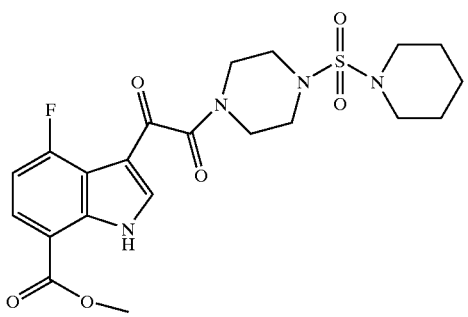

Example 7 was prepared from intermediate 1 following the procedure described in example 5 using piperidinesulfamoyl chloride. ¹H-NMR (300 MHz, CDCl$_3$): 10.68 (bs, 1H); 8.14–8.13 (m, 1H); 7.98–7.95 (m, 1H); 7.04–7.00 (m, 1H); 3.99 (s, 3H); 3.88–3.21 (m, 12H), 1.62–1.55 (m, 6H). LC/MS: (ES$^+$) m/z (m+H)$^+$=481. Rt=1.40 min.

EXAMPLE 8

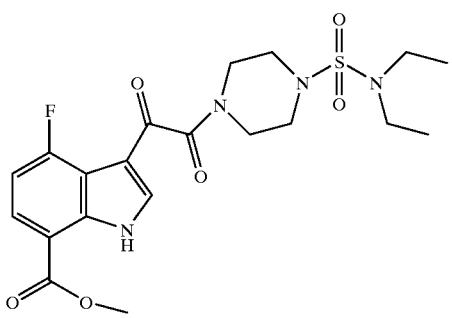

Example 8 was prepared from intermediate 1 following the procedure described in example 5 using dimethylsulfamoyl chloride. ¹H-NMR (300 MHz, CDCl$_3$): 10.68 (bs, 1H); 8.13–8.12 (m, 1H); 7.97–7.94 (m, 1H); 7.02–6.98 (m, 1H); 3.99 (s, 3H); 3.88–3.26 (m, 12H), 1.20–1.16 (m, 6H). LC/MS: (ES$^+$) m/z (m+H)$^+$=469. Rt=1.36 min.

EXAMPLE 9

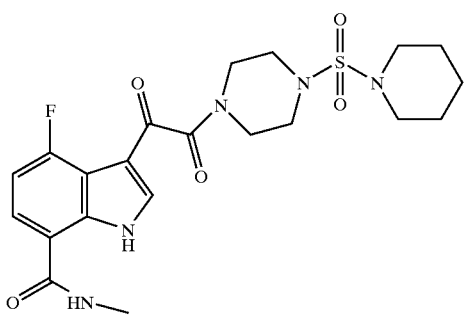

Example 9 was prepared from intermediate 3 following the procedure described in example 1 using piperidinesulfamoyl chloride. ¹H-NMR (500 MHz, DMSO): 12.44 (bs, 1H); 8.69–8.68 (m, 1H); 8.06–8.05 m, 1H); 7.81–7.79 (m, 1H); 7.12–7.09 (m, 1H); 3.69–3.10 (m, 12H); 2.86–2.85 (m,3H), 1.51–1.50 (m, 6H). LC/MS: (ES$^+$) m/z (m+H)$^+$= 480. Rt=1.32 min.

EXAMPLE 10

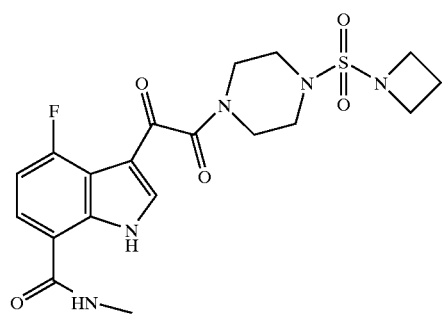

Example 10 was prepared from intermediate 3 following the procedure described in example 1 using cyclobutylsulfamoyl chloride. ¹H-NMR (500 MHz, DMSO): 12.44 (bs, 1H); 8.69–8.68 (m, 1H); 8.06–8.05 (m, 1H); 7.80–7.78 (m, 1H); 7.12–7.09 (m, 1H); 3.83–3.10 (m, 12H); 2.86–2.85 (m, 3H), 2.20–2.16 (m, 2H). LC/MS: (ES$^+$) m/z (m+H)$^+$=452. Rt=1.12 min.

EXAMPLE 11

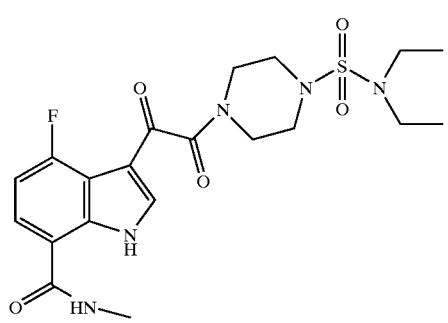

Example 11 was prepared from intermediate 3 following the procedure described in example 1 using dimethylsulfamoyl chloride. ¹H-NMR (500 MHz, DMSO): 12.44 (bs, 1H); 8.69–8.68 (m, 1H); 8.06–8.05 (m, 1H); 7.80–7.78 (m, 1H); 7.12–7.09 (m, 1H); 3.70–3.00 (m, 12H); 2.86–2.85 (m, 3H), 1.10–1.08 (m, 6H). LC/MS: (ES$^+$) m/z (m+H)$^+$=468. Rt=1.25 min.

EXAMPLE 12

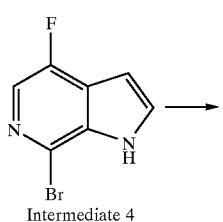

Intermediate 4

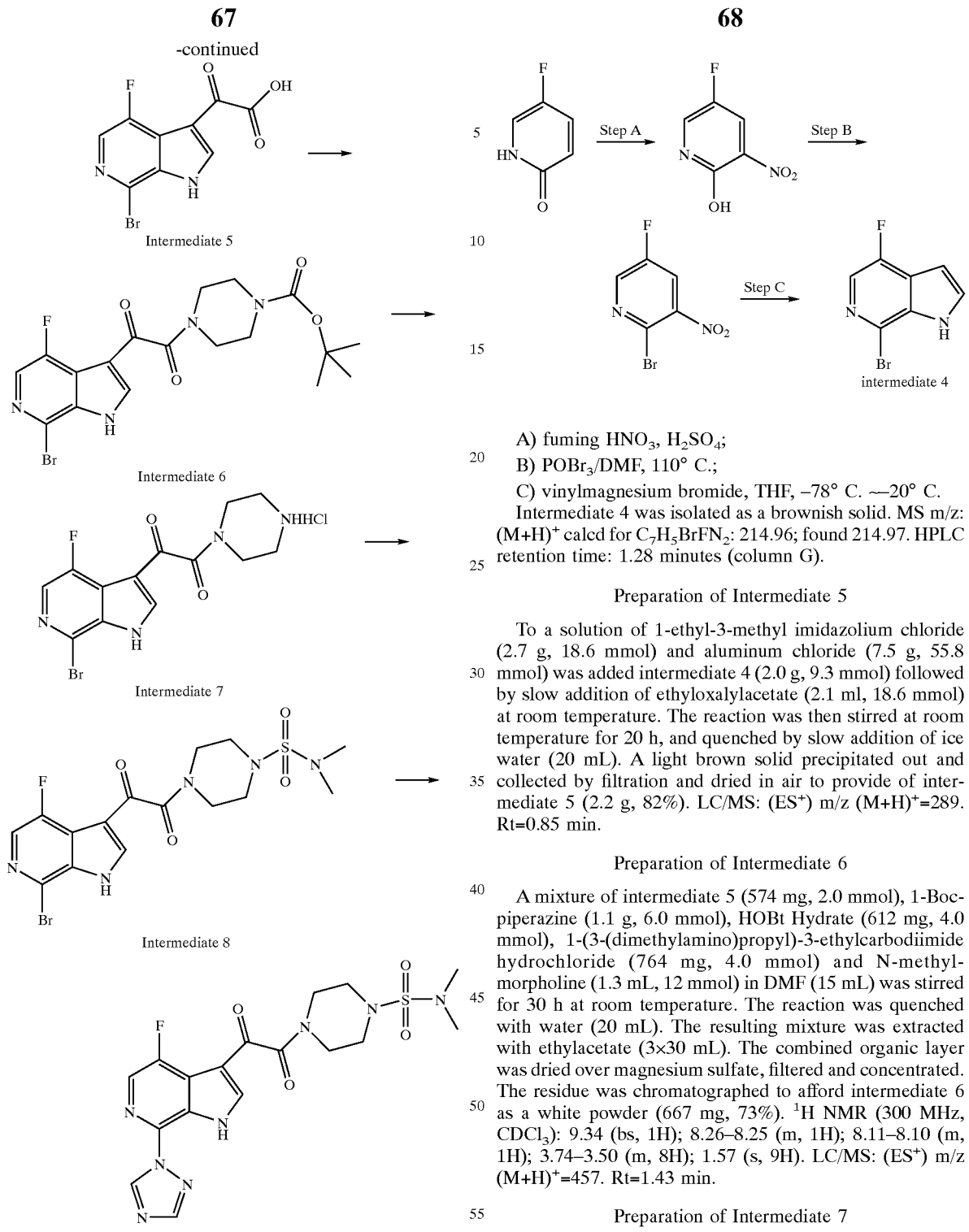

A) fuming $HNO_3$, $H_2SO_4$;
B) $POBr_3$/DMF, 110° C.;
C) vinylmagnesium bromide, THF, −78° C. ∼−20° C.

Intermediate 4 was isolated as a brownish solid. MS m/z: $(M+H)^+$ calcd for $C_7H_5BrFN_2$: 214.96; found 214.97. HPLC retention time: 1.28 minutes (column G).

Preparation of Intermediate 5

To a solution of 1-ethyl-3-methyl imidazolium chloride (2.7 g, 18.6 mmol) and aluminum chloride (7.5 g, 55.8 mmol) was added intermediate 4 (2.0 g, 9.3 mmol) followed by slow addition of ethyloxalylacetate (2.1 ml, 18.6 mmol) at room temperature. The reaction was then stirred at room temperature for 20 h, and quenched by slow addition of ice water (20 mL). A light brown solid precipitated out and collected by filtration and dried in air to provide of intermediate 5 (2.2 g, 82%). LC/MS: $(ES^+)$ m/z $(M+H)^+$=289. Rt=0.85 min.

Preparation of Intermediate 6

A mixture of intermediate 5 (574 mg, 2.0 mmol), 1-Boc-piperazine (1.1 g, 6.0 mmol), HOBt Hydrate (612 mg, 4.0 mmol), 1-(3-(dimethylamino)propyl)-3-ethylcarbodiimide hydrochloride (764 mg, 4.0 mmol) and N-methylmorpholine (1.3 mL, 12 mmol) in DMF (15 mL) was stirred for 30 h at room temperature. The reaction was quenched with water (20 mL). The resulting mixture was extracted with ethylacetate (3×30 mL). The combined organic layer was dried over magnesium sulfate, filtered and concentrated. The residue was chromatographed to afford intermediate 6 as a white powder (667 mg, 73%). $^1H$ NMR (300 MHz, $CDCl_3$): 9.34 (bs, 1H); 8.26–8.25 (m, 1H); 8.11–8.10 (m, 1H); 3.74–3.50 (m, 8H); 1.57 (s, 9H). LC/MS: $(ES^+)$ m/z $(M+H)^+$=457. Rt=1.43 min.

Preparation of Intermediate 7

Intermediate 6 (417 mg, 0.92 mmol) was treated with 4N HCl in dioxane (5 mL, 20 mmol). After stirring for 15 h, the reaction mixture was concentrated on rotoevaporator and dried in vacuo. The resulting light yellow powder was characterized by LCMS and carried to the next step without purification. LC/MS: $(ES^+)$ m/z $(M+H)^+$=357. Rt=0.55 min.

Preparation of Intermediate 8

Intermediate 7 (103 mg, 0.26 mmol) was dissolved in dichloromethane (1.5 mL) and treated with dimethylsufamoyl chloride (56 ul, 0.52 mmol) followed by triethylamine Preparation of Intermediate 4

Intermediate 4,4-fluoro-7-bromo-6-azaindole, was prepared according to the following scheme:

(100 ul, 0.78 mmol). The reaction was stirred for 15 h at room temperature. The solid was filtered out. The filtrate was concentrated and dried in vacuo to provide intermediate 8 as a yellow solid which was used in the next step without further purification. $^1$H-NMR (300 MHz, CDCl3): 9.25 (bs, 1H); 8.26–8.25 (m, 1H); 8.12–8.11 (m, 1H); 3.84–3.31 (m, 8H); 2.85 (s, 6H). LC/MS: (ES$^+$) m/z (m+H)$^+$=464. Rt=1.06 min.

Preparation of Compound Example 12

A mixture of intermediate 8 (53 mg, 0.12 mmol), 1,2,4-triazole (248 mg, 3.5 mmol), copper powder (8 mg, 0.12 mmol) and potassium carbonate (17 mg, 0.12 mmol) was heated at 160° C. for 7 h in a sealed tube. The reaction was cooled to room temperature and filtered through filter paper. The filtrate was diluted with methanol and purified by preparative HPLC to provide the title compound (5.1 mg, 10%). $^1$H-NMR (500 MHz, CDCl$_3$): 11.09 (bs, 1H); 9.30 (s, 1H); 8.32–8.31 (m, 1H); 8.24 (s, 1H); 8.11–8.10 (m, 1H); 3.85–3.33(m, 8H); 2.85 (s, 6H). LC/MS: (ES$^+$) m/z (m+H)$^+$=451. Rt=1.12 min.

EXAMPLE 13 AND 14

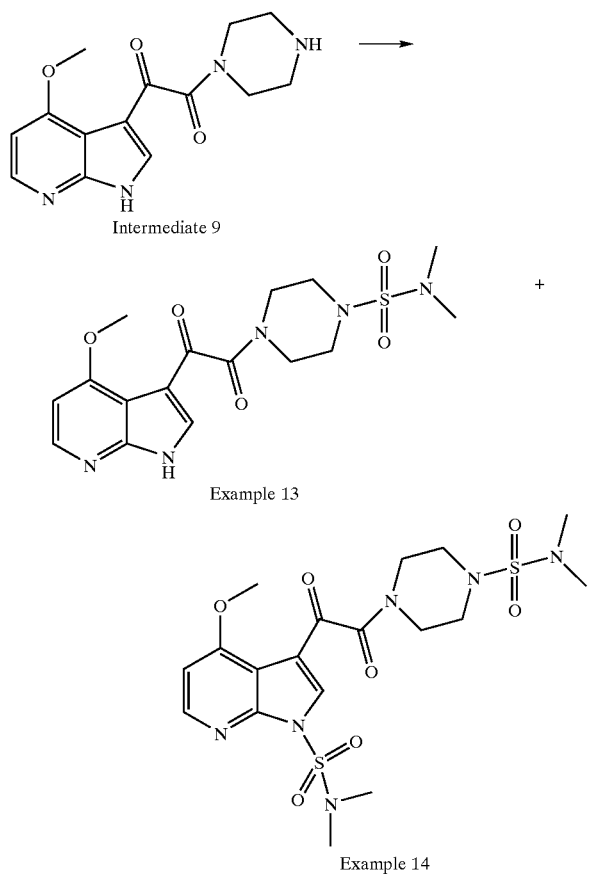

Examples 13 and 14 were prepared from intermediate 9 as described in example 3. (The synthesis of intermediate 9 is described in Wang, T. et al., PCT WO0162255). Example 13: $^1$H-NMR (300 MHz, CDCl$_3$): 8.33–8.30 (m, 1H); 8.15–8.12 (m, 1H); 7.00–6.97 (m, 1H); 4.23 (s, 3H); 4.22–2.83 (m, 7H); 2.84 (s, 6H); 1.42–1.40 (m, 3H). LC/MS: (ES$^+$) m/z (m+H)$^+$=410. Rt=0.87 min; Example 14: $^1$H-NMR (300 MHz, CDCl$_3$): 8.38–8.36 (m, 1H); 8.28–8.23 (m, 1H); 6.81–6.79 (m, 1H); 4.02 (s, 3H); 3.90–2.85 (m, 7H), 3.07 (s, 6H); 2.85 (s, 6H); 1.42–1.40 (m, 3). LC/MS: (ES$^+$) m/z (m+H)$^+$=517. Rt=1.30 min.

Biology

"µM" means micromolar;

"mL" means milliliter;

"µl" means microliter;

"mg" means milligram;

The materials and experimental procedures used to obtain the results reported in Tables 1–2 are described below.

Cells:

Virus production—Human embryonic Kidney cell line, 293T, was propagated in Dulbecco's Modified Eagle Medium (Invitrogen, Carlsbad, Calif.) containing 10% fetal Bovine serum (FBS, Sigma, St. Louis, Mo.).

Virus infection—Human epithelial cell line, HeLa, expressing the HIV-1 receptor CD4 was propagated in Dulbecco's Modified Eagle Medium (Invitrogen, Carlsbad, Calif.) containing 10% fetal Bovine serum (FBS, Sigma, St. Louis, Mo.) and supplemented with 0.2 mg/mL Geneticin (Invitrogen, Carlsbad, Calif.).

Virus—Single-round infectious reporter virus was produced by co-transfecting human embryonic Kidney 293 cells with an HIV-1 envelope DNA expression vector and a proviral cDNA containing an envelope deletion mutation and the luciferase reporter gene inserted in place of HIV-1 nef sequences (Chen et al, Ref. 41). Transfections were performed using lipofectAMINE PLUS reagent as described by the manufacturer (Invitrogen, Carlsbad, Calif.).

Experiment

1. HeLa CD4 cells were plated in 96 well plates at a cell density of 1×10$^4$ cells per well in 100 µl Dulbecco's Modified Eagle Medium containing 10% fetal Bovine serum and incubated overnight.
2. Compound was added in a 2 µl dimethylsulfoxide solution, so that the final assay concentration would be ≦10 µM.
3. 100 µl of single-round infectious reporter virus in Dulbecco's Modified Eagle Medium was then added to the plated cells and compound at an approximate multiplicity of infection (MOI) of 0.01, resulting in a final volume of 200 µl per well.
4. Virally-infected cells were incubated at 37 degrees Celsius, in a CO$_2$ incubator, and harvested 72 h after infection.
5. Viral infection was monitored by measuring luciferase expression from viral DNA in the infected cells using a luciferase reporter gene assay kit, as described by the manufacturer (Roche Molecular Biochemicals, Indianapolis, Ind.). Infected cell supernatants were removed and 50 µl of lysis buffer was added per well. After 15 minutes, 50 µl of freshly-reconstituted luciferase assay reagent was added per well. Luciferase activity was then quantified by measuring luminescence using a Wallac microbeta scintillation counter.

6. The percent inhibition for each compound was calculated by quantifying the level of luciferase expression in cells infected in the presence of each compound as a percentage of that observed for cells infected in the absence of compound and subtracting such a determined value from 100.

7. An $EC_{50}$ provides a method for comparing the antiviral potency of the compounds of this invention. The effective concentration for fifty percent inhibition ($EC_{50}$) was calculated with the Microsoft Excel Xlfit curve fitting software. For each compound, curves were generated from percent inhibition calculated at 10 different concentrations by using a four paramenter logistic model (model 205). The $EC_{50}$ data for the compounds is shown in Table 2. Table 1 is the key for the data in Table 2.

Results

TABLE 1

Biological Data Key for $EC_{50}s$

| Compounds* with $EC_{50}s > 5 \mu M$ | Compounds with $EC_{50}s > 1 \mu M$ but $< 5 \mu M$ | Compounds with $EC_{50} < 1 \mu M$ |
|---|---|---|
| Group C | Group B | Group A |

*Some of these compounds may have been tested at a concentration lower than their $EC_{50}$ but showed some ability to cause inhibition and thus should be evaluated at a higher concentration to determine the exact $EC_{50}$.

In Table 2, $X_W$, $X_Z$, and $X_S$ indicate the points of attachment for groups Z, W and A in Compounds I. For example in table entry 1, for group Z, the point of attachment to group W is indicated in group Z as "$X_W$"; for group W, the point of attachment to group Z is "$X_Z$" and the point of attachment to S is "$X_S$".

TABLE 2

Examples

TABLE 2-continued

Examples (I)

[Structure: O=S(=O)(A)-W-Z]

| Table Entry (Example Number.) | Z | W | A | EC$_{50}$ Group from Table 1 |
|---|---|---|---|---|
| 4 (Example 4) | 4-F, 7-(C(=O)NHMe) indol-3-yl glyoxalyl-Xw | Xz—N(piperazine)N—Xs | Xs—N(H)—Me | C |
| 5 (Example 5) | 4-F, 7-(CO$_2$Me) indol-3-yl glyoxalyl-Xw | Xz—N(piperazine)N—Xs | Xs—N(Me)$_2$ | C |
| 6 (Example 6) | 4-F, 7-(CO$_2$Me) indol-3-yl glyoxalyl-Xw | Xz—N(piperazine)N—Xs | Xs—N(azetidine) | C |
| 7 (Example 7) | 4-F, 7-(CO$_2$Me) indol-3-yl glyoxalyl-Xw | Xz—N(piperazine)N—Xs | Xs—N(piperidine) | B |
| 8 (Example 8) | 4-F, 7-(CO$_2$Me) indol-3-yl glyoxalyl-Xw | Xz—N(piperazine)N—Xs | Xs—N(Et)$_2$ | B |

TABLE 2-continued

Examples (I)

$$\text{Z—W—S(=O)(=O)—A}$$

| Table Entry (Example Number.) | Z | W | A | EC$_{50}$ Group from Table 1 |
|---|---|---|---|---|
| 9 (Example 9) | 4-fluoro-7-(N-methylcarboxamide)-indol-3-yl glyoxyl | Xz—N(piperazine)N—Xs | Xs—N(piperidine) | B |
| 10 (Example 10) | 4-fluoro-7-(N-methylcarboxamide)-indol-3-yl glyoxyl | Xz—N(piperazine)N—Xs | Xs—N(azetidine) | C |
| 11 (Example 11) | 4-fluoro-7-(N-methylcarboxamide)-indol-3-yl glyoxyl | Xz—N(piperazine)N—Xs | Xs—N(diethyl) | B |
| 12 (Example 12) | 4-fluoro-7-(1,2,4-triazol-1-yl)-pyrrolo[2,3-c]pyridin-3-yl glyoxyl | Xz—N(piperazine)N—Xs | Xs—N(dimethyl) | A |

TABLE 2-continued

Examples (I)

$$Z-W-\underset{\underset{O}{\|}}{\overset{\overset{O}{\|}}{S}}-A$$

| Table Entry (Example Number.) | Z | W | A | EC$_{50}$ Group from Table 1 |
|---|---|---|---|---|
| 12 (Example 13) | [4-methoxy-7-azaindol-3-yl-glyoxylyl, Xw] | Xz—N(piperazine, methyl)N—Xs | Xs—N(CH$_3$)$_2$ | A |
| 14 (Example 14) | [4-methoxy-7-azaindol-3-yl-glyoxylyl, N-sulfonyl-N-methylamide, Xw] | Xz—N(piperazine, methyl)N—Xs | Xs—N(CH$_3$)$_2$ | C |

The compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically acceptable carriers, adjuvants and diluents.

Thus, in accordance with the present invention, there is further provided a method of treating and a pharmaceutical composition for treating viral infections such as HIV infection and AIDS. The treatment involves administering to a patient in need of such treatment a pharmaceutical composition comprising a pharmaceutical carrier and a therapeutically effective amount of a compound of the present invention.

The pharmaceutical composition may be in the form of orally administrable suspensions or tablets; nasal sprays, sterile injectable preparations, for example, as sterile injectable aqueous or oleagenous suspensions or suppositories.

When administered orally as a suspension, these compositions are prepared according to techniques well known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds of this invention can be administered orally to humans in a dosage range of 1 to 100 mg/kg body weight in divided doses. One preferred dosage range is 1 to 10 mg/kg body weight orally in divided doses. Another preferred dosage range is 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

What is claimed is:

1. A compound of Formula I, including pharmaceutically acceptable salts thereof,

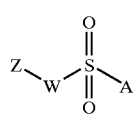

(I)

wherein:

Z is

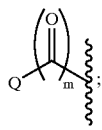

Q is selected from the group consisting of:

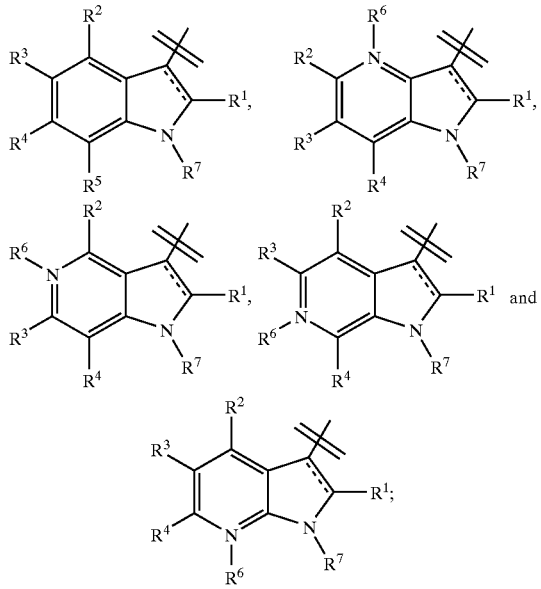

—W— is

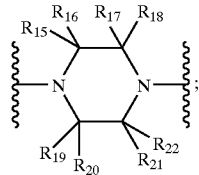

$R^1$, $R^2$, $R^3$, $R^4$, and $R^5$, are independently selected from the group consisting of hydrogen, halogen, cyano, nitro, $COOR^8$, $XR^9$ and B;

$R^{15}$, $R^{16}$, $R^{17}$, $R^{18}$, $R^{19}$, $R^{20}$, $R^{21}$ and $R^{22}$ are each independently H or $(C_{1-6})$alkyl; wherein $(C_{1-6})$alkyl is optionally substituted with one to three same or different members selected from the group consisting of halogen, amino, OH, CN and $NO_2$;

m is 1 or 2;

$R^6$ is O or does not exist;

$R^7$ is $(CH_2)_nR^{10}$, $SO_2NH_2$, $SO_2NHMe$ or $SO_2NMe_2$;

n is 0–6;

$R^{10}$ is selected from the group consisting of H, $(C_{1-6})$alkyl, —C(O)—$(C_{1-6})$alkyl, C(O)-phenyl and $CONR^{11}R^{12}$;

$R^{11}$ and $R^{12}$ are each independently H, $(C_{1-6})$alkyl or phenyl;

— represents a carbon-carbon bond or does not exist;

A is $NR^{13}R^{14}$;

$R^{13}$ and $R^{14}$ are independently selected from the group consisting of hydrogen, $(C_{1-6})$alkyl, $(C_{1-6})$cycloalkyl, and phenyl; or $R^{13}$ and $R^{14}$ taken together with the nitrogen atom to which they are attached forms a heteroalicyclic ring having 3 to 6 atoms; wherein heteroalicyclic is selected from the group consisting of azetidinyl, piperidinyl, piperazinyl, pyrrolidinyl, morpholinyl, thiomorpholinyl, tetrahydrofuranyl and tetrahydropyranyl, B is selected from the group consisting of $(C_{1-6})$alkyl, $(C_{3-6})$cycloalkyl, $C(O)NR^{23}R^{24}$, phenyl and heteroaryl; wherein said heteroaryl is selected from the group consisting of pyridinyl, pyrazinyl, pyridazinyl, pyrimidinyl, furanyl, thienyl, benzothienyl, thiazolyl isothiazolyl, oxazolyl, benzooxazolyl, isoxazolyl, imidazolyl, benzoimidazolyl, 1H-imidazo[4,5-b]pyridin-2-yl, 1H-imidazo[4,5-c]pyridin-2-yl, oxadiazolyl, thiadiazolyl, pyrazolyl, tetrazolyl, tetrazinyl, triazinyl and triazolyl;

$R^8$ and $R^9$ are independently selected from the group consisting of hydrogen and $(C_{1-6})$alkyl;

X is selected from the group consisting of $NR^{31}$, O and S;

$R^{23}$, $R^{24}$ and $R^{31}$ are independently selected from the group consisting of hydrogen, $(C_{1-6})$alkyl, and heteroaryl; wherein said heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl.

2. A compound of claim 1 wherein:

Z is

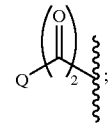

$R^1$ is hydrogen;

— represents a carbon-carbon bond; and $R^6$ does not exist.

3. A compound of claim 2 wherein:

$R^7$ is hydrogen; and $R^{15}$, $R^{16}$, $R^{17}$, $R^{18}$, $R^{19}$, $R^{20}$, $R^{21}$, $R^{22}$ are each independently H or methyl with the proviso that a maximum of one of $R^{15}$–$R^{22}$ is methyl.

4. A compound of claim 3 wherein:

Q is a member selected from groups (A) and (B) consisting of:

(A)

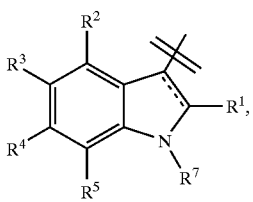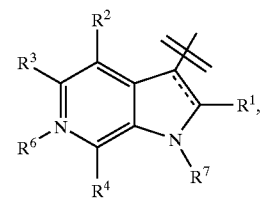

-continued

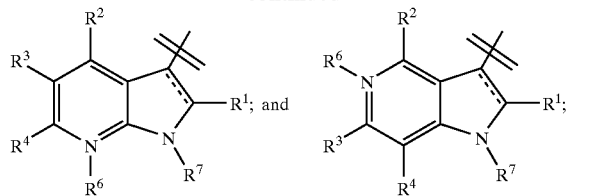

provided R² and R³ are each independently hydrogen, methoxy or halogen; and

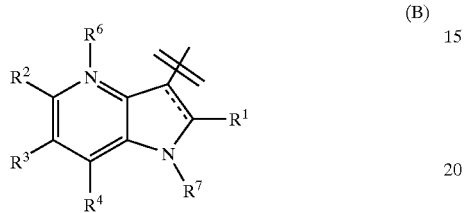

provided R² is hydrogen, methoxy or halogen.

5. A compound of claim 4 wherein:

Q is a member selected from groups (A), (B) and (C) consisting of:

(A)

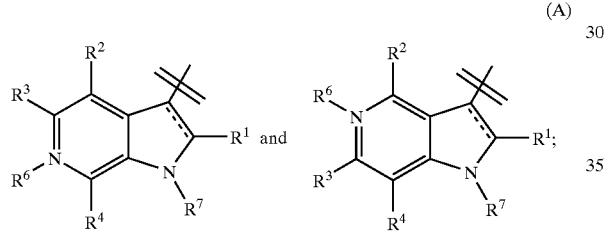

provided R² is hydrogen, methoxy or halogen; R³ is hydrogen;

(B)

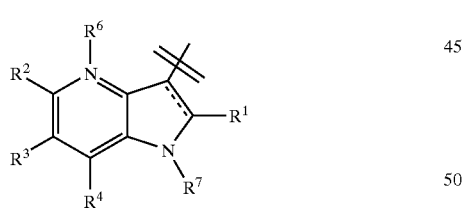

provided R² and R³ are hydrogen; and (C)

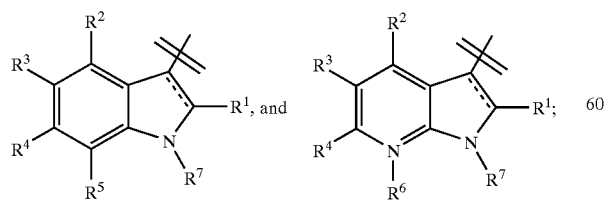

provided R² is hydrogen, methoxy or halogen; and R³ and R⁴ are hydrogen.

6. A compound of claim 4 wherein:

Q is

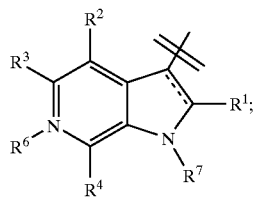

provided R² is hydrogen, methoxy or halogen; and R³ is hydrogen.

7. A compound of claim 4 wherein:

Q is

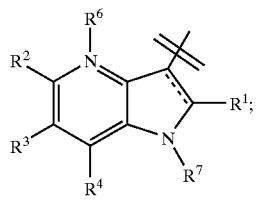

and R² and R³ are hydrogen.

8. A compound of claim 4 wherein:

Q is

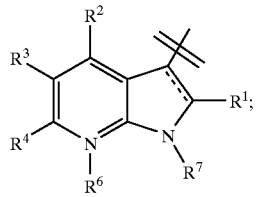

R² is hydrogen, methoxy or halogen; and R³ and R⁴ are hydrogen.

9. A compound of claim 4 wherein:

Q is:

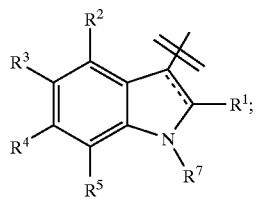

R² is hydrogen, methoxy or halogen; and R³ and R⁴ are hydrogen.

10. A compound of claims 3, 5, 6, 7 or 9 wherein:

B is selected from the group consisting of —C(O)NR²³R²⁴, phenyl and heterparyl.

11. A compound of claims 3, 5 or 6 wherein:

A is selected from the group consisting of —NH(C₁–C₆alkyl) and —N(C₁–C₆alkyl)₂.

12. A compound of claim 5 wherein:

A is selected from the group consisting of —NH(C$_1$–C$_6$alkyl) and —N(C$_1$–C$_6$alkyl)$_2$; and B is —C(O)NHMe or —C(O)NH-heteroaryl.

13. A compound of claim 5 wherein:

A is selected from the group consisting of —NH(C$_1$–C$_6$alkyl) and —N(C$_1$–C$_6$alkyl)$_2$; and B is -triazolyl or pyrazolyl.

14. A pharmaceutical formulation which comprises an antiviral effective amount of a compound of Formula I, including pharmaceutically acceptable salts thereof, as claimed in claim 1, and a pharmaceutically acceptable carrier.

15. A method for treating mammals infected with the HIV virus, comprising administering to said mammal an antiviral effective amount of a compound of Formula I, including pharmaceutically acceptable salts thereof, as claimed in claim 1.

* * * * *